US010711311B2

(12) United States Patent
Srivastava et al.

(10) Patent No.: US 10,711,311 B2
(45) Date of Patent: Jul. 14, 2020

(54) GENOMIC REARRANGEMENTS ASSOCIATED WITH PROSTATE CANCER AND METHODS OF USING THE SAME

(71) Applicants: The Henry M. Jackson Foundation for the Advancement of Military Medicine, Inc., Bethesda, MD (US); Genomatix, Munich (DE)

(72) Inventors: Shiv K. Srivastava, Potomac, MD (US); Albert Dobi, Rockville, MD (US); Gyorgy Petrovics, Bethesda, MD (US); Thomas Werner, Munich (DE); Martin Seifert, Fischen/Pähl (DE); Matthias Scherf, Gröbenzell (DE)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 15/108,951

(22) PCT Filed: Dec. 30, 2014

(86) PCT No.: PCT/US2014/072793
§ 371 (c)(1),
(2) Date: Jun. 29, 2016

(87) PCT Pub. No.: WO2015/103287
PCT Pub. Date: Jul. 9, 2015

(65) Prior Publication Data
US 2016/0326595 A1 Nov. 10, 2016

Related U.S. Application Data

(60) Provisional application No. 61/921,780, filed on Dec. 30, 2013.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS

| 2005/0119171 A1 | 6/2005 | Bejanin et al. | |
| 2011/0065113 A1* | 3/2011 | Chinnaiyan | C12Q 1/6886 435/6.12 |
| 2011/0070583 A1 | 3/2011 | Vance et al. | |
| 2011/0136683 A1 | 6/2011 | Davicioni | |
| 2011/0236903 A1* | 9/2011 | McClelland | C12Q 1/6886 435/6.14 |

FOREIGN PATENT DOCUMENTS

| EP | 1716227 A2 | 11/2006 |
| JP | 2005-511012 A | 4/2005 |
| WO | 2005047519 A2 | 5/2005 |
| WO | 2005071059 A2 | 8/2005 |
| WO | 2015175732 A2 | 11/2015 |

OTHER PUBLICATIONS

Juppner (Bone 1995 vol. 17 No. 2 Supplement 39S-42S) (Year: 1995).*
International Search Report and Written Opinion dated May 28, 2015 from International Application No. PCT/US2014/072793, pp. 1-12.
Siegel et al., Cancer statistics, 2013, CA Cancer J. Clin., vol. 63, pp. 11-30.
Chornokur et al., "Disparities at presentation, diagnosis, treatment, and survival in African American men affected by prostate cancer", Prostate, Jun. 15, 2011, vol. 71, No. 9, pp. 985-997.
Schwartz et al., "Interplay of Race, Socioeconomic Status and Treatment on Survival of Prostate Cancer Patients", Urology, Dec. 2009, vol. 74, No. 6, pp. 1296-1302.
Major et al., "Socioeconomic status, healthcare density, and risk of prostate cancer among African American and Caucasian men in a large prospective study", Cancer Causes Control, Jul. 2012, vol. 23, No. 7, pp. 1185-1191.
Sridhar et al., "Do African American men have lower survival from prostate cancer compared with White men? A meta-analysis", Am. J Mens. Health, 2010, vol. 4, No. 3, pp. 189-206.
Cullen et al., "Racial/ethnic patterns in prostate cancer outcomes in an active surveillance cohort", Prostate Cancer 2011, vol. 2011, Article ID 234519, 9 pages.
Berger et al., "Differences in clinicopathologic features of prostate cancer between black and white patients treated in the 1990s and 2000s", Urology, Jan. 2006, vol. 67, No. 1, pp. 120-124.
Kheirandish et al., "Ethnic differences in prostate cancer", British Journal of Cancer, 2011, vol. 105, pp. 481-485.

(Continued)

*Primary Examiner* — Katherine D Salmon
(74) *Attorney, Agent, or Firm* — MH2 Technology Law Group, LLP

(57) ABSTRACT

The present disclosure provides genomic arrangements of the chromosome 3q13 region that are associated with prostate cancer, such as rearrangements between the ZBTB20 and LSAMP genes, including gene fusions between the ZBTB20 gene and the LSAMP gene and deletions spanning both genes. The ZBTB20/LSAMP genomic rearrangement serves as a biomarker for prostate cancer and can be used to stratify prostate cancer based on ethnicity or the severity or aggressiveness of prostate cancer and/or identify a patient for prostate cancer treatment. Another aspect involves discovering that deletions of the PTEN gene are observed predominately in prostate cancer from subjects of Caucasian descent. Also provided are kits for diagnosing and prognosing prostate cancer.

6 Claims, 5 Drawing Sheets
Specification includes a Sequence Listing.

(56) References Cited

OTHER PUBLICATIONS

Odedina et al., "Prostate cancer disparities in black men of African descent: A comparative literature review of prostate cancer burden among black men in the United States, Caribbean, United Kingdom, and West Africa", Infectious Agents Cancer, 2009, vol. 4(Suppl 1), 8 pages.
Heath et al., "The effect of race/ethnicity on the accuracy of the 2001 Partin Tables for predicting pathologic stage of localized prostate cancer", Urology 2008, vol. 71, No. 1, pp. 151-155.
Moul et al., "Prostate-specific antigen values at the time of prostate cancer diagnosis in African-American men", JAMA Oct. 25, 1995, vol. 274, No. 16, pp. 1277-1281.
Tewari et al., "Racial differences in serum prostate-specific (PSA) doubling time, histopathological variables and long-term PSA recurrence between African-American and white American men undergoing radical prostatectomy for clinically localized prostate cancer", BJU Int., 2005, vol. 96, pp. 29-33.
Wallace et al., "Tumor immunobiological differences in prostate cancer between African-American and European-American men", Cancer Research., Feb. 1, 2008, vol. 68, No. 3, pp. 927-936.
Prensner et al., "Beyond PSA: The next generation of prostate cancer biomarkers", Sci. Transl. Med., Mar. 28, 2012, vol. 4, Issue 127, 12 pages.
Rubin et al., "Common gene rearrangements in prostate cancer". J. Clin. Oncol., 2011, vol. 29, No. 27, pp. 3659-3668.
Sreenath et al., "Oncogenic activation of ERG: A predominant mechanism in prostate cancer", J. Carcinog., 2011, vol. 10, No. 37, 24 pages.
Petrovics et al., "Frequent overexpression of ETS-related gene-1 (ERG1) in prostate cancer transcriptome", Oncogene, 2005, vol. 24, pp. 3847-3852.
Tomlins et al., "Recurrent fusion of TMPRSS2 and ETS transcription factor genes in prostate cancer", Science, Oct. 28, 2005, vol. 310, pp. 644-648.
Magi-Galluzzi et al., "TMPRSS2-ERG gene fusion prevalence and class are significantly different in prostate cancer of Caucasin African-American and Japanese patients", Prostate, 2011, vol. 71, No. 5, pp. 489-497.
Rosen et al., "Differences in the frequency of ERG oncoprotein expression between index tumors of Caucasian American and African American prostate cancer patients", Urology, Oct. 2012, vol. 80, No. 4, pp. 749-753.
Hu, Y et al., "Delineation of TMPRSS2-ERG splice variants in prostate cancer", Clin. Cancer Res., Aug. 1, 2008, vol. 14, No. 15, pp. 4719-4725.
Geiss et al., "Direct multiplexed measurement of gene expression with color-coded probe pairs", Nature Biotechnology, Mar. 2008, vol. 26, No. 3, pp. 317-325.
Fortina et al., "Digital mRNA Profiling", Nature Biotechnology, Mar. 2008, vol. 26, No. 3, pp. 293-294.
Farrell et al., "Genetic and molecular differences in prostate carcinogenesis between African American and Caucasian American men", International Journal of Molecular Sciences, 2013, vol. 14, No. 8, pp. 15510-15531.
Rodriquez-Suarez et al., "Urine as a source for clinical proteome analysis: From discovery to clinical application", Biochimica et Biophysica Acta, 2013, 15 pages.
Shi et al., "Antibody-free, targeted mass-spectrometric approach for quantification of proteins at low picogram per milliliter levels in human plasma/serum", PNAS, Sep. 18, 2012, vol. 109, No. 38, pp. 15395-15400.
Conlon et al., "Fusion Peptides from Oncogenic Chimeric Proteins as Putative Specific Biomarkers of Cancer", Molecular & Cellular Proteomics, Oct. 2013, vol. 12, No. 10, pp. 2714-2723.
McCubrey et al., "Ras/Raf/MEK/ERK and PI3K/PTEN/Akt/mTOR Cascade Inhibitors: How Mutations Can Result in Therapy Resistance and How to Overcome Resistance", Oncotarget, Oct. 2012, vol. 3, No. 10, pp. 1068-1111.
Kuhn et al., "High-resolution genomic profiling of adult and pediatric core-binding factor acute myeloid leukemia reveals new recurrent genomic alterations", Blood, Mar. 8, 2012, vol. 119, No. 10, pp. e67-e75.
Pasic et al., "Recurrent Focal Copy Number Changes and Loss of Heterozygosity Implicate Two Non-Coding RNAs and One Tumor Suppressor Gene at Chromosome 3q13.31 in Osteosarcoma", Cancer Research, Jan. 1, 2010, vol. 70, No. 1, pp. 160-171.
Chen et al., "The t(1;3) breakpoint-spanning genes LSAMP and NORE1 are involved in clear cell renal cell carcinomas", Cancer Cell, Nov. 2003, vol. 4, pp. 405-413.
Ntougkos et al., "The IgLON Family in Epithelial Ovarian Cancer: Expression Profiles and Clinicopathologic Correlates", Clin Cancer Res, Aug. 15, 2005, vol. 11, No. 16, pp. 5764-5768.
Ren et al., "Long non-coding RNA metastatis associated in lung adenocarcinoma transcript 1 derived miniRNA as a novel plasma-based biomarker for diagnosing prostate cancer", Eur J Cancer, 2013, vol. 49, pp. 2949-2959.
Mao et al., "Distinct Genomic Alterations in Prostate Cancers in Chinese and Western Populations Suggest Alternative Pathways of Prostate Carcinogenesis", Cancer Research, 2010, vol. 70, No. 13, pp. 5207-5212.
Blattner et al., "SPOP Mutations in Prostate CAncer across Demographically Diverse Patient Cohorts", Neoplasia, Jan. 2014, vol. 16, No. 1, pp. 14-20.
Khani et al., "Evidence for Molecular Differences in Prostate Cancer between African American and Caucasian Men", Clin Cancer Res., Sep. 15, 2014, vol. 20, No. 18, pp. 4925-4934.
Lowther et al., "Adult expression of a 3q13.31 microdeletion", Mol. Cytogenet., Mar. 2014, vol. 7, No. 1, pp. 23-26.
Molin et al., "A novel microdeletion syndrome at 3q13.31 characterised by developmental delay, postnatal overgrowth, hypoplastic male genitals, and characteristic facial features", J. Med. Genet, Feb. 2012, vol. 49, No. 2, pp. 104-109.
Extended European Search Report (includes Supplementary European Search Report and European Search Opinion) dated Jul. 14, 2017 for European Patent Application No. 14877000.1, 7 pages.
Office Action dated Nov. 6, 2018 for Japanese Patent Application No. 2016-561994, 22 pages with English Translation.

\* cited by examiner

Genomic structure of the Z-L fusion
(chromosome 3q13, negative strand)

Z-L fusion junction (cDNA)
Fusion junction

ZBTB20 exon1        LSAMP exon4

5'-AAGATTAAAGAGCGCGAGGAGGAAGGGAATTTGAAGGAGA-3'

Z-L fusion sequence read
(reverse orientation)

TCTCCTTCAAATTCCCTTCCTCCTCGCGCTCTTTAATCTT

| | E1 (62) | E1A (95) | E1B (119) | E1C (121) | E0* (365) | E1 (662) | E2 (233) | E3 (126) | E3* (140) | E4 (135) | E5 (121) | E6 (149) | E7 (8052) |
|---|---|---|---|---|---|---|---|---|---|---|---|---|---|
| Type 1 | E1 | | | | | | | | | E4 | E5 | E6 | E7 |
| Type 2 | | | | E1C(121) | | | | | E3*(140) | E4 | E5 | E6 | E7 |
| Type 3 | | | | E1C(121) | | | | | | E4 | E5 | E6 | E7 |
| Type 4 | E1 | E1A(93) | E1B(116) | | | | | | | E4 | | | |
| Type 5 | E1 | E1*A(95) | | | | | | | | E4 | | | |
| Type 6 | E1 | | E1B(119) | | | | | | | E4 | | | |
| Type 7 | E1 | | | | | | | | | E4 | | | |
| Type 8 | E1 | | | E1C(121) | | | | | E3*(140) | E4 | | | |
| Type 9 | | | | E1C(121) | | | | | | E4 | | | |
| Type 10 | | | | E1C(121) | | | | | E3*(140) | E4 | | | |
| LPCS1 | | | | | E0*(365) | E1 (81) | E2 | E3 | | E4 | | | |

5' ZBTB20 -> 3' LSAMP cDNA Fusion and Exon Map

FIG. 5

GENOMIC REARRANGEMENTS ASSOCIATED WITH PROSTATE CANCER AND METHODS OF USING THE SAME

CROSS-REFERENCE TO RELATED APPLICATIONS

This application is a U.S. National Stage application of PCT/US2014/072793 filed 30 Dec. 2014, which claims the benefit of, and relies on the filing date of, U.S. provisional patent application No. 61/921,780, filed 30 Dec. 2013, the entire disclosure of which is incorporated herein by reference.

GOVERNMENT INTEREST

This invention was made with government support under HU 0001-10-2-0002 awarded by the Uniformed Servcies University of the Health Sciences. The government has certain rights in the invention.

SEQUENCE LISTING

The instant application contains a Sequence Listing which has been submitted electronically in ASCII format and is hereby incorporated by reference in its entirety. Said ASCII copy, created on Dec. 30, 2014, is named HMJ-149-PCT-_SL.txt and is 205,868 bytes in size.

BACKGROUND

In 2013 an estimated 238,590 men will be diagnosed with carcinoma of the prostate (CaP) and an estimated 29,720 men will die from the disease [1]. This malignancy is the second leading cause of cancer-related death in men in the United States. In addition, African American (AA) men have the highest incidence and mortality from CaP compared with other races [1]. The racial disparity exists from presentation and diagnosis through treatment, survival, and quality of life [2]. Researchers have suggested that socio-economic status (SES) contributes significantly to these disparities including CaP-specific mortality [3]. As well, there is evidence that reduced access to care is associated with poor CaP outcomes, which is more prevalent among AA men than Caucasian American (CA) men [4].

However, there are populations in which AA men have similar outcomes to CA men. Sridhar and colleagues [5] published a meta-analysis in which they concluded that when SES is accounted for, there are no differences in the overall and CaP-specific survival between AA and CA men. Similarly, the military and veteran populations (systems of equal access and screening) do not observe differences in survival across race [6], and differences in pathologic stage at diagnosis narrowed by the early 2000s in a veterans' cohort [7]. Of note, both of these studies showed that AA men were more likely to have higher Gleason scores and PSA levels than CA men [6, 7].

While socio-economic factors may contribute to CaP outcomes, they do not seem to account for all variables associated with the diagnosis and disease risk. Several studies support that AA men have a higher incidence of CaP compared to CA men [1, 8, 9]. Studies also show that AA men have a significantly higher PSA at diagnosis, higher grade disease on biopsy, greater tumor volume for each stage, and a shorter PSA doubling time before radical prostatectomy [10-12]. Biological differences between prostate cancers from CA and AA men have been noted in the tumor microenvironment with regard to stress and inflammatory responses [13]. Although controversy remains over the role of biological differences, observed differences in incidence and disease aggressiveness at presentation indicate a potential role for different pathways of prostate carcinogenesis between AA and CA men.

Over the past decade, much research has focused on alterations of cancer genes and their effects in CaP [14-16]. Variations in prevalence across ethnicity and race have been noted in the TMPRSS2/ERG gene fusion that is overexpressed in CaP and is the most common known oncogene in CaP [17, 18]. Accumulating data suggest that there are differences of ERG oncogenic alterations across ethnicities [17, 19-21]. Significantly greater ERG expression in CA men compared to AA men was noted in initial papers describing ERG overexpression and ERG splice variants [17, 21]. The difference is even more pronounced between CA and AA (50% versus 16%) in patients with high Gleason grade (8-10) tumors. [Ferrell et al., manuscript]. Thus, ERG is a major somatic gene alteration between these ethnic groups. Yet beyond TMPRSS2/ERG, little is known regarding the genetic basis for the CaP disparity between AA and CA men remains unknown [24].

Therefore, new biomarkers and therapeutic markers that are specific for distinct ethnic populations and provide more accurate diagnostic and/or prognostic potential are needed.

SUMMARY

The present disclosure provides a genomic arrangement that occurs in chromosome region 3q13 and involves a ZBTB20 gene and an LSAMP gene and methods of diagnosing and prognosing prostate cancer based on the detection of the ZBTB20/LSAMP genomic arrangement in a biological sample comprising prostate cells. The ZBTB20/LSAMP genomic arrangement can be a gene fusion between the ZBTB20 gene and the LSAMP gene, a gene inversion, a gene deletion, or a gene duplication.

Detecting the ZBTB20/LSAMP genomic rearrangement in prostate cells from a subject indicates that the subject has prostate cancer or an increased likelihood to develop prostate cancer or characterizes the prostate cancer in the subject as being an aggressive form of prostate cancer or as having an increased risk of developing into an aggressive form of prostate cancer. The ZBTB20/LSAMP gene rearrangements can be measured at either the nucleic acid or protein level.

In one embodiment, prostate cancer from the subject does not express a gene fusion between ERG and an androgen regulated gene, such as TMPRSS2. In another embodiment, the subject is of African descent. In this way, the ZBTB20/LSAMP genomic rearrangement can be used to prognose the severity of prostate cancer within a particular ethnic group, as the examples show that subjects of African descent who possess the ZBTB20/LSAMP genomic rearrangement in prostate cells, but not the TMPRSS2/ERG fusion, consistently develop an aggressive form of prostate cancer.

Given the prognostic value of the ZBTB20/LSAMP genomic rearrangement, the methods may further comprise a step of selecting a treatment regimen for the subject based on the detection of the ZBTB20/LSAMP genomic rearrangement or of treating the subject if the genomic rearrangement is detected in the biological sample obtained from the subject. Alternatively, the methods may further comprise a step of increasing the frequency of monitoring the subject for the development of prostate cancer or a more aggressive form of prostate cancer.

Another aspect is directed to compositions for diagnosing or prognosing prostate cancer. In one embodiment, the composition comprises a polynucleotide probe, wherein the polynucleotide probe hybridizes under high stringency conditions to a junction of a chimeric nucleic acid, wherein the chimeric nucleic acid comprises a first portion from a ZBTB20 gene and a second portion from a LSAMP gene ("the ZBTB20/LSAMP polynucleotide probe"). In one embodiment, the first portion comprises exon 1 of the ZBTB20 gene and the second portion comprises exon 3* or exon 4 of LSAMP. In other embodiments, the polynucleotide probe hybridizes under high stringency conditions to exon 3* of a LSAMP gene or a junction of a chimeric nucleic acid, wherein the chimeric nucleic acid comprises a first portion from exon 3* of a LSAMP gene and a second portion from exon 4 of a LSAMP gene ("the exon 3*/exon 4 polynucleotide probe"). In other embodiments, the polynucleotide probe hybridizes under high stringency conditions to exon 0* of a LSAMP gene or a junction of a chimeric nucleic acid, wherein the chimeric nucleic acid comprises a first portion from exon 0* of a LSAMP gene and a second portion from exon 1 of a LSAMP gene "the exon 0*/exon 1 polynucleotide probe"). The polynucleotide probe is optionally labeled.

Another aspect is directed to a kit comprising the composition with the ZBTB20/LSAMP polynucleotide probe, the exon 3*/exon 4 polynucleotide probe, or the exon 0*/exon 1 polynucleotide probe and a second composition comprising a polynucleotide probe that hybridizes under high stringency conditions to a gene selected from COL10A1, HOXC4, ESPL1, MMP9, ABCA13, PCDHGA1, and AGSK1. The polynucleotide probe is optionally labeled. Alternatively, the kit comprises the composition with the ZBTB20/LSAMP polynucleotide probe, the exon 3*/exon 4 polynucleotide probe, or the exon 0*/exon 1 polynucleotide probe and a second composition comprising a polynucleotide probe that hybridizes under high stringency conditions to a gene selected from ERG, AMACR, PCA3, and PSA. The polynucleotide probe is optionally labeled.

Yet another aspect is directed to a composition comprising a double stranded oligonucleotide duplex, wherein the oligonucleotide duplex comprises a first nucleic acid hybridized to a second nucleic acid, wherein the first nucleic acid comprises a first portion from a ZBTB20 gene fused to a second portion from a LSAMP gene and wherein the second nucleic acid is a polynucleotide probe that is hybridized to a junction between the first portion from the ZBTB20 gene and the second portion from the LSAMP gene. In one embodiment, the first portion comprises exon 1 of the ZBTB20 gene and the second portion comprises exon 3* or exon 4 of LSAMP. In another embodiment, the first nucleic acid comprises a first portion from exon 3* of a LSAMP gene fused to a second portion from exon 4 of a LSAMP gene and wherein the second nucleic acid is a polynucleotide probe that is hybridized to a junction between the first portion from exon 3* of the LSAMP gene and the second portion from exon 4 of the LSAMP gene. In another embodiment, the first nucleic acid comprises a first portion from exon 0* of a LSAMP gene fused to a second portion from exon 1 of a LSAMP gene and wherein the second nucleic acid is a polynucleotide probe that is hybridized to a junction between the first portion from exon 0* of the LSAMP gene and the second portion from exon 4 of the LSAMP gene. The polynucleotide probe is optionally labeled.

Another aspect is directed to an isolated antibody that binds to a polypeptide encoded by a gene fusion, wherein the gene fusion has a first portion from a ZBTB20 gene and a second portion from a LSAMP gene. In one embodiment the polypeptide is a truncated LSAMP polypeptide. In another embodiment, the antibody binds to an epitope present in the polypeptide encoded by the gene fusion that is not present in either the wild type ZBTB20 protein or the wild type LSAMP protein. The antibody is optionally labeled.

Another aspect is directed to a composition for amplifying a gene fusion, wherein the gene fusion has a first portion from a ZBTB20 gene and a second portion from a LSAMP gene. In one embodiment, the first portion comprises exon 1 of the ZBTB20 gene and the second portion comprises exon 3* or exon 4 of LSAMP. In one embodiment, the composition comprises a first and a second primer, wherein the first and the second primer are capable of amplifying a nucleotide sequence from the gene fusion that spans the junction between the first portion of the gene fusion from the ZBTB20 gene and the second portion of the gene fusion from the LSAMP gene. In one embodiment, the first primer hybridizes to the first portion of the gene fusion from the ZBTB20 gene and the second primer hybridizes to the second portion of the gene fusion from the LSAMP gene.

Exon 3* of the LSAMP locus is a newly recognized LSAMP exon that arises as a result of a genomic rearrangement of the ZBTB20 and LSAMP genes. Thus, another aspect is directed to a composition for amplifying exon 3* of a LSAMP gene or a gene fusion, wherein the gene fusion has a first portion from exon 3* of a LSAMP gene and a second portion from exon 4 of a LSAMP gene. In one embodiment, the composition comprises a first and a second primer, wherein the first and the second primer are capable of amplifying a nucleotide sequence within exon 3* of LSAMP that is unique to exon 3* and is not found in other gene sequences or a nucleotide sequence from the gene fusion that spans the junction between a first portion from exon 3* of a LSAMP gene and a second portion from exon 4 of a LSAMP gene.

Exon 0* of the LSAMP locus is a newly recognized LSAMP exon that arises as a result of a genomic rearrangement of the ZBTB20 and LSAMP genes. Thus, another aspect is directed to a composition for amplifying exon 0* of a LSAMP gene or a gene fusion, wherein the gene fusion has a first portion from exon 0* of a LSAMP gene and a second portion from exon 1 of a LSAMP gene. In one embodiment, the composition comprises a first and a second primer, wherein the first and the second primer are capable of amplifying a nucleotide sequence within exon 0* of LSAMP that is unique to the 0* exon and is not found in other gene sequences or a nucleotide sequence from the gene fusion that spans the junction between a first portion from exon 0* of a LSAMP gene and a second portion from exon 1 of a LSAMP gene.

Another genomic rearrangement of interest that is associated with prostate cancer is the PTEN deletion. While the PTEN gene is a common tumor suppressor and its deletion is known to be associated with cancer, it has been surprisingly discovered that the PTEN deletion occurs with significantly different frequencies in different ethnic groups and is markedly absent in subjects of African descent. Understanding the stratification of cancer-related genomic rearrangements, such as the PTEN deletion, between different patient populations provides important information to instruct treatment options for prostate cancer patients.

Accordingly, one aspect is directed to a method of selecting a targeted prostate cancer treatment for a patient of African descent, wherein the method comprises (a) excluding prostate cancer therapy that targets the PI3K/PTEN/Akt/mTOR pathway as a treatment option; and selecting an appropriate prostate cancer treatment. In one embodiment, the method further comprises a step of testing a biological sample from the patient, wherein the biological sample comprises prostate cells to confirm that the prostate cells to do not contain a PTEN gene deletion.

BRIEF DESCRIPTION OF THE DRAWINGS

The accompanying drawings, which are incorporated in and constitute a part of this specification, illustrate certain embodiments, and together with the written description, serve to explain certain principles of the antibodies and methods disclosed herein.

FIG. 2 discloses SEQ ID NOS 49-50, respectively, in order of appearance.

Figure 1:
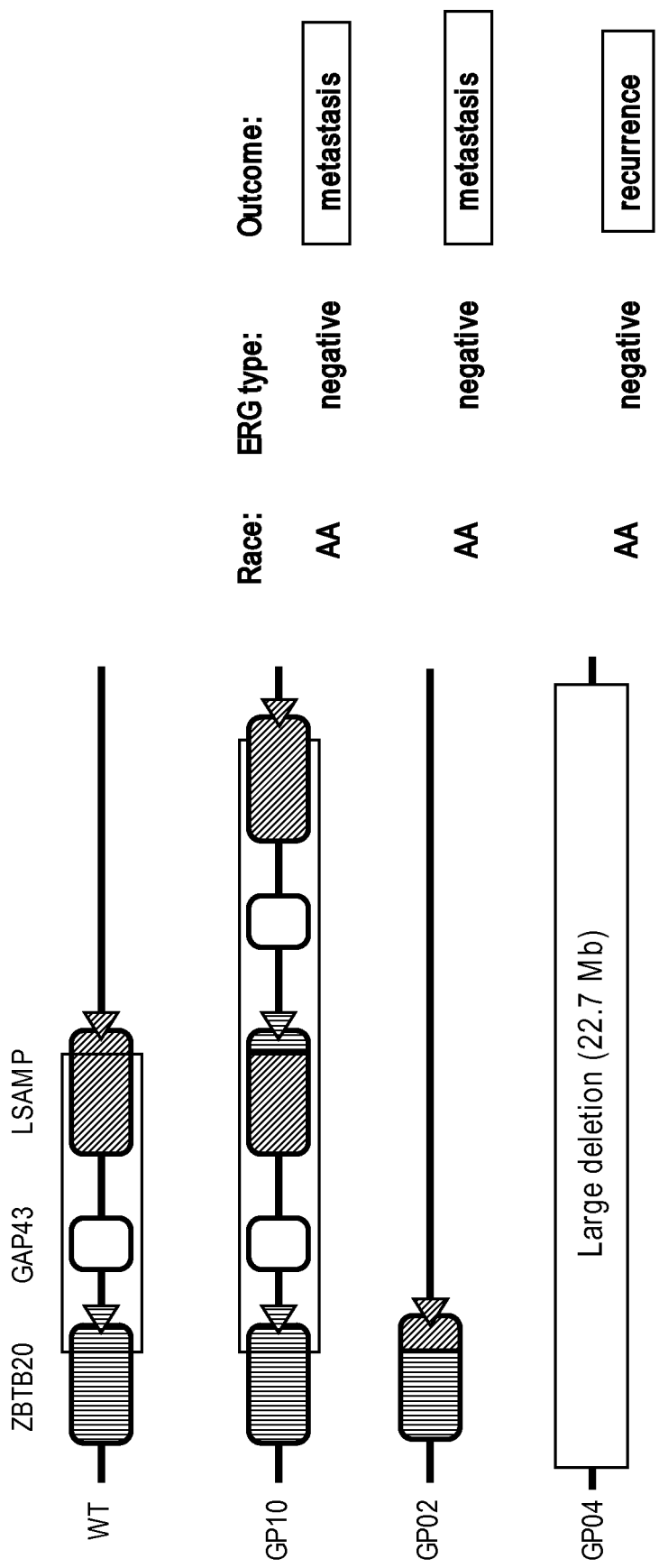
FIG. 1 is a map of the wild type chromosome region 3q13, showing the ZBTB20, GAP43, and LSAMP genes, as well genomic rearrangements of chromosome region 3q13 identified in three different AA patients, all of whom developed an aggressive form of prostate cancer.

Processor(s) 110 may further communicate via a network interface 108, which in turn may communicate via the one or more networks 104, such as the Internet or other public or private networks, such that a query or other request may be received from client 102, or other device or service. Additionally, processor(s) 110 may utilize network interface 108 to send information, instructions, workflows query partial workflows, or other data to a user via the one or more networks 104. Network interface 104 may include or be communicatively coupled to one or more servers. Client 102 may be, e.g., a personal computer coupled to the internet.

Processor(s) 110 may, in general, be programmed or configured to execute control logic and control operations to implement methods disclosed herein. Processors 110 may be further communicatively coupled (i.e., coupled by way of a communication channel) to co-processors 114. Co-processors 114 can be dedicated hardware and/or firmware components configured to execute the methods disclosed herein. Thus, the methods disclosed herein can be executed by processor 110 and/or co-processors 114.

Other configurations of computer system 106, associated network connections, and other hardware, software, and service resources are possible.

Figure 4:
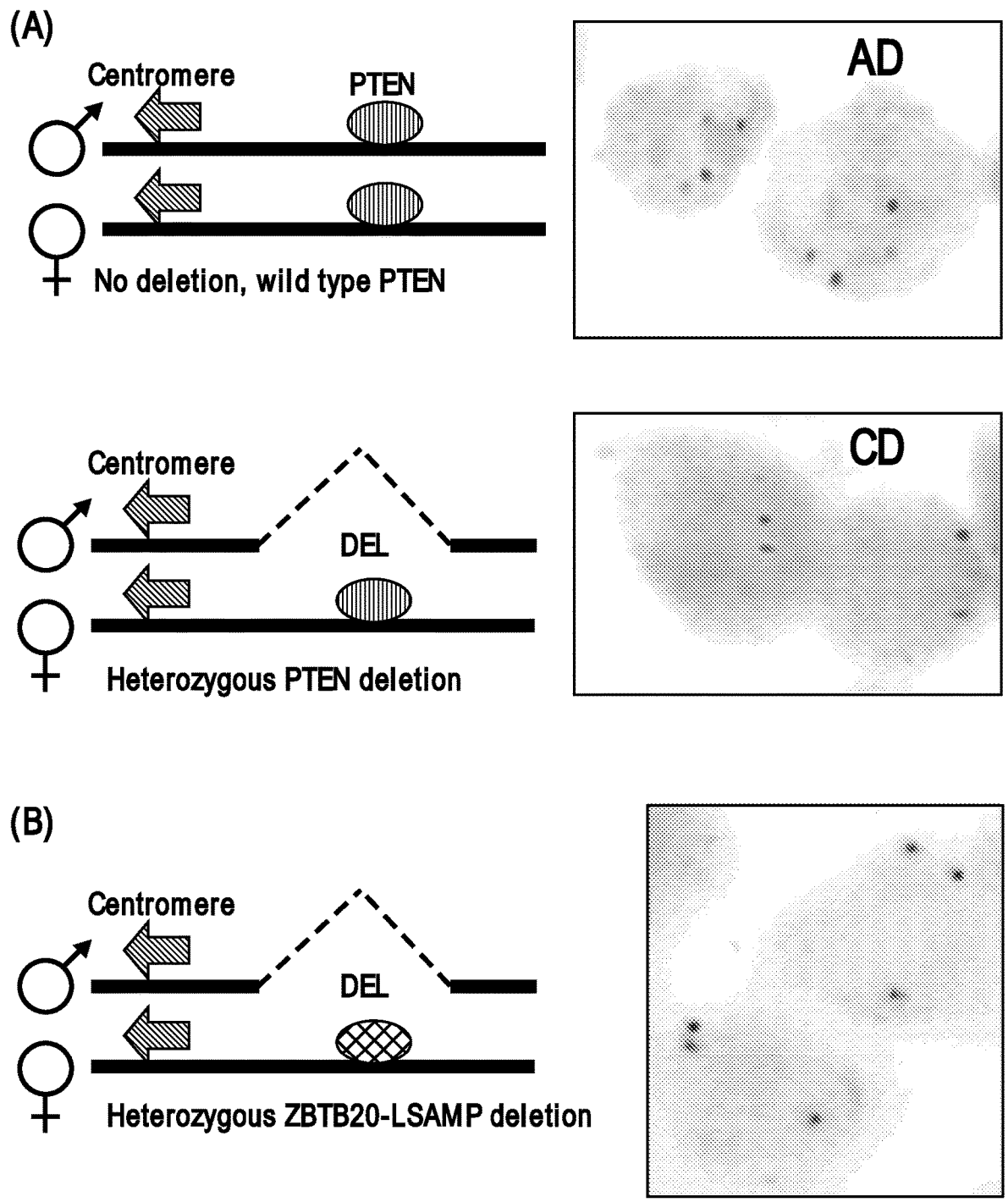

FIG. 4A shows the hybridization of two PTEN FISH probes and two chromosome 10 centromeric probes, indicating the presence of two (diploid) wild type PTEN alleles on chromosome 10 in AD CaPs. Heterozygous PTEN deletion indicated by the loss of one copy of PTEN (absence of one PTEN-specific FISH signal) in the nuclei of a CD CaP. Deletion may occur on either or both the maternal or paternal chromosomes.

FIG. 4B shows heterozygous deletion between the ZBTB20-LSAMP region indicated by the loss of one copy of the signal within the nuclei of an AD CaP. Centromeric probes detect two copies of chromosome 3.

FIG. 5 shows the exon (E) structure (in the 5' to 3' direction) of 10 different ZBTB20-LSAMP fusion transcripts and the exon structure of an alternatively spliced LSAMP (LPCS1) transcript. E1, E1A, E1B, and E1C represent four variants of exon 1 of ZBTB20. E0, E1, E2, E3, E3*, E4, E5, E6, and E7 represent the exons of LSAMP. The numbers in parentheses represent the number of nucleotides in each exon. The asterix indicates previously unannotated exon variants.

DETAILED DESCRIPTION

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "of African descent" refers to individuals who self-identify as being of African descent, including individuals who self-identify as being African-American, and individuals determined to have genetic markers correlated with African ancestry, also called Ancestry Informative Markers (AIM), such as the AIMs identified in Judith Kidd et al., Analyses of a set of 128 ancestry informative single-nucleotide polymorphisms in a global set of 119 population samples, Investigative Genetics, (2): 1, 2011, which reference is incorporated by reference in its entirety.

The term "of Caucasian descent" refers to individuals who self-identify as being of Caucasian descent, including individuals who self-identify as being Caucasian-American, and individuals determined to have genetic markers correlated with Caucasian (e.g., European, North African, or Asian (Western, Central or Southern) ancestry, also called Ancestry Informative Markers (AIM), such as the AIMs identified in Judith Kidd et al., Analyses of a set of 128 ancestry informative single-nucleotide polymorphisms in a global set of 119 population samples, Investigative Genetics, (2):1, 2011, which reference is incorporated by reference in its entirety.

The term "antibody" refers to an immunoglobulin or antigen-binding fragment thereof, and encompasses any polypeptide comprising an antigen-binding fragment or an antigen-binding domain. The term includes but is not limited to polyclonal, monoclonal, monospecific, polyspecific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Unless otherwise specified, an antibody is not necessarily from any particular source, nor is it produced by any particular method.

The terms "antigen-binding domain" and "antigen-binding fragment" refer to a part of an antibody molecule that comprises amino acids responsible for the specific binding between antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a F(ab')$_2$ fragment, a bivalent fragment having two Fab fragments linked by a disulfide bridge at the hinge region; Fv fragment: a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide (SEQ ID NO:48) may be used as a linker, but other linkers are known in the art. These antibody fragments are obtained using conventional techniques known to those with skill in the art, and the fragments are evaluated for function in the same manner as are intact antibodies.

The term "detecting" or "detection" means any of a variety of methods known in the art for determining the presence or amount of a nucleic acid or a protein. As used throughout the specification, the term "detecting" or "detection" includes either qualitative or quantitative detection.

The term "therapeutically effective amount" refers to a dosage or amount that is sufficient for treating an indicated disease or condition.

The term "gene expression profile" refers to the expression levels of a plurality of genes in a sample. As is understood in the art, the expression level of a gene can be analyzed by measuring the expression of a nucleic acid (e.g., genomic DNA or mRNA) or a polypeptide that is encoded by the nucleic acid.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived.

The terms "polypeptide," "peptide," and "protein" are used interchangeably herein to refer to polymers of amino acids.

The term "polypeptide probe" as used herein refers to a labeled (e.g., isotopically labeled) polypeptide that can be used in a protein detection assay (e.g., mass spectrometry) to quantify a polypeptide of interest in a biological sample.

The term "primer" means a polynucleotide capable of binding to a region of a target nucleic acid, or its complement, and promoting nucleic acid amplification of the target nucleic acid. Generally, a primer will have a free 3' end that can be extended by a nucleic acid polymerase. Primers also generally include a base sequence capable of hybridizing via complementary base interactions either directly with at least one strand of the target nucleic acid or with a strand that is complementary to the target sequence. A primer may comprise target-specific sequences and optionally other sequences that are non-complementary to the target sequence. These non-complementary sequences may comprise, for example, a promoter sequence or a restriction endonuclease recognition site.

A "variation" or "variant" refers to an allele sequence that is different from the reference at as little as a single base or for a longer interval.

The term "genomic rearrangement of the ZBTB20 and LSAMP genes" and the like refers to any rearrangement of the ZBTB20 and LSAMP genes that is associated with prostate cancer and can include a gene fusion between the ZBTB20 gene and the LSAMP gene, a gene inversion involving the ZBTB20 gene and the LSAMP gene, a gene deletion involving the ZBTB20 and LSAMP genes (or a portion of one or both genes), or a gene duplication involving the ZBTB20 and LSAMP genes.

The term "ERG" or "ERG gene" refers to Ets-related gene (ERG), which has been assigned the unique Hugo Gene Nomenclature Committee (HGNC) identifier code: HGNC: 3446, and includes ERG gene fusion products that are prevalent in prostate cancer, including TMPRSS2-ERG fusion products. Analyzing the expression of ERG or the ERG gene includes analyzing the expression of ERG gene fusion products that are associated with prostate cancer, such as TMPRSS2-ERG.

As used herein, the term "aggressive form of prostate cancer" refers to prostate cancer with a primary Gleason score of 4 or 5 (also known as "poorly differentiated" prostate cancer or prostate cancer that has metastasized or has recurred following prostatectomy).

As used herein, the term "Gleason 6-7" refers to Gleason grade 3+3 and 3+4. It is also referred to in the art as primary pattern 3 or primary Gleason pattern 3.

ZBTB20/LSAMP Genomic Rearrangement

Next generation sequencing techniques were used to identify new biomarkers and therapeutic targets for CaP. High quality genome sequence data and coverage obtained from histologically defined and precisely dissected primary CaP specimens (80-95% tumor, primary Gleason pattern 3) was compared between cohorts of 7 patients of Caucasian descent and 7 patients of African descent (28 samples total including matched controls from each patient) to evaluate the observed disparities of CaP incidence and mortality between the two ethnic groups. These data and analyses provide the first evaluation of prostate cancer genomes from CaP patients of African descent ("AD") and Caucasian descent ("CD") that have been matched for clinic-pathologic features.

Whole genome sequence analysis of these prostate cancer samples identified a novel genomic rearrangement between the ZBTB20 (zinc finger and BTB containing 20) and LSAMP (limbic system associated membrane protein) genes. Four of the 7 samples from subjects of African descent were negative for the TMPRSS2/ERG fusion, the most prevalent gene fusion identified to date in prostate cancer. The ZBTB20-LSAMP region was rearranged or deleted in three of the four TMPRSS2/ERG negative samples from subjects of African descent. All three of the ZBTB20/LSAMP positive, TMPRSS2/ERG negative subjects developed an aggressive form of prostate cancer, with two experiencing metastasis and one developing recurrence, suggesting that the ZBTB20/LSAMP genomic rearrangement is an indicator of a more aggressive prostate cancer phenotype, particularly in patients who do not express the TMPRSS2/ERG fusion. As patients of AD express the TMPRSS2/ERG fusion at lower frequencies than patients of CD, the genomic rearrangement of the ZBTB20 and LSAMP genes, may represent a particularly useful biomarker for detecting a more aggressive prostate cancer phenotype in patients of AD.

The unique identifier code assigned by HGNC for the LSAMP gene is HGNC:6705. The Entrez Gene code for LSAMP is 4045. The nucleotide and amino acid sequences of LSAMP are known and represented by the NCBI Reference Sequence NM_002338.3, GI:257467557 (SEQ ID NO:9 and SEQ ID NO:10), which sequences are incorporated by reference in their entirety. The chromosomal location of the LSAMP gene is 3q13.2-q21. The LSAMP gene encodes a neuronal surface glycoprotein found in cortical and subcortical regions of the limbic system. LSAMP has been reported as a tumor suppressor gene (Baroy et al., 2014, Mol Cancer 28; 13:93). For example, Kuhn et al. reported a recurrent deletion in chromosome region 3q13.31, which contains the LSAMP gene, in a subset of core binding factor acute myeloid leukemia [29]. In osteosarcoma, chromosome region 3q13.31 was identified as the most altered genomic region, with most alterations taking the form of a deletion, including, in certain instances, deletion of a region that contains the LSAMP gene [30]. A chromosomal translocation (t1; 3) with a breakpoint involving the NORE1 gene of chromosome region 1 q32.1 and the LSAMP gene of chromosome region 3q13.3 was identified in clear cell renal carcinomas [31]. A chromosomal translocation in epithelial ovarian carcinoma has also been identified [32]. Although single nucleotide variations of LSAMP has been shown to be a significant predictor of prostate cancer-specific mortality [33], genomic rearrangement of LSAMP has never been reported in prostate cancer and has never been described as a fusion with ZBTB20 in any type of cancer.

The unique identifier code assigned by HGNC for the ZBTB20 gene is HGNC:13503. The Entrez Gene code for ZBTB20 is 26137. ZBTB20 is a DNA binding protein and is believed to be a transcription factor. There are at least 7 alternative transcript variants. There are at least four distinct promoters that can initiate transcription from at least four distinct sites within the ZBTB20 locus, producing four variants of exon 1 of ZBTB20: E1, E1A, E1B, and E1C. Representative nucleotide and amino acid sequences of ZBTB20 variant 1 are known and represented by the NCBI Reference Sequence NM_001164342.1 GI:257900532 (SEQ ID NO:11 and SEQ ID NO:12), which sequences are incorporated by reference in their entirety. Variant 2 differs from variant 1 in the 5' untranslated region, lacks a portion of the 5' coding region, and initiates translation at a downstream start codon, compared to variant 1. The encoded isoform (2) has a shorter N-terminus compared to isoform 1. Variants 2-7 encode the same isoform (2). Representative nucleotide and amino acid sequences of ZBTB20 variant 2 are known and represented by the NCBI Reference Sequence NM_015642.4, GI:257900536 (SEQ ID NO:13 and SEQ ID NO:14), which sequences are incorporated by reference in their entirety. The chromosomal location of the ZBTB20 gene is 3q13.2.

Certain embodiments are directed to a method of collecting data for use in diagnosing or prognosing CaP, the method comprising detecting in a biological sample comprising prostate cells (or nucleic acid or polypeptides isolated from prostate cells) a genomic rearrangement of the ZBTB20 and LSAMP genes. The method may optionally include an additional step of diagnosing or prognosing CaP using the collected gene expression data. In one embodiment, detecting a genomic rearrangement of the ZBTB20 and LSAMP genes indicates the presence of CaP in the biological sample or an increased likelihood of developing CaP. In another embodiment detecting a genomic rearrangement of the ZBTB20 and LSAMP genes indicates the presence of an aggressive form of CaP in the biological sample or an increased likelihood of developing an aggressive form of CaP.

In one embodiment, the genomic rearrangement comprises a gene fusion between the ZBTB20 gene and the LSAMP gene, such as a fusion between exon 1 (e.g., E1, E1A, E1B, or E1C) of the ZBTB20 gene and exon 4 of the LSAMP gene. In another embodiment, the genomic rearrangement comprises a gene inversion involving the ZBTB20 gene and the LSAMP gene. In another embodiment, the genomic rearrangement comprises a deletion in chromosome region 3q13, wherein the deletion spans both the ZBTB20 and LSAMP genes (or a portion of one or both genes). In yet another embodiment, the genomic rearrangement comprises a gene duplication involving the ZBTB20 and LSAMP genes.

The methods of collecting data or diagnosing and/or prognosing CaP may further comprise detecting expression of other genes associated with prostate cancer, including, but not limited to COL10A1, HOXC4, ESPL1, MMP9, ABCA13, PCDHGA1, and AGSK1. The unique identifier codes assigned by HGNC and Entrez Gene for these genes that are more frequently overexpressed in patients of African descent and the accession number of representative sequences are provided in Table 1, which sequences are hereby incorporated by reference in their entirety.

TABLE 1

| Gene | HGNC ID | Entrez Gene ID | NCBI Reference | SEQ ID NOs. |
|---|---|---|---|---|
| COL10A1 | 2185 | 1300 | NM_000493.3 GI:98985802 | 17 and 18 |
| HOXC4 | 5126 | 3221 | NM_014620.5 GI:546232084 | 19 and 20 |
| ESPL1 | 16856 | 9700 | NM_012291.4 GI:134276942 | 21 and 22 |
| MMP9 | 7176 | 4318 | NM_004994.2 GI:74272286 | 23 and 24 |
| ABCA13 | 14638 | 154664 | AY204751.1 GI:30089663 | 25 and 26 |
| PCDHGA1 | 8696 | 56114 | NM_018912.2 GI:14196453 | 27 and 28 |
| AGSK1 | N/A | 80154 | NR_026811 GI:536293433 NR_033936.3 GI:536293365 NR_103496.2 GI:536293435 | 29-31 |

In another embodiment, the methods of collecting data or diagnosing and/or prognosing CaP may further comprise detecting expression of other genes associated with prostate cancer, including, but not limited to ERG, PSA, and PCA3.

PTEN Deletion

PTEN (phosphatase and tensin homolog) is a known tumor suppressor gene that is mutated in a large number of cancers at high frequency. The protein encoded by this gene is a phosphatidylinositol-3,4,5-trisphosphate 3-phosphatase. It contains a tensin like domain as well as a catalytic domain similar to that of the dual specificity protein tyrosine phosphatases. Unlike most of the protein tyrosine phosphatases, PTEN preferentially dephosphorylates phosphoinositide substrates. It negatively regulates intracellular levels of phosphatidylinositol-3,4,5-trisphosphate in cells and functions as a tumor suppressor by negatively regulating AKT/PKB signaling pathway. Activation of growth factor receptors by binding of a growth factor to its receptor or by mutation of the growth factor receptor leads to activation of the PI3K/PTEN/Akt/mTOR cascade, which, among other things, leads to the activation of certain transcription factors [28], which reference is hereby incorporated by reference in its entirety. PTEN normally acts to down regulate this pathway. Thus, in cancers that contain a PTEN gene deletion, the expression of the Akt gene and activation of mTOR is frequently increased.

The unique identifier codes assigned by HGNC and Entrez Gene for the PTEN gene are HGNC:9588 and Entrez Gene:5728, respectively. The accession number of representative PTEN nucleic acid and polypeptide sequences is NM_000314.4, GI:257467557 (SEQ ID NO:15 and SEQ ID NO: 16), which sequences are incorporated by reference in their entirety. The chromosomal location of the PTEN gene is 10q23.

Whole genome sequence analysis of CD and AD prostate cancer samples disclosed a significant disparity between the genomic rearrangement of the PTEN locus in the different ethnic groups. More specifically, PTEN deletion was detected only in patients of Caucasian descent. Additional FISH analysis in a tissue microarray confirmed that PTEN deletion is an infrequent event in the development of prostate cancer in AD men as compared to CD men.

Accordingly, one aspect is directed to using this discovery about the disparity in the PTEN deletion across ethnic groups to make informed decisions about treatment options available to a subject who has prostate cancer. In particular, given the disclosed disparity in the PTEN deletion in prostate cancer from patients of Caucasian and African descent, as a general rule, prostate cancer therapies that target the PI3K/PTEN/Akt/mTOR pathway [28] should not be selected for patients of African descent. Or, at a minimum, a prostate cancer therapy that targets the PI3K/PTEN/Akt/mTOR pathway [28] should not be considered for a patient of African descent unless it is first confirmed by genetic testing that prostate cells from the patient contain the PTEN deletion. As such, one embodiment is directed to a method of selecting a targeted prostate cancer treatment for a patient of African descent, wherein the method comprises excluding a prostate cancer therapy that targets the PI3K/PTEN/Akt/mTOR pathway [28] as a treatment option; and selecting an appropriate prostate cancer treatment. In one embodiment, the method further comprises a step of testing a biological sample from the patient, wherein the biological sample comprises prostate cells to confirm that the prostate cells to do not contain a PTEN gene deletion.

There are various inhibitors that target the PI3K/PTEN/Akt/mTOR pathway, including PI3K inhibitors, Akt inhibitors, mTOR inhibitors, and dual PI3K/mTOR inhibitors. PI3K inhibitors include, but are not limited to LY-294002, wortmannin, PX-866, GDC-0941, CAL-10, XL-147, XL-756, IC87114, NVP-BKM120, and NVP-BYL719. Akt inhibitors include, but are not limited to, A-443654, GSK690693, VQD-002 (a.k.a. API-2, triciribine), KP372-1, KRX-0401 (perifosine), MK-2206, GSK2141795, LY317615 (enzasturin), erucylphosphocholine (ErPC), erucylphosphohomocholine (ErPC3), PBI-05204, RX-0201, and XL-418. mTOR inhibitors include, but are not limited to, rapamycin, modified rapamycins (rapalogs, e.g., CCI-779, afinitor, torisel, temsirolimus), AP-23573 (ridaforolimus), and RAD001 (afinitor, everolimus), metformin, OSI-027, PP-242, AZD8055, AZD2014, palomid 529, WAY600, WYE353, WYE687, WYE132, Ku0063794, and OXA-01. Dual PI3K/mTOR inhibitors include, but are not limited to, P1-103, NVP-BEZ235, PKI-587, PKI-402, PF-04691502, XL765, GNE-477, GSK2126458, and WJD008.

Detecting ZBTB20/LSAMP or PTEN Deletion

Measuring or detecting the expression of a genomic rearrangement of the ZBTB20 and LSAMP genes in the methods described herein comprises measuring or detecting any nucleic acid transcript (e.g., mRNA, cDNA, or genomic DNA) thereof or any protein encoded by such a nucleic acid transcript. Thus, in one embodiment, detecting the presence of the ZBTB20/LSAMP genomic rearrangement in the biological sample comprises detecting a chromosomal rearrangement of genomic DNA having a first portion from the ZBTB20 gene and a second portion from the LSAMP gene. In one embodiment, the chromosomal rearrangement gives rise to a fusion between exon 1 (e.g., E1, E1A, E1B, or E1C) of the ZBTB20 gene and exon3* or exon 4 of the LSAMP gene. In one embodiment, the chromosomal rearrangement comprises the nucleotide sequence of SEQ ID NO:1.

In another embodiment, the chromosomal rearrangement results in the deletion of the ZBTB20 and LSAMP genes. Thus, in one embodiment, detecting the presence of the ZBTB20/LSAMP genomic rearrangement in the biological sample comprises detecting a deletion in chromosome region 3q13, wherein the deletion spans the ZBTB20 and LSAMP genes.

In another embodiment, detecting the presence of the ZBTB20/LSAMP genomic rearrangement in the biological sample comprises detecting a chimeric mRNA or cDNA transcript having a first nucleic acid portion from the ZBTB20 gene and a second nucleic acid portion from the LSAMP gene. In one embodiment, the chimeric mRNA or cDNA transcript comprises a fusion between exon 1 (e.g., E1, E1A, E1B, or E1C) of the ZBTB20 gene and exon 4 of the LSAMP gene. For example, the chimeric mRNA or cDNA transcript may comprise the nucleotide sequence of SEQ ID NO:4, SEQ ID NO:32, SEQ ID NO:34, SEQ ID NO:35, SEQ ID NO:36, SEQ ID NO:37, SEQ ID NO:38, or SEQ ID NO:40. In another embodiment, the chimeric mRNA or cDNA transcript comprises a fusion between exon 1 (e.g., E1, E1A, E1B, or E1C) of the ZBTB20 gene and exon 3* of the LSAMP gene. For example, the chimeric mRNA or cDNA transcript may comprise the nucleotide sequence of SEQ ID NO:33, SEQ ID NO:39, or SEQ ID NO:41.

Exon 3* (SEQ ID NO:45) represents a novel exon sequence from the LSAMP locus that has not been previously annotated and has now been shown to arise following genomic rearrangement of the ZBTB20 and LSAMP genes. Therefore, detecting the presence of the ZBTB20/LSAMP genomic rearrangement in the biological sample may comprise detecting a mRNA or cDNA transcript corresponding to a region of exon 3* that is not present in other genes and, thus, can be used to positively identify exon 3* of the LSAMP gene. Alternatively, detecting the presence of the ZBTB20/LSAMP genomic rearrangement in the biological sample may comprise detecting a mRNA or cDNA transcript comprising exon 3* and exon 4 of the LSAMP gene or a portion thereof that spans the junction between exon 3* and exon 4 of LSAMP and is not present in other genes and, thus, can be used to positively identify the transcript as coming from a fusion of exon 3* and exon 4 of LSAMP.

Exon 0* (SEQ ID NO:47) represents a novel exon sequence from the LSAMP locus that has not been previously annotated and was identified in an alternatively spliced transcript in a patient having a genomic rearrangement of the ZBTB20 and LSAMP genes. Therefore, detecting the presence of the ZBTB20/LSAMP genomic rearrangement in the biological sample may comprise detecting a mRNA or cDNA transcript corresponding to a region of exon 0* that is not present in other genes and, thus, can be used to positively identify exon 0* of the LSAMP gene. Alternatively, detecting the presence of the ZBTB20/LSAMP genomic rearrangement in the biological sample may comprise detecting a mRNA or cDNA transcript comprising exon 0* and exon 1 of the LSAMP gene or a portion thereof that spans the junction between exon 0* and exon 1 of the LSAMP gene and is not present in other genes and, thus, can be used to positively identify the transcript as coming from a fusion of exon 0* and exon 1 of LSAMP.

The expression of the ZBTB20/LSAMP genomic rearrangement can be measured or detected by measuring or detecting one or more of the genomic sequences or mRNA/cDNA transcripts corresponding to the genomic rearrangement of the genes, or to all of the genomic sequences or mRNA/cDNA transcripts associated with the genomic rearrangement of the ZBTB20 and LSAMP genes.

Detecting a deletion in the PTEN gene comprises detecting a deletion in chromosome region 10q23, wherein the deletion spans the PTEN gene or a portion thereof. The PTEN deletion can be measured or detected by measuring or detecting one or more of the genomic sequences or mRNA/cDNA transcripts corresponding to the PTEN deletion, or to all of the genomic sequences or mRNA/cDNA transcripts associated with the PTEN gene.

Chromosomal rearrangements can be detected using known techniques. For example, fluorescent in situ hybridization (FISH) analysis can be used to detect chromosomal rearrangements. In these embodiments, nucleic acid probes that hybridize under conditions of high stringency to the chromosomal rearrangement, such as the ZBTB20/LSAMP chromosomal rearrangement or PTEN deletion, are incubated with a biological sample comprising prostate cells (or nucleic acid obtained therefrom). Other known in situ hybridization techniques can be used to detect chromosomal rearrangements, such as ZBTB20/LSAMP or the PTEN deletion. The nucleic acid probes (DNA or RNA) can hybridize to DNA or mRNA and can be designed to detect genomic rearrangements in the ZBTB20 and LSAMP genes or the PTEN gene, such as gene fusion events, amplifications, deletions, or mutations.

Typically, gene expression can be detected or measured on the basis of mRNA or cDNA levels, although protein levels also can be used when appropriate. Any quantitative or qualitative method for measuring mRNA levels, cDNA, or protein levels can be used. Suitable methods of detecting or measuring mRNA or cDNA levels include, for example, Northern Blotting, RNAse protection assays, microarray analysis, or a nucleic acid amplification procedure, such as reverse-transcription PCR (RT-PCR) or real-time RT-PCR, also known as quantitative RT-PCR (qRT-PCR). Such methods are well known in the art. See e.g., Sambrook et al., Molecular Cloning: A Laboratory Manual, 4$^{th}$ Ed., Cold Spring Harbor Press, Cold Spring Harbor, N.Y., 2012. Other techniques include digital, multiplexed analysis of gene expression, such as the nCounter® (NanoString Technologies, Seattle, Wash.) gene expression assays, which are further described in [22], [23], US20100112710 and US20100047924, all of which are hereby incorporated by reference in their entirety.

Detecting a nucleic acid of interest generally involves hybridization between a target (e.g. mRNA, cDNA, or genomic DNA) and a probe. One of skill in the art can readily design hybridization probes for detecting the genomic rearrangement of the ZBTB20 and LSAMP genes or deletion of the PTEN gene. See e.g., Sambrook et al., Molecular Cloning: A Laboratory Manual, 4$^{th}$ Ed., Cold Spring Harbor Press, Cold Spring Harbor, N.Y., 2012. Each probe should be substantially specific for its target, to avoid any cross-hybridization and false positives. An alternative to using specific probes is to use specific reagents when deriving materials from transcripts (e.g., during cDNA production, or using target-specific primers during amplification). In both cases specificity can be achieved by hybridization to portions of the targets that are substantially unique within the group of genes being analyzed, e.g. hybridization to the polyA tail would not provide specificity. If a target has multiple splice variants, it is possible to design a hybridization reagent that recognizes a region common to each variant and/or to use more than one reagent, each of which may recognize one or more variants.

Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions," as defined herein, are identified by, but not limited to, those that: (1) use low ionic strength and high temperature for washing, for example 0.015 M sodium chloride/0.0015 M sodium citrate/0.1% sodium dodecyl sulfate at 50° C.; (2) use during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) use 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In certain embodiments, microarray analysis or a PCR-based method is used. In this respect, measuring the expression of the genomic rearrangement of the ZBTB20 and LSAMP genes or PTEN deletion in prostate cancer cells can comprise, for instance, contacting a sample containing or suspected of containing prostate cancer cells with polynucleotide probes specific to the ZBTB20/LSAMP genomic rearrangement or PTEN deletion, or with primers designed to amplify a portion of the ZBTB20/LSAMP or PTEN genomic rearrangement, and detecting binding of the probes to the nucleic acid targets or amplification of the nucleic acids, respectively. Detailed protocols for designing PCR primers are known in the art. See e.g., Sambrook et al., Molecular Cloning: A Laboratory Manual, 4$^{th}$ Ed., Cold Spring Harbor Press, Cold Spring Harbor, N.Y., 2012. Similarly, detailed protocols for preparing and using microarrays to analyze gene expression are known in the art and described herein.

Thus, one aspect is directed to a method of determining if a biological sample comprising nucleic acid contains a gene fusion, where the gene fusion has a first portion from a ZBTB20 gene and a second portion from a LSAMP gene, the method comprising:

combining the biological sample with at least a first and a second polynucleotide primer under hybridizing conditions, wherein the first polynucleotide primer comprises a sequence that hybridizes to the first portion of the gene fusion from the ZBTB20 gene (e.g., exon 1), and the second polynucleotide primer comprises a sequence that hybridizes to the second portion of the gene fusion from the LSAMP gene (e.g., exon 3* or exon 4), wherein the first and second polynucleotide primers are capable of amplifying a target sequence from the gene fusion that spans the junction between the first portion of the gene fusion from the ZBTB20 gene and the second portion of the gene fusion from the LSAMP gene;

adding a polymerase activity under conditions that allow for the amplification of the target sequence and production of an amplification product that comprises the target sequence if the gene fusion is present in the biological sample; and determining whether the biological sample contains the gene fusion based on the presence or absence of the amplification product.

Another aspect is directed to a method of determining if a biological sample comprising nucleic acid contains an mRNA or cDNA sequence corresponding to a region of exon 3* that is not present in other genes or a gene fusion where the gene fusion has a first portion from exon 3* of the LSAMP gene and a second portion from exon 4 of the LSAMP gene, the method comprising:

combining the biological sample with at least a first and a second polynucleotide primer under hybridizing conditions, (a) wherein the first polynucleotide primer comprises a sequence that hybridizes to a first region of exon 3* and the second polynucleotide primer comprises a sequence that hybridizes to a second region of exon 3*, wherein the first and second polynucleotide primers are capable of amplifying a target sequence from exon 3* that is unique to exon 3* of the LSAMP gene; or (b) wherein the first polynucleotide primer comprises a sequence that hybridizes to the first portion of the gene fusion from exon 3* and the second polynucleotide primer comprises a sequence that hybridizes to the second portion of the gene fusion from exon 4 of the LSAMP gene, wherein the first and second polynucleotide primers are capable of amplifying a target sequence from the gene fusion that spans the junction between the first portion of the gene fusion from exon 3* of the LSAMP gene and the second portion of the gene fusion from exon 4 of the LSAMP gene;

adding a polymerase activity under conditions that allow for the amplification of the target sequence and production of an amplification product that comprises the target sequence if the gene fusion is present in the biological sample; and determining whether the biological sample contains the mRNA or cDNA sequence corresponding to a region of exon 3* that is not present in other genes or the gene fusion based on the presence or absence of the amplification product.

Another aspect is directed to a method of determining if a biological sample comprising nucleic acid contains an mRNA or cDNA sequence corresponding to a region of exon 0* of the LSAMP gene that is not present in other genes or a gene fusion where the gene fusion has a first portion from exon 0* of the LSAMP gene and a second portion from exon 1 of the LSAMP gene, the method comprising:

combining the biological sample with at least a first and a second polynucleotide primer under hybridizing conditions, (a) wherein the first polynucleotide primer comprises a sequence that hybridizes to a first region of exon 0* and the second polynucleotide primer comprises a sequence that hybridizes to a second region of exon 0*, wherein the first and second polynucleotide primers are capable of amplifying a target sequence from exon 0* that is unique to exon 0* of the LSAMP gene; or (b) wherein the first polynucleotide primer comprises a sequence that hybridizes to the first portion of the gene fusion from exon 0* and the second polynucleotide primer comprises a sequence that hybridizes to the second portion of the gene fusion from exon 1 of the LSAMP gene, wherein the first and second polynucleotide primers are capable of amplifying a target sequence from the gene fusion that spans the junction between the first portion of the gene fusion from exon 0* of the LSAMP gene and the second portion of the gene fusion from exon 1 of the LSAMP gene;

adding a polymerase activity under conditions that allow for the amplification of the target sequence and production of an amplification product that comprises the target sequence if the gene fusion is present in the biological sample; and determining whether the biological sample contains the mRNA or cDNA sequence corresponding to a region of exon 0* that is not present in other genes or the gene fusion based on the presence or absence of the amplification product.

Alternatively or additionally, expression levels of the ZBTB20/LSAMP genomic rearrangement can be determined at the protein level, meaning that when the ZBTB20/LSAMP genomic rearrangement results in a truncated LSAMP protein or a chimeric ZBTB20/LSAMP protein, the levels of such proteins encoded by the ZBTB20/LSAMP genomic rearrangement are measured. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; 5,458,852; and 5,480,792, each of which is hereby incorporated by reference in its entirety. These assays include various sandwich, competitive, or non-competitive assay formats, to generate a signal that is related to the presence or amount of a protein of interest. Any suitable immunoassay may be utilized, for example, lateral flow, enzyme-linked immunoassays (ELISA), radioimmunoassays (RIAs), competitive binding assays, and the like. Numerous formats for antibody arrays have been described. Such arrays typically include different antibodies having specificity for different proteins intended to be detected. For example, at least 100 different antibodies are used to detect 100 different protein targets, each antibody being specific for one target. Other ligands having specificity for a particular protein target can also be used, such as the synthetic antibodies disclosed in WO/2008/048970, which is hereby incorporated by reference in its entirety. Other compounds with a desired binding specificity can be selected from random libraries of peptides or small molecules. U.S. Pat. No. 5,922,615, which is hereby incorporated by reference in its entirety, describes a device that uses multiple discrete zones of immobilized antibodies on membranes to detect multiple target antigens in an array. Microtiter plates or automation can be used to facilitate detection of large numbers of different proteins.

One type of immunoassay, called nucleic acid detection immunoassay (NADIA), combines the specificity of protein antigen detection by immunoassay with the sensitivity and precision of the polymerase chain reaction (PCR). This amplified DNA-immunoassay approach is similar to that of an enzyme immunoassay, involving antibody binding reactions and intermediate washing steps, except the enzyme label is replaced by a strand of DNA and detected by an amplification reaction using an amplification technique, such as PCR. Exemplary NADIA techniques are described in U.S. Pat. No. 5,665,539 and published U.S. Application 2008/0131883, both of which are hereby incorporated by reference in their entirety. Briefly, NADIA uses a first (reporter) antibody that is specific for the protein of interest and labelled with an assay-specific nucleic acid. The presence of the nucleic acid does not interfere with the binding of the antibody, nor does the antibody interfere with the nucleic acid amplification and detection. Typically, a second (capturing) antibody that is specific for a different epitope on the protein of interest is coated onto a solid phase (e.g., paramagnetic particles). The reporter antibody/nucleic acid conjugate is reacted with sample in a microtiter plate to form a first immune complex with the target antigen. The immune complex is then captured onto the solid phase particles coated with the capture antibody, forming an insoluble sandwich immune complex. The microparticles are washed to remove excess, unbound reporter antibody/nucleic acid conjugate. The bound nucleic acid label is then detected by subjecting the suspended particles to an amplification reaction (e.g. PCR) and monitoring the amplified nucleic acid product.

Although immunoassays have typically been used for the identification and quantification of proteins, recent advances in mass spectrometry (MS) techniques have led to the development of sensitive, high throughput MS protein analyses. The MS methods can be used to detect low concentrations of proteins in complex biological samples. For example, it is possible to perform targeted MS by fractionating the biological sample prior to MS analysis. Common techniques for carrying out such fractionation prior to MS analysis include two-dimensional electrophoresis, liquid chromatography, and capillary electrophoresis [25], which reference is hereby incorporated by reference in its entirety. Selected reaction monitoring (SRM), also known as multiple reaction monitoring (MRM), has also emerged as a useful high throughput MS-based technique for quantifying targeted proteins in complex biological samples, including prostate cancer biomarkers that are encoded by gene fusions (e.g., TMPRSS2/ERG) [26, 27], which references are hereby incorporated by reference in their entirety.

Samples

The methods described in this application involve analysis of the genomic rearrangement of the ZBTB20 and LSAMP genes or PTEN gene in cells, including prostate cells. These prostate cells are found in a biological sample, such as prostate tissue, blood, serum, plasma, urine, saliva, or prostatic fluid. Nucleic acids or polypeptides may be isolated from the cells prior to detecting gene expression.

In one embodiment, the biological sample comprises prostate tissue and is obtained through a biopsy, such as a transrectal or transperineal biopsy. In another embodiment, the biological sample is urine. Urine samples may be collected following a digital rectal examination (DRE) or a prostate biopsy. In another embodiment, the sample is blood, serum, or plasma, and contains circulating tumor cells that have detached from a primary tumor. The sample may also contain tumor-derived exosomes. Exosomes are small (typically 30 to 100 nm) membrane-bound particles that are released from normal, diseased, and neoplastic cells and are present in blood and other bodily fluids. The methods disclosed in this application can be used with samples collected from a variety of mammals, but preferably with samples obtained from a human subject.

Prostate Cancer

This application discloses certain chromosomal rearrangements between the ZBTB20 and LSAMP genes that are associated with prostate cancer. Detecting a ZBTB20/LSAMP genomic rearrangement in a biological sample can be used to identify cancer cells, such as prostate cancer cells, in a sample or to measure the severity or aggressiveness of prostate cancer, for example, distinguishing between well differentiated prostate (WD) cancer and poorly differentiated (PD) prostate cancer and/or identifying prostate cancer that has metastasized or recurred following prostatectomy or is more likely to metastasize or recur following prostatectomy. This application also discloses that deletion of the tumor suppressor gene, PTEN, occurs predominately, if not exclusively in subjects of Caucasian descent. Conversely, the PTEN deletion is an infrequent event in prostate cancer from subjects of African descent (AD), particularly in Gleason 6-7 prostate cancer from AD subjects. Of note, Gleason 6-7 (also called primary pattern 3) CaP represents the most commonly diagnosed form of CaPs in the PSA screened patient population.

When prostate cancer is found in a biopsy, it is typically graded to estimate how quickly it is likely to grow and spread. The most commonly used prostate cancer grading system, called Gleason grading, evaluates prostate cancer cells on a scale of 1 to 5, based on their pattern when viewed under a microscope.

Cancer cells that still resemble healthy prostate cells have uniform patterns with well-defined boundaries and are considered well differentiated (Gleason grades 1 and 2). The more closely the cancer cells resemble prostate tissue, the more the cells will behave like normal prostate tissue and the less aggressive the cancer. Gleason grade 3, the most common grade, shows cells that are moderately differentiated, that is, still somewhat well-differentiated, but with boundaries that are not as well-defined. Poorly-differentiated cancer cells have random patterns with poorly defined boundaries and no longer resemble prostate tissue (Gleason grades 4 and 5), indicating a more aggressive cancer.

Prostate cancers often have areas with different grades. A combined Gleason score is determined by adding the grades from the two most common cancer cell patterns within the tumor. For example, if the most common pattern is grade 4 and the second most common pattern is grade 3, then the combined Gleason score is 4+3=7. If there is only one pattern within the tumor, the combined Gleason score can be as low as 1+1=2 or as high as 5+5=10. Combined scores of 2 to 4 are considered well-differentiated, scores of 5 to 6 are considered moderately-differentiated and scores of 7 to 10 are considered poorly-differentiated. Cancers with a high Gleason score are more likely to have already spread beyond the prostate gland (metastasized) at the time they were found.

In general, the lower the Gleason score, the less aggressive the cancer and the better the prognosis (outlook for cure or long-term survival). The higher the Gleason score, the more aggressive the cancer and the poorer the prognosis for long-term, metastasis-free survival.

Patient Treatment

This application describes methods of diagnosing and prognosing prostate cancer in a sample obtained from a subject, in which gene expression in prostate cells and/or tissues are analyzed. If a sample shows expression of a genomic rearrangement of the ZBTB20 and LSAMP genes, then there is an increased likelihood that the subject has prostate cancer or a more advanced/aggressive form (e.g., PD prostate cancer) of prostate cancer. In the event of such a result, the methods of detecting or prognosing prostate cancer may include one or more of the following steps: informing the patient that they are likely to have prostate cancer or PD prostate cancer; performing confirmatory histological examination of prostate tissue; and/or treating the subject.

Thus, in certain aspects, if the detection step indicates that prostate cells from the subject have a genomic rearrangement of the ZBTB20 and LSAMP genes, the methods further comprise a step of taking a prostate biopsy from the subject and examining the prostate tissue in the biopsy (e.g., histological examination) to confirm whether the patient has prostate cancer or an aggressive form of prostate cancer. Alternatively, the methods of detecting or prognosing prostate cancer may be used to assess the need for therapy or to monitor a response to a therapy (e.g., disease-free recurrence following surgery or other therapy), and, thus may include an additional step of treating a subject having prostate cancer.

Prostate cancer treatment options include surgery, radiation therapy, hormone therapy, chemotherapy, biological therapy, or high intensity focused ultrasound. Drugs approved for prostate cancer include: Abiraterone Acetate, Cabazitaxel, Degarelix, Enzalutamide (XTANDI), Jevtana (Cabazitaxel), Prednisone, Provenge (Sipuleucel-T), Sipuleucel-T, or Docetaxel. Thus a method as described in this application may, after a positive result, include a further step of surgery, radiation therapy, hormone therapy, chemotherapy, biological therapy, or high intensity focused ultrasound.

Computer-Implemented Models

In accordance with all aspects and embodiments of the invention, the methods provided may be computer-implemented.

The status of the genomic rearrangement of the ZBTB20 and LSAMP genes or the PTEN gene can be analyzed and associated with status of a subject (e.g., presence of prostate cancer or severity of disease (e.g., WD or PD prostate cancer)) in a digital computer. Optionally, such a computer is directly linked to a scanner or the like receiving experimentally determined signals related to the expression of a genomic rearrangement of the ZBTB20 and LSAMP genes or the deletion of the PTEN gene. Alternatively, expression levels can be input by other means. The computer can be programmed to convert raw signals into expression levels (absolute or relative), compare measured expression levels with one or more reference expression levels, or a scale of such values. The computer can also be programmed to assign values or other designations to expression levels based on the comparison with one or more reference expression levels, and to aggregate such values or designations for multiple genes in an expression profile. The computer can also be programmed to output a value or other designation providing an indication of the presence or severity of prostate cancer as well as any of the raw or intermediate data used in determining such a value or designation.

A typical computer (see U.S. Pat. No. 6,785,613, FIGS. 4 and 5) includes a bus which interconnects major subsystems such as a central processor, a system memory, an input/output controller, an external device such as a printer via a parallel port, a display screen via a display adapter, a serial port, a keyboard, a fixed disk drive and a port (e.g., USB port) operative to receive an external memory storage device. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above. The automated apparatus can include a robotic arm for delivering reagents for determining expression levels, as well as small vessels, e.g., microtiter wells for performing the expression analysis.

Figure 3:
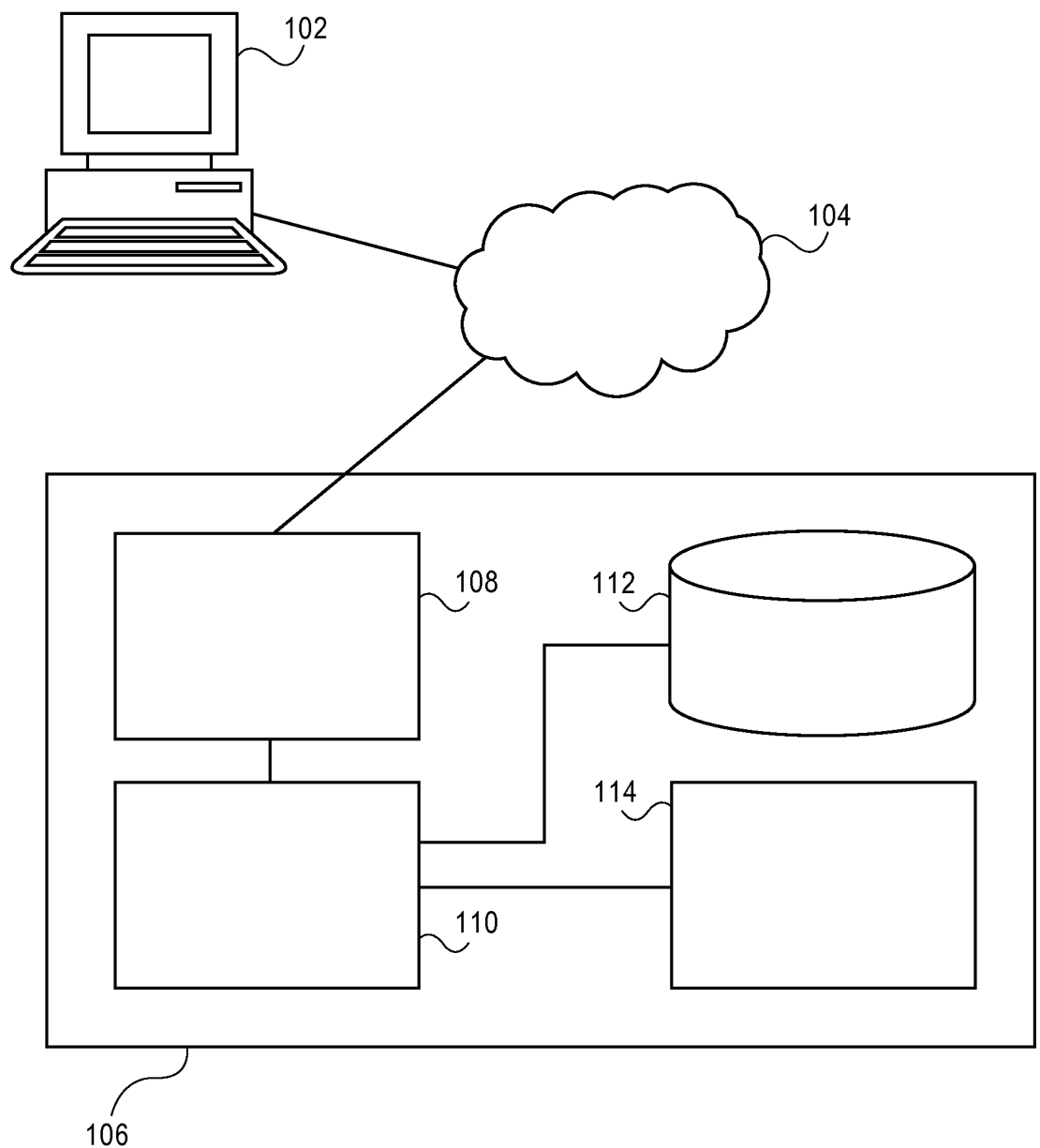
FIG. 3 shows a schematic diagram of a system according to some embodiments of the invention. In particular, this figure illustrates various hardware, software, and other resources that may be used in implementations of computer system 106 according to disclosed systems and methods. In embodiments as shown, computer system 106 may include one or more processors 110 coupled to random access memory operating under control of or in conjunction with an operating system. The processor(s) 110 in embodiments may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processor(s) 110 may communicate with data store 112, such as a database stored on a hard drive or drive array, to access or store program instructions other data.

A typical computer system 106 may also include one or more processors 110 coupled to random access memory operating under control of or in conjunction with an operating system as set forth in FIG. 3 and discussed above.

In one embodiment, any of the computer-implemented methods of the invention may comprise a step of obtaining by at least one processor information reflecting whether a biological sample contains a genomic rearrangement of the ZBTB20 and LSAMP genes or a deletion of the PTEN gene. In one embodiment, the biological sample is obtained from a subject of African descent. In another embodiment, the biological sample is obtained from a subject, wherein prostate cancer from the subject does not express a TMPRSS2/ERG gene fusion.

In another embodiment, any of the computer-implemented methods of the invention may further comprise a step of obtaining by at least one processor information reflecting the expression level of at least 2, 3, 4, 5, 6, or 7 of the following human genes: COL10A1, HOXC4, ESPL1, MMP9, ABCA13, PCDHGA1, and AGSK1 in a biological sample obtained from a patient of African descent.

In another embodiment of the computer-implemented methods of the invention, the methods may additionally comprise the steps outputting in user readable format the information obtained in the obtaining step.

In another embodiment of the computer-implemented methods of the invention, the methods may further comprise outputting in user readable format a determination that the subject has prostate cancer or poorly differentiated prostate cancer based on the information conveyed in the outputting step.

Compositions and Kits

The polynucleotide probes and/or primers or antibodies or polypeptide probes that are used in the methods described in this application can be arranged in a composition or a kit. Thus, one embodiment is directed to a composition for diagnosing or prognosing prostate cancer comprising a polynucleotide probe for detecting a genomic rearrangement of the ZBTB20 and LSAMP genes. In certain embodiments, where the genomic rearrangement comprises a fusion between the ZBTB20 and LSAMP genes, such as a fusion between exon 1 (e.g., E1, E1A, E1B, or E1C) of the ZBTB20 gene and exon 3* or exon 4 of the LSAMP gene, the polynucleotide probe hybridizes under high stringency conditions to a junction of a chimeric nucleic acid, wherein the chimeric nucleic acid comprises a first portion from a ZBTB20 gene (e.g., all or part of exon 1, which includes E1, E1A, E1B, or E1C) and a second portion from a LSAMP gene (e.g., all or part of exon 3* or exon 4). All of the polynucleotide probes described herein may be optionally labeled.

In one embodiment, the composition for diagnosing or prognosing prostate cancer comprises a polynucleotide probe, wherein the polynucleotide probe is designed to detect a chromosomal rearrangement of genomic DNA having a first portion from the ZBTB20 gene (e.g., all or part of exon 1, which includes E1, E1A, E1B, or E1C) and a second portion from the LSAMP gene (e.g., all or part of exon 3* or exon 4). In one embodiment, the polynucleotide probe hybridizes under high stringency conditions to a chromosomal rearrangement comprising the nucleotide sequence of SEQ ID NO:1.

In another embodiment, the composition for diagnosing or prognosing prostate cancer comprises a polynucleotide probe, wherein the polynucleotide probe is designed to detect a chimeric mRNA or cDNA transcript having a first nucleic acid portion from the ZBTB20 gene and a second nucleic acid portion from the LSAMP gene. In one embodiment, the chimeric mRNA or cDNA transcript comprises a fusion between exon 1 (e.g., E1, E1A, E1B, or E1C) of the ZBTB20 gene and exon 4 of the LSAMP gene. For example, in certain embodiments, the polynucleotide probe hybridizes under high stringency conditions to a chimeric mRNA or cDNA transcript having the nucleotide sequence of SEQ ID NO:4, SEQ ID NO:32, SEQ ID NO:34, SEQ ID NO:35, SEQ ID NO:36, SEQ ID NO:37, SEQ ID NO:38, or SEQ ID NO:40. In another embodiment, the chimeric mRNA or cDNA transcript comprises a fusion between exon 1 (e.g., E1, E1A, E1B, or E1C) of the ZBTB20 gene and exon 3* of the LSAMP gene. For example, in certain embodiments, the polynucleotide probe hybridizes under high stringency conditions to a chimeric mRNA or cDNA transcript having the nucleotide sequence of SEQ ID NO:33, SEQ ID NO:39, or SEQ ID NO:41.

In yet another embodiment, the composition for diagnosing or prognosing prostate cancer comprises a polynucleotide probe, wherein the polynucleotide probe is designed to detect a deletion in chromosome region 3q13, wherein the deletion spans the ZBTB20 and LSAMP genes.

In other embodiments, the polynucleotide probe hybridizes under high stringency conditions to exon 3* of a LSAMP gene (SEQ ID NO:45) or a junction of a chimeric nucleic acid, wherein the chimeric nucleic acid comprises a first portion from exon 3* of a LSAMP gene and a second portion from exon 4 of a LSAMP gene.

In yet other embodiments, the polynucleotide probe hybridizes under high stringency conditions to exon 0* of a LSAMP gene (SEQ ID NO:47) or a junction of a chimeric nucleic acid, wherein the chimeric nucleic acid comprises a first portion from exon 0* of a LSAMP gene and a second portion from exon 1 of a LSAMP gene.

The compositions for diagnosing or prognosing prostate cancer may also comprise primers. In one embodiment, wherein the genomic rearrangement comprises a gene fusion between the ZBTB20 and LSAMP genes, such as a fusion between exon 1 (e.g., E1, E1A, E1B, or E1C) of the ZBTB20 gene and exon 3* or exon 4 of the LSAMP gene, the composition comprises primers for amplifying the ZBTB20/LSAMP gene fusion and, in particular, primers for amplifying a nucleotide sequence from the gene fusion that spans the junction between a first portion of the gene fusion from the ZBTB20 gene (e.g., all or part of exon 1, which includes E1, E1A, E1B, or E1C) and a second portion of the gene fusion from the LSAMP gene (e.g., all or part of exon 3* or exon 4). In this way, the primers can be used to specifically identify a gene fusion between the ZBTB20 and LSAMP genes. In one embodiment, the composition comprises a first polynucleotide primer comprising a sequence that hybridizes under high stringency conditions to a first portion of the gene fusion from the ZBTB20 gene (e.g., all or part of exon 1, which includes E1, E1A, E1B, or E1C); and a second polynucleotide primer comprising a sequence that hybridizes under high stringency conditions to the second portion of the gene fusion from the LSAMP gene (e.g., all or part of exon 3* or exon 4), wherein the first and second polynucleotide primers are capable of amplifying a nucleotide sequence from the gene fusion that spans the junction between the first portion of the gene fusion from the ZBTB20 gene and the second portion of the gene fusion from the LSAMP gene. In certain embodiments, the composition comprises a first and a second polynucleotide primer for amplifying a gene fusion between a ZBTB20 gene and an LSAMP gene, wherein the first and the second polynucleotide primer are capable of amplifying one or more of SEQ ID NOs 32-41 or a portion thereof that spans the junction between a first portion of the gene fusion from the ZBTB20 gene and a second portion of the gene fusion from the LSAMP gene.

In one embodiment, the first portion of the gene fusion from the LSAMP gene comprises the nucleotide sequence of SEQ ID NO:2 and the second portion of the gene fusion from the ZBTB20 gene comprises the nucleotide sequence of SEQ ID NO:3. In another embodiment, the first portion of the gene fusion from the ZBTB20 gene comprises the nucleotide sequence of SEQ ID NO:5 and the second portion of the gene fusion from the LSAMP gene comprises the nucleotide sequence of SEQ ID NO:6. In yet another embodiment, the first polynucleotide primer comprises the nucleotide sequence of SEQ ID NO:7 and the second polynucleotide primer comprises the nucleotide sequence of SEQ ID NO:8.

Exon 3* (SEQ ID NO:45) represents a novel exon sequence from the LSAMP locus that has not been previously annotated and has now been found in fusion transcripts resulting from the genomic rearrangement of the ZBTB20 and LSAMP genes. Therefore, amplifying an mRNA/cDNA sequence corresponding to a region of exon 3* that is not present in other genes provides yet another mechanism for detecting the genomic rearrangement of the ZBTB20 and LSAMP genes. In one embodiment, the composition comprises a first polynucleotide primer comprising a sequence that hybridizes under high stringency conditions to a first portion of exon 3* of LSAMP, and a second polynucleotide primer comprising a sequence that hybridizes under high stringency conditions to a sequence complementary to a second portion of exon 3* of LSAMP, wherein the first and second portions of the exon 3* of LSAMP do not overlap and wherein the polynucleotide primers are capable of amplifying a nucleotide sequence within exon 3* of LSAMP that is unique to the 3* exon and is not found in other gene sequences and, thus, can be used to positively identify the amplified sequence as coming from exon 3* of LSAMP. In other embodiments, the second polynucleotide primer hybridizes under high stringency conditions to a sequence complementary to a region within exon 4 of LSAMP, such that the primer pair yields an amplification product that spans the junction between exon 3* and exon 4 of LSAMP. The second primer can also hybridize to a sequence complementary to a region with exon 5, 6, or 7 of LSAMP.

Exon 0* (SEQ ID NO:47) represents a novel exon sequence the LSAMP locus that has not been previously annotated and was identified in an alternatively spliced transcript in a patient having a genomic rearrangement of the ZBTB20 and LSAMP genes. Therefore, amplifying an mRNA/cDNA sequence corresponding to a region of exon 0* that is not present in other genes provides yet another mechanism for detecting the genomic rearrangement of the ZBTB20 and LSAMP genes. In one embodiment, the composition comprises a first polynucleotide primer comprising a sequence that hybridizes under high stringency conditions to a first portion of exon 0* of LSAMP, and a second polynucleotide primer comprising a sequence that hybridizes under high stringency conditions to a sequence complementary to a second portion of exon 0* of LSAMP, wherein the first and second portions of exon 0* of LSAMP do not overlap and wherein the polynucleotide primers are capable of amplifying a nucleotide sequence within exon 0* of LSAMP that is unique to the 0* exon and is not found in other gene sequences and, thus, can be used to positively identify the amplified sequence as coming from exon 0* of LSAMP. In other embodiments, the second polynucleotide primer to hybridizes under high stringency conditions to a sequence complementary to a region within exon 1 of LSAMP, such that the primer pair yields an amplification product that spans the junction between exon 0* and exon 1 of LSAMP. The second primer can also hybridize to a sequence complementary to a region with exon 2, 3, or 4 of LSAMP.

In another embodiment, wherein the genomic rearrangement comprises a deletion at chromosome region 3q13, wherein the deletion spans both the ZBTB20 and LSAMP genes, the composition for diagnosing or prognosing prostate cancer comprises primers for amplifying a chimeric junction created by the deletion. Thus, in one embodiment, the composition comprises a first polynucleotide primer comprising a sequence that hybridizes under high stringency conditions to a first nucleic acid that borders a 5' end of the deletion; and a second polynucleotide primer comprising a sequence that hybridizes under high stringency conditions to the second nucleic acid that borders a 3' end of the deletion, wherein the first and second polynucleotide primers are capable of amplifying a nucleotide sequence that spans the chimeric junction created by the deletion, wherein the deletion occurs at chromosome region 3q13 and spans the ZBTB20 and LSAMP genes.

Another aspect is directed to a double stranded oligonucleotide duplex, wherein the oligonucleotide duplex comprises a first nucleic acid hybridized to a second nucleic acid, wherein the first nucleic acid comprises a first portion from a ZBTB20 gene fused to a second portion from a LSAMP gene and wherein the second nucleic acid is a polynucleotide probe that is hybridized to a junction between the first portion from the ZBTB20 gene and the second portion from the LSAMP gene. The polynucleotide probe is optionally labeled.

In another embodiment, the oligonucleotide duplex comprises a first nucleic acid hybridized to a second nucleic acid, wherein the first nucleic acid comprises a first portion from exon 3* of a LSAMP gene fused to a second portion from exon 4 of a LSAMP gene and wherein the second nucleic acid is a polynucleotide probe that is hybridized to a junction between the first portion from exon 3* of the LSAMP gene and the second portion from exon 4 of the LSAMP gene. The polynucleotide probe is optionally labeled.

In yet another embodiment, the oligonucleotide duplex comprises a first nucleic acid hybridized to a second nucleic acid, wherein the first nucleic acid comprises a first portion from exon 0* of a LSAMP gene fused to a second portion from exon 1 of a LSAMP gene and wherein the second nucleic acid is a polynucleotide probe that is hybridized to a junction between the first portion from exon 0* of the LSAMP gene and the second portion from exon 4 of the LSAMP gene. The polynucleotide probe is optionally labeled.

Another aspect is directed to kits for diagnosing or prognosing prostate cancer. In one embodiment, the kit for diagnosing or prognosing prostate cancer comprises a first composition comprising one or more polynucleotide probes and/or primers for detecting a ZBTB20/LSAMP genomic rearrangement, as discussed above, and a second composition comprising a polynucleotide probe that hybridizes under high stringency conditions to a gene selected from COL10A1, HOXC4, ESPL1, MMP9, ABCA13, PCDHGA1, and AGSK1.

In another embodiment, the kit for diagnosing or prognosing prostate cancer comprises a first composition comprising one or more polynucleotide probes and/or primers for detecting a ZBTB20/LSAMP genomic rearrangement, as discussed above, and a second composition comprising a polynucleotide probe that hybridizes under high stringency conditions to a gene selected from ERG, AMACR, PCA3, and PSA.

The kit for diagnosing or prognosing prostate cancer may also comprise antibodies. Thus, in one embodiment, the kit for diagnosing or prognosing prostate cancer comprises an antibody that binds to a polypeptide encoded by a ZBTB20/LSAMP gene fusion. The antibody may be optionally labeled. In another embodiment, the kit further comprises one or more antibodies for detecting at least 1, 2, 3, 4, 5, 6, or 7 of the polypeptides encoded by following human genes: COL10A1, HOXC4, ESPL1, MMP9, ABCA13, PCDHGA1, and AGSK1. In another embodiment, the kit further comprises one or more antibodies for detecting ERG, AMACR, or PSA.

In one embodiment, a kit for diagnosing or prognosing prostate cancer includes instructional materials disclosing methods of use of the kit contents in a disclosed method. The instructional materials may be provided in any number of forms, including, but not limited to, written form (e.g., hardcopy paper, etc.), in an electronic form (e.g., computer diskette or compact disk) or may be visual (e.g., video files). The kits may also include additional components to facilitate the particular application for which the kit is designed. Thus, for example, the kits may additionally include other reagents routinely used for the practice of a particular method, including, but not limited to buffers, enzymes (e.g., polymerase), labeling compounds, and the like. Such kits and appropriate contents are well known to those of skill in the art. The kit can also include a reference or control sample. The reference or control sample can be a biological sample or a data base.

The polynucleotide probes and antibodies described in this application are optionally labeled with a detectable label. Any detectable label used in conjunction with probe or antibody technology, as known by one of ordinary skill in the art, can be used. In a particular embodiment, the probe is labeled with a detectable label selected from the group consisting of a fluorescent label, a chemiluminescent label, a quencher, a radioactive label, biotin, mass tags and/or gold.

Antibodies that Bind to a Chimeric ZBTB20/LSAMP Fusion Protein

This disclosure provides antibodies that bind to the protein encoded by the ZBTB20/LSAMP gene fusion. Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. Identification and numbering of framework and CDR residues is as described by Chothia et al., Structural determinants in the sequences of immunoglobulin variable domain, J Mol Biol 1998, 278:457-79, which is hereby incorporated by reference in its entirety.

In one embodiment, the protein encoded by the ZBTB20/LSAMP gene fusion is a truncated LSAMP protein. In certain embodiments, the antibody that binds to the truncated LSAMP protein binds to an epitope present in the truncated LSAMP protein but not present in the wild type LSAMP protein. In one embodiment, the antibody binds to a chimeric polypeptide encoded by a gene fusion between exon 1 of the ZBTB20 gene and exon 4 of the LSAMP gene. In certain embodiments, the antibody that binds to a chimeric polypeptide encoded by a gene fusion between exon 1 of the ZBTB20 gene and exon 4 of the LSAMP gene, binds to an epitope present in the polypeptide encoded by the gene fusion that is not present in either the wild type ZBTB20 or wild type LSAMP protein. In another embodiment, the gene fusion comprises the nucleotide sequence of SEQ ID NO:4.

Methods of making antibodies, or antigen-binding fragments thereof, and formulating the same for therapeutic administration are well known as discussed, for example, in PCT/US2010/032714, which is hereby incorporated by reference in its entirety.

The antibodies described herein that bind to a polypeptide encoded by a ZBTB20/LSAMP gene fusion can be used in a variety of research and medical applications. In one aspect, the disclosure provides a method of treating prostate cancer in a subject, comprising administering to said subject a therapeutically effective amount of an antibody that binds to a polypeptide encoded by a ZBTB20/LSAMP gene fusion formulated in a pharmaceutically acceptable vehicle.

The disclosure also provides compositions comprising an antibody that binds to a polypeptide encoded by a ZBTB20/LSAMP gene fusion. In certain embodiments, the compositions are suitable for pharmaceutical use and administration to patients. These compositions comprise an antibody that binds to a polypeptide encoded by a ZBTB20/LSAMP gene fusion and a pharmaceutically acceptable excipient. The compositions may also contain other active compounds providing supplemental, additional, or enhanced therapeutic functions. The pharmaceutical compositions may also be included in a container, pack, or dispenser together with instructions for administration. In one embodiment, the composition comprises a monoclonal antibody that binds to a polypeptide encoded by a ZBTB20/LSAMP gene fusion for use in treating prostate cancer.

A pharmaceutical composition of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically contemplated, by such means as depot injections or erodible implants. Localized delivery is particularly contemplated, by such means as delivery via a catheter to one or more arteries, such as the renal artery or a vessel supplying a localized tumor.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Example 1. Comparative Genomic DNA Analysis

A comparative full genome analysis was conducted using primary prostate tumors and corresponding normal tissue (blood) in a cohort of seven AA and seven CA CaP patients (28 specimens). The cohort was selected based on the following criteria: primary treatment radical prostatectomy, no neo-adjuvant treatment, Gleason 6-7 (aka, primary pattern 3 or Gleason grade 3+3 and 3+4, which represents the majority of PSA-screened CaP at diagnosis/primary treatment), frozen tumor tissue with 80% or more tumor cell content, dissected tumor tissue yielding over 2 μg high molecular weight genomic DNA, availability of corresponding blood genomic DNA and patient clinico-pathological data.

28 samples were sent to Illumina Inc. (UK) for sequencing. Sequences from tumor samples were mapped to the reference genome using Illumina's ELAND alignment algorithm. Sequencing reported good coverage (average 37). Variant calling for single nucleotide polymorphisms (SNPs), small insertions and deletions (InDels), copy number variants (CNVs), and structural variants (SVs) was performed concurrently using the Strelka algorithm. All established CaP mutations (TMPRSS2/ERG, SPOP, CHD1, and PTEN) were identified at expected frequencies in this cohort. A genome sequence coverage summary of the 14 patients is presented in Table 2.

TABLE 2

| | Sample ID | | | | | | |
|---|---|---|---|---|---|---|---|
| | GP-10 | GP-04 | GP-02 | GP18 | GP-12 | GP-13 | GP-15 |
| Ethnicity | AA | AA | AA | AA | AA | AA | AA |
| TMPRS52-ERG Status | − | − | − | − | + | + | + |
| Tumor: estimated purity (%) | 90 | 80 | 80 | 80 | 90 | 85 | 80 |
| Tumor Differentiation (%) | WD 95 PD 5 | WD 95 PD 5 | WD 100 | WD 100 | WD 100 | WD 92 PD 8 | WD 100 |
| Tumor Gleason | 7 (3 + 4) | 7 (3 + 4) | 6 (3 + 3) | 6 (3 + 3) | 6 (3 + 3) | 7 (3 + 4) | 6 (3 + 3) |
| Tumor: bases sequenced and aligned (in Gb) | 118.5 | 116.7 | 114.7 | 116.2 | 112.6 | 107.6 | 114.2 |
| Tumor: haploid coverage | 39.2 | 38.3 | 37.8 | 38.6 | 37.2 | 34.9 | 38.1 |
| Coverage-% Positions >=1x | 98 | 98 | 98 | 98 | 98 | 98 | 98 |
| Normal: bases sequenced and aligned (in Gb) | 111.6 | 111.8 | 112.2 | 102.4 | 117.7 | 113.4 | 108.1 |
| Normal: haploid coverage | 37.1 | 37.5 | 37.3 | 34.1 | 39.2 | 37.6 | 36 |
| Coverage-% positions >=1x | 98 | 98 | 98 | 98 | 98 | 98 | 98.1 |
| Mutation rate/Mb | 0.9 | 0.98 | 0.82 | 0.69 | 0.72 | 0.68 | 0.76 |
| Non-silent point mutations (>25% read coverage) | 23 | 25 | 25 | 20 | 8 | 13 | 12 |

| | Sample ID | | | | | | |
|---|---|---|---|---|---|---|---|
| | GP-06 | GP-11 | GP-16 | GP-07 | GP-01 | GP-09 | GP-17 |
| Ethnicity | CA | CA | CA | CA | CA | CA | CA |
| TMPRS52-ERG Status | − | − | − | + | + | + | + |
| Tumor: estimated purity (%) | 95 | 90 | 90 | 90 | 80 | 80 | 80 |
| Tumor Differentiation (%) | WD 95 PD 5 | WD 100 | WD 85 PD 15 | WD 100 | WD 95 PD 5 | WD 97 PD 3 | WD 95 PD 5 |
| Tumor Gleason | 7 (3 + 4) | 6 (3 + 3) | 7 (3 + 4) | 6 (3 + 3) | 7 (3 + 4) | 7 (3 + 4) | 7 (3 + 4) |
| Tumor: bases sequenced and aligned (in Gb) | 123.5 | 107.5 | 108.6 | 106.5 | 117.5 | 111.9 | 111.3 |
| Tumor: haploid coverage | 41 | 35 | 36 | 34.9 | 39 | 37.2 | 36.6 |
| Coverage-% Positions >=1x | 98.1 | 98 | 98 | 98 | 98 | 98 | 98 |
| Normal: bases sequenced and aligned (in Gb) | 113.3 | 109.8 | 115.3 | 121.9 | 104 | 105.3 | 112.2 |
| Normal: haploid coverage | 37.5 | 36.4 | 38.5 | 40.3 | 34.4 | 35.2 | 37.4 |
| Coverage-% positions >=1x | 98 | 98 | 98 | 98 | 98 | 98 | 98 |
| Mutation rate/Mb | 1.27 | 0.75 | 1.03 | 0.74 | 2.33 | 1.02 | 1.13 |
| Non-silent point mutations (>25% read coverage) | 38 | 19 | 26 | 16 | 38 | 15 | 35 |

Thirty one genes (including known mutations) with SNP, CNV or InDel somatic mutations in at least two of 14 patients were identified: AC091435.2; APC; ASMTL; ASMTL-AS1; CDC73; CHD1; CSF2RA; EYS; FRG1; FRG1B; HK2; IL3RA; KLLN; LIPF; LOC100293744; MT-ATP6; MT-BD4; MT-CO1; MT-CYB: MT-ND2; MT-ND3; MUC16; MUC6; NOX3; PDHA2; PTEN; SLC25A6; SLC9B1; SPOP; TRAV20; and USH2A. The top SVs and CNVs (highest confidence) present in at least 2 of 14 patients are set forth in Table 3:

TABLE 3

| Gene | Structural and Copy Number Variants | Ethnicity | Score |
|---|---|---|---|
| ZBTB20-LSAMP | Structural and Copy Number Variation | AD | 17 |
| TMPRSS2-ERG* | Structural Variation (Gene Fusion) | CD > AD | 27 |
| HLA-DRB5 | Structural Variation | AD > CD | 42 |
| MLL3-BAGE | Structural Variation | No | 30 |
| HLA-B | Structural Variation | AD > CD | 19 |
| FOXP1 | Structural and Copy Number Variation | No | 19 |
| CHD1* | Copy Number Variation | No | 9 |
| TRAV20 | Structural and Copy Number Variation | AD > CD | 8 |
| PTEN* | Copy Number Variant | CD > AD | 5 |

TABLE 3-continued

| Gene | Structural and Copy Number Variants | Ethnicity | Score |
|---|---|---|---|
| PRDM2-VS13D | Structural and Copy Number Variation | No | 5 |
| RPL11-SLC30A2 | Structural Variation | AD | 5 |

TABLE 3-continued

| Gene | Structural and Copy Number Variants | Ethnicity | Score |
|---|---|---|---|
| SLC45A3 | Structural Variation | No | 5 |
| PCDH10 | Structural and Copy Number Variation | AD | 4 |

*Known gene alteration in CaP
African descent = AD;
Caucasian descent = CD

In Table 3, the "Score" is the sum of individual scores of maximum 5 for SV or 4 for CNV for each patient (theoretical maximum score for the 14 patients is 14×5=70 for SV, or 14×4=56 for CNV). A score of 1, 4 or 5 is given for SV (where 5 means SV is supported with RNA data, 4 means SV with splice reads, and 1 if no splice reads or RNA data is available), and a score of 2 or 4 is given for CNV (2 if it is predicted by one algorithm, and 4 if it is predicted by more than one algorithm).

Certain SNV, CNV or InDel somatic mutations exhibited a preferred association with a specific ethnic group (AD (African Descent), CD (Caucasian Descent), AD>CD, or CD>AD). In particular, the absence of PTEN deletions in AA patients was unexpected. PTEN deletion was detected in 4 of 7 CD, indicating the potential exclusivity of PTEN deletions in CD cases.

Example 2. Stratification of ZBTB20/LSAMP and PTEN Genetic Alterations Based on Ethnicity Established prostate cancer genomic defects (TMPRSS2/ERG, PTEN) as well as a novel recurrent rearrangement affecting the ZBTB20/LSAMP loci on chromosome 3q13 were identified in this cohort of 14 patients. All three (ZBTB20/LSAMP (GP10), TMPRSS2/ERG (GP1-14), and PTEN (GP1-14)) were validated by RT-PCR or FISH analyses.

TABLE 4

| Sample ID | Ethnicity | TMPRSS2 ERG | ZBTB20 LSAMP | PTEN Deletion |
|---|---|---|---|---|
| GP-02 | AA | − | + | − |
| GP-04 | AA | − | + | − |
| GP-10 | AA | − | + | − |
| GP-18 | AA | − | − | − |
| GP-12 | AA | + | − | − |
| GP-13 | AA | + | − | − |
| GP-15 | AA | + | − | − |
| GP-06 | CA | − | − | − |
| GP-11 | CA | − | − | + |
| GP-16 | CA | − | − | + |
| GP-01 | CA | + | − | + |
| GP-07 | CA | + | − | − |
| GP-09 | CA | + | − | − |
| GP-17 | CA | + | − | + |

+ indicates presence;
− indicates absence

The PTEN deletion was not observed in any of the AD patients (0 of 7). It was detected only in CD patients (4 of 7), suggesting that PTEN loss is an infrequent event in CaP development of men of AD. Activation of ERG (via gene fusion with androgen regulated genes, such as TMPRSS2), which has been associated with PTEN deletion, are also less frequent in CaP patients of AD [20]. The observed association of PTEN deletion with CD ethnicity was apparent and similar only to the ERG rearrangement when compared to other structural (SV) or copy number (CNV) variations (see Table 3 above).

PTEN deletions identified by whole genome sequencing were independently confirmed by FISH assay in identical tumor foci in consecutive sections of whole mount prostates from the 7 AD and 7 CD. FIG. 4A.

To validate these findings PTEN deletions were assessed by FISH assay in a tissue microarray (TMA) of 41 AD and 58 CD cases representing Gleason 6, Gleason 7 or Gleason 8-10 tumors. Multiple samples including different tumor foci from each case were represented in the TMA. Examining all cores in the TMA, a significantly lower overall frequency of PTEN deletion was observed in AD (19.5%) when compared to CD (62.1) cases (Table 5A). Consistent with the indicated low frequency of PTEN deletion from the whole-genome sequences of Gleason 6-7 tumors of AD CaPs, PTEN deletions were found in only 1 out of 15 (6.7%) Gleason sum 6 and only 4 out of 15 (27%) Gleason sum 7 AD cases (Table 5B). This is in sharp contrast to PTEN deletion frequencies found in 10 out of 19 (52.6%) Gleason sum 6 and 14 out of 21 (66.7%) Gleason sum 7 CD CaPs. Taken together, these results validate the finding that PTEN loss is an infrequent event in CaPs of AD. Ethnic disparities noted in CaP include higher genomic frequencies of PTEN deletion in CD when compared to Asian men [34]. Recent reports have shown lower frequency of PTEN deletions in AD CaP patients in comparison to CD CaP patients [35, 36].

TABLE 5A

| | PTEN deletion | | |
|---|---|---|---|
| Race | No | Yes | P value |
| AD, N = 41 | 33 (80.5) | 8 (19.5) | <.0001 |
| CD, N = 58 | 22 (37.9) | 36 (62.1) | |

TABLE 5B

| | Overall (N = 91) | | | AD (N = 39) | | | CD (N = 45) | | |
|---|---|---|---|---|---|---|---|---|---|
| Worst Gleason Sum | PTEN no deletion | PTEN deletion | P value | PTEN no deletion | PTEN deletion | P value | PTEN no deletion | PTEN deletion | P value |
| 6 or less | 23 (67.6) | 11 (32.4) | 0.2571 | 14 (93.3) | 1 (6.7%) | 0.3185 | 9 (47.4) | 10 (52.6) | 0.6055 |
| 7 | 18 (50.0) | 18 (50.0) | | 11 (73.3) | 4 (26.7) | | 7 (33.3) | 14 (66.7) | |

TABLE 5B-continued

| Worst Gleason Sum | Overall (N = 91) | | | AD (N = 39) | | | CD (N = 45) | | |
| --- | --- | --- | --- | --- | --- | --- | --- | --- | --- |
| | PTEN no deletion | PTEN deletion | P value | PTEN no deletion | PTEN deletion | P value | PTEN no deletion | PTEN deletion | P value |
| 8 to 10 | 11 (50.0) | 11 (50.0) | | 7 (70.0) | 3 (30.0) | | 4 (33.3) | 8 (66.7) | |

In patients of AD with ERG negative CaP (i.e., no ERG/TMPRSS2 fusion), genomic rearrangements of the ZBTB20-LSAMP chromosomal loci (Chr. 3q13) was noted in 3 of 4 patients. Detailed analysis of the affected loci and RNA-Seq data revealed three different genomic rearrangements of the 3q13 loci.

Figure 2:
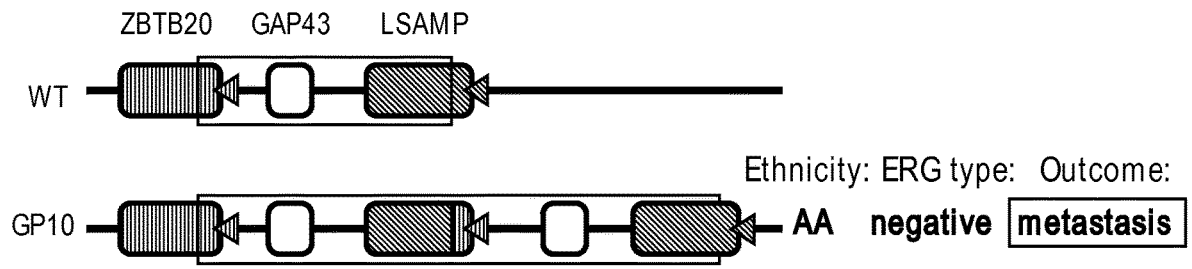
FIG. 2 shows the genomic arrangement of chromosome region 3q13 in patient GP10 and provides the cDNA sequence of the junction between exon 1 of ZBTB20 and exon 4 of LSAMP that results from the genomic arrangement.
Figure 2:

Detailed analysis of the affected loci and RNA-Seq data indicated that in one instance, the genomic rearrangement of the 3q13 loci involved a tandem duplication giving rise to a fusion between exon 1 of ZBTB20 and exon 4 of LSAMP. FIGS. 1 and 2. More specifically, the genomic rearrangement gave rise to a fusion between (a) a portion of the LSAMP gene having the sequence:

(SEQ ID NO: 2)
AGAGTCTCTTCTTTGGGTCTCTTCCACATAGCTTGTTTGTAATCTCCAAG

AAAGACTTCACATTACAGGCTGAAAAGAATCACCTACGGTTTCCATATTT

TGAAAGAAATTTTTAAAAACCATGAAAACAAACAAACAAAAATCCTAGTT

TCCTTTATAAAATAGCAAAGGAAAGTTCTCTCTCCTGTCACCAGGAATAT

GATTATGATCAGTTGGTTATTTAGGTCACATGTGAAAGAAATGAAAGAGG

AGGCATGGGAATGTAAGGGAGAATAGTAGTCTGCCCTCAAGTCTGCAAAC
G;
and (b) a portion of the ZBTB20 gene having the sequence:

(SEQ ID NO: 3)
CTCGAGAACAGTGAGCAATAAATTTTTCTTTATACATTACCCAGTCTGTG

GTATTCTGTTATGGCAACACAAAATAAACTAAGACAGTATTATGTATTTT

TTCTTTTGTTTTACATTTTACTAAGTGCCGACTTATTCGAAAAGGTAATT

AGCTTTGGTTAATTATCAAAGTTTTGTCTTTCCTTTCCTACTTTTGTCCC

ACTAAGCAAAAACAAAACAATGAGCATTGACCTTTACCTTTCTCTGGTA

AGGGAGTATGGAAGGTTTTCTACTACTTTGTAAAAATACTGCTACAGATG
G.

When combined, the genomic rearrangement of the ZBTB20 and LSAMP genes, in this one instance, had the following sequence:

(SEQ ID NO: 1)
CTCGAGAACAGTGAGCAATAAATTTTTCTTTATACATTACCCAGTCTGTG

GTATTCTGTTATGGCAACACAAAATAAACTAAGACAGTATTATGTATTTT

TTCTTTTGTTTTACATTTTACTAAGTGCCGACTTATTCGAAAAGGTAATT

AGCTTTGGTTAATTATCAAAGTTTTGTCTTTCCTTTCCTACTTTTGTCCC

ACTAAGCAAAAACAAAACAATGAGCATTGACCTTTACCTTTCTCTGGTA

-continued
AGGGAGTATGGAAGGTTTTCTACTACTTTGTAAAAATACTGCTACAGATG

GAGAGTCTCTTCTTTGGGTCTCTTCCACATAGCTTGTTTGTAATCTCCAA

GAAAGACTTCACATTACAGGCTGAAAAGAATCACCTACGGTTTCCATATT

TTGAAAGAAATTTTTAAAAACCATGAAAACAAACAAACAAAAATCCTAGT

TTCCTTTATAAAATAGCAAAGGAAAGTTCTCTCTCCTGTCACCAGGAATA

TGATTATGATCAGTTGGTTATTTAGGTCACATGTGAAAGAAATGAAAGAG

GAGGCATGGGAATGTAAGGGAGAATAGTAGTCTGCCCTCAAGTCTGCAAA
CG

A cDNA sequence of the ZBTB20/LSAMP gene fusion resulting from this genomic rearrangement was identified as:

(SEQ ID NO: 4)
CACAACATCAAGAGCAGGAAAATGGACTCATTAGGGAGGCAGGCA

GTCATTACCACTCACACTGTACTTCCAGGGAGACACCGATTATAAGAAGA

GAAACTCAGCGCTGGGGAAGAAGGAAGGGAATTTGAAGGAGAAGAAGAAT

ATCTGGAGATCCTTGGCATCACCAGGGAGCAGTCAGGCAAATATGAGTGC

AAAGCTGCCAACGAGGTCTCCTCGGCGGATGTCAAACAAGTCAAGGTCAC

TGTGAACTATCCTCCCACTATCACAGAATCCAAGAGCAATGAAGCCACCA

CAGGACGACAAGCTTCACTCAAATGTGAGGCCTCGGCAGTGCCTGCACCT

GACTTTGAGTGGTACCGGGATGACACTAGGATAAATAGTGCCAATGGCCT

TGAGATTAAGAGCACGGAGGGCCAGTCTTCCCTGACGGTGACCAACGTCA

CTGAGGAGCACTACGGCAACTACACCTCHGTGGCTGCCAACAAGCTGGGG

GTCACCAATGCCAGCCTAGTCCTTTTCAGACCTGGGTCGGTGAGAGGAAT

AAATGGATCCATCAGTCTGGCCGTACCACTGTGGCTGCTGGCAGCATCTC

TGCTCTGCCTTCTCAGCAAATGTTAA.

In this ZBTB20/LSAMP gene fusion, the following sequence was derived from exon 1 of ZBTB20:

(SEQ ID NO: 5)
CACAACATCAAGAGCAGGAAAATGGACTCATTAGGGAGGCAGGCAGTCAT
TACCACTCACACTGTACTTCCAGGGAGACACCGATTATAAGAAGAGAAAC
TCAGCGCTGGGGAAGAAG, derived from exons 4-7 of LSAMP.

One of ordinary skill in the art can design primers for amplifying this ZBTB20/LSAMP gene fusion. In one embodiment, the forward primer comprises the nucleotide sequence of SEQ ID NO:5 or a sequence complementary thereto and the reverse primer comprises the nucleotide sequence of SEQ ID NO:6 or a sequence complementary thereto. The following exemplary primers were designed to amplify this particular ZBTB20/LSAMP gene fusion:

```
ZBTB20/LSAMP Forward Primer:
                            (SEQ ID NO: 7)
GCAGGCAGTCATTACCACTC ZBTB20/LSAMP Reverse Primer:
                            (SEQ ID NO: 8)
TGACTTGTTTGACATCCGCC
```

In another instance, the genomic rearrangement of the 3q13 loci involved a deletion, giving rise to a fusion between the ZBTB20 gene and the LSAMP gene. FIG. 1. In the third instance, the genomic rearrangement of the 3q13 loci involved a large deletion of at least 22.7 Mb, spanning both the ZBTB20 and LSAMP genes. FIG. 1. Strikingly, two of the 3 patients with the chromosome 3q13 rearrangement developed metastasis (the only two metastasis in this cohort), and the third had biochemical recurrence of CaP (1 of 3 in the cohort), indicating that the ZBTB20/LSAMP genomic rearrangement is associated with an aggressive form of prostate cancer or an increased likelihood to develop an aggressive form of prostate cancer. FIG. 1.

To validate the association of the ZBTB20/LSAMP fusion transcript with AA ethnicity, negative ERG status, and adverse disease outcome, 20 additional CaP tumors and 24 CaP tumor-derived cell lines of AA and CA descent were evaluated using PCR and the primers described above. Of the 20 AA tumor samples analyzed, one contained the same ZBTB20/LSAMP fusion transcript, which was present in GP10 specimen. This patient had an ERG negative, aggressive form of prostate cancer (poorly differentiated with progression to metastasis). The ZBTB20/LSAMP genomic rearrangement was not detected in mRNA or genomic DNA of 34 normal samples (20 normal prostate tissue specimens and constitutional DNA from 7 CA and 7 AA patients). A ZBTB20/LSAMP rearrangement was detected in one CaP cell line (CPDR RC92), which was derived from a patient of AD with poorly differentiated prostate cancer.

ZBTB20-LSAMP deletions, identified in the tumor genome of two AD cases, were validated by FISH assay by probing the genomic region of chromosome 3 (from the ZBTB20 promoter upstream sequences through the GAP43 gene to the LSAMP locus 3' adjacent region) FIG. 4B. One of the AD cases harbored ZBTB20-LSAMP duplication rearrangement predicting an inactivating gene fusion between the promoter and first exon of ZBTB20 and LSAMP coding sequences. This gene fusion was confirmed by 5'-RACE method defining complete cDNA sequences of the 5' fusion partner, first exon of ZBTB20, the fusion junction, and the 3' fusion partner, LSAMP exon 4. The fusion transcript eliminates the natural translation initiation (ATG) of the LSAMP gene leading to the premature truncation of LSAMP protein.

To validate the findings a tissue microarray (TMA) was assessed by FISH assay for detecting the absence or presence of a DNA region between the ZBTB20 and LSAMP gene loci in 23 AD and 7 CD cases representing Gleason 6, Gleason 7 or Gleason 8-10 tumors. A deletion was detected in 26% (6 out of 23) of AD cases, whereas, the deletion was observed in only 1 out of 7 (14%) in CD cases (Table 6A). Among the seven cases with deletion, six had biochemical recurrence (Table 6B). ERG expression rearrangement was found only in two of the seven patients with the deletion in the ZBTB20-LSAMP region. PTEN deletion was found in only one case out of seven (Table 6B). Six of the seven patients having the deletion in the ZBTB20-LSAMP region experienced biochemical recurrence (BCR) or metastisis (Met) (Table 6B). These data support our original discovery showing an association of a significantly higher proportion of ZBTB20-LSAMP region deletions in AD CaP patients with poor prognosis (biochemical recurrence after prostatectomy or metastis).

TABLE 6A

|  | AD | CD |
|---|---|---|
| Deletion | 6 (26.09%) | 1 (14.29%) |
| No deletion | 17 (73.91%) | 6 (85.71%) |
| Total | 23 | 7 |

TABLE 6B

| Ethnicity | ERG | PTEN | BCR/Met |
|---|---|---|---|
| AD | Negative | wt | Yes |
| AD | Negative | wt | No |
| AD | Negative | wt | Yes |
| AD | Positive | wt | Yes/Yes |
| AD | Negative | wt | Yes |
| AD | Positive | wt | Yes |
| CD | Negative | deletion | Yes |

Evaluation of the affected 3q13 loci and RNA-Seq data indicated that the genomic rearrangement in one AD ERG negative case involved a tandem duplication giving rise to 5'-ZBTB20-LSAMP-3' fusion transcripts. The 5'-ZBTB20-LSAMP-3' fusion transcripts from this AD ERG negative case were also assessed by the "Rapid Amplification of cDNA Ends" (RACE) method. The sequence of RACE products were cloned in an M13 sequencing vector and confirmed by forward and reverse DNA sequencing for six clones for each RACE cDNA products. Ten prototypical CaP-associated fusion cDNA were identified, ZBTB20-LSAMP Fusion Type 1-to 10, respectively and one alternatively spliced cDNA of the LSAMP locus (LSAMP prostate cancer alternatively spliced form Type 1: LPCS1). FIG. 5. The sequences of these transcripts are set forth below with bold text indicating the portion from the ZBTB20 gene, and underlining indicating a sequence that was used as a reverse primer in the RACE method. A universal 5' RACE sequence was used as the forward primer in these amplification methods. The exons of the fusion transcripts and LPCS1 alternate between normal text and italicized text.

```
Type 1: ZBTB20-E1-LSAMP-E4-E5-E6-E7
                                                           (SEQ ID NO: 32)
AGAGTACATGCGCCGGGGGGAAGTTTAGGAGTTGAGGAAAGAAGATTAAAGAGCGCGAGGAG

GAAGGGAATTTGAAGGAGAAGAAGAATATCTGGAGATCCTTGGCATCACCAGGGAGCAGTCA

GGCAAATATGAGTGCAAAGCTGCCAACGAGGTCTCCTCGGCGGATGTCAAACAAGTCAAGGT

CACTGTGAACTATCCTCCCACTATCACAGAATCCAAGAGCAATGAAGCCACCACAGGACGAC
```

-continued

AAGCTTCACTCAAATGTGAGGCCTCGGCAGTGCCTGCACCTGACTTTGAGTGGTACCGGGAT

GACACTAGGATAAATAGTGCCAATGGCCTTGAGATTAAGAGCACGGAGGGCCAGTCTTCCCT

GACGGTGACCAACGTCACTGAGGAGCACTACGGCAACTACACCTGTGTGGCTGCCAACAAGC

TGGGGGTCACCAATGCCAGCCTAGTCCTTTTCAGACCTGGGTCGGTGAGAGGAATAAATGGA

TCCATCAGTCTGGCCGTACCACTGTGGCTGCTGGCAGCATCTCTGCTCTGCCTTCTCAGCAA

ATGTTAATAGAATAAAAATTTAAAAATAATTTAAAAAACACACAAAAATGTGTCACACAGAA

TACAGAGAGAGAGAGACAGAGAGAGAGAGAGAGAGAGATGGGGGAGACCGTTTATTTCAC

AACTTTGTGTGTTTATACATGAAGGGGGAAATAAGAAAGTGAAGAAGAAAATNACAACATTT

AAAACAATTTTACAGTCCATCATTAAAAATTTATGTATCATTCAGGATGGAGAAGGTTCTAC

TGGGATATGTTTATATCTACTAAGCAAATGTATGCTGTGTAAAGACTACACCACACTAAGGA

CATCTGGATGCTGTAAAATAAGAGAAGAACCAGATGGATATTAAGCCCCCCAACACACACT

TTATCCTTCCTTCCTTCATCTTTTTTCATCTGTGGGGAAGAAAATAAGGTCTTGCCTTTGGT

GTTTATATTTCCATAACCTTTTAATTCTATTTTTCATTTGAGCTGACTTGTAGCCACTTCAG

ACTATCAATGGAATCTTATGTTGAGCCTTTCTCTGGCTTTCCTTCCTCCACTATCTCTCCAA

CTTTAGAGATCATCCCCTCTCCCTCCAGT<u>GCGTTCTATCTCCCCCACACCCACCCAA</u>

Type 2: ZBTB20-E1C LSAMP E3A-E4-E5-E6-E7

(SEQ ID NO: 33)

ACATGGGGAGGTTGCAGTGTGTGTATATACACAACATCAAGAGCAGGAAAATGGACTCATTA

GGGAGGCAGGCAGTCATTACCACTCACACTGTACTTCCAGGGAGACACCGATTATAAGAAGA

GAAACTCAGCGCTGGGGAAGAAGATTAACTTACTCTTAATGATCTTCCAACACTTGAGAAGG

TCAGTAGCCCTCCATCTGTCATTCTCCAAGTTCACCAACAGCTTATCCACCCATCAAAGGTG

CTTTTGTAACAAAATCCATGCATAATGAAACCAAGAAAGGAAGGGAATTTGAAGGAGAAGAA

GAATATCTGGAGATCCTTGGCATCACCAGGGAGCAGTCAGGCAAATATGAGTGCAAAGCTGC

CAACGAGGTCTCCTCGGCGGATGTCAAACAAGTCAAGGTCACTGTGAACTATCCTCCCACTA

TCACAGAATCCAAGAGCAATGAAGCCACCACAGGACGACAAGCTTCACTCAAATGTGAGGCC

TCGGCAGTGCCTGCACCTGACTTTGAGTGGTACCGGGATGACACTAGGATAAATAGTGCCAA

TGGCCTTGAGATTAAGAGCACGGAGGGCCAGTCTTCCCTGACGTGACCAACGTCACTGAGAG

GNGAGCACTACGGCAACTACACCTGTGTGGCTGCCAACAAGCTGGGGGTCACAATGCCAGCC

TAGTCCTTTTCAGACNTGGKYSGTGAGAGGAATAAATGGATCCATCAGTCTGGCCGTACCAC

TNGTGGCTGCTGGCAGCAATNNTCTCTGCTCTGCCGTCTCAGCAAATGTTAATAGAATAAAA

ATTTAAAAATAATTTAAAAAACACACAAAAATGCGTCACACAGAATACAGAGAGAGAGAGAC

AGAGAGAGAGAGAGAGAGAGATGGGGGAGACCGTTTATTTCACAACTTTGTGTGTTTATA

CATGAAGGGGAAATAAGAAAGTGAAGAAGAAAATACAACATTTAAAACAATTTTACAGTCC

ATCATTAAAAATTTATGTATCATTCAGGATGGAGAAGGTTCTACTGGGATATGTTTATATCT

ACTAAGCAAATGTATGCTGTGTAAAGACTACACCACACTAAGGACATCTGGATGCTGTAAAA

ATAAGAGAAGAACCAGATGGATATTAAGCCCCCAACACACACTTTATCCTTCCTTCCTTCA

TCTTTTTTCATCTGTGGGGAAGAAAATAAGGTCTTGCCTTTGGTGTTTATATTTCCATAACC

TTTTAATTCTATTTTTCATTTGAGCTGACTTGTAGCCACTTCAGACTATCAATGGAATCTTA

TGTTGAGCCTTTCTCTGGCTTTCCTTCGTCCACTATCTCTCCAACTTTAGAGATCATCCCCT

CTCCCTCCAGT<u>GCGTTCTATCTCCCCACA</u>CCCACCCAAGCTTGGCGTAATC

-continued

Type 3: ZBTB20-E1C LSAMP-E4-E5-E6-E7
(SEQ ID NO: 34)

CAACGCAGAGTACATGGGACACAACATCAAGAGCAGGAAAATGGACTCATTAGGGAGGCAGG

CAGTCATTACCACTCACACTGTACTTCCAGGGAGACACCGATTATAAGAAGAGAAACTCAGC

GCTGGGGAAGAAGGAAGGGAATTTGAAGGAGAAGAAGAATATCTGGAGATCCTTGGCATCAC

*CAGGGAGCAGTCAGGCAAATATGAGTGCAAAGCTGCCAACGAGGTCTCCTCGGCGGATGTCA*

*AACAAGTCAAGGTCACTGTGAACTATCCTCCCACTATCACAGAATCCAAGAGCAATGAAGCC*

ACCACAGGACGACAAGCTTCACTCAAATGTGAGGCCTCGGCAGTGCCTGCACCTGACTTTGA

GTGGTACCGGGATGACACTAGGATAAATAGTGCCAATGGCCTTGAGATTAAGAGCACGGAGG

GCCAGTCTTCCCTGACGGTGACCAACGTCACTGAGGAGCACTACGGCAACTACACCTGTGTG

GCTGCCAACAAGCTGGGGGTCACCAATGCCAGCCTAGTCCTTTTCAGACCTGGGTCGGTGAG

AGGAATAAATGGATCCATCAGTCTGGCCGTACCACTGTGGCTGCTGGCAGCATCTCTGCTCT

GCCTTCTCAGCAAATGTTAATAGAATAAAAATTTAAAAATAATTTAAAAAACACACAAAAAT

GCGTCACACAGAATACAGAGAGAGAGACAGAGAGAGAGAGAGAGAGAGAGATGGGGGAGA

CCGTTTATTTCACAACTTTGTGTGTTTATACATGAAGGGGGAAATAAGAAAGTGAAGAAGAA

AATACAACATTTAAAACAATTTTACAGTCCATCATTAAAAATTTATGTATCATTCAGGATGG

AGAAGGTTCTACTGGGATATGTTTATATCTACTAAGCAAATGTATGCTGTGTAAAGACTACA

CCACACTAAGGACATCTGGATGCTGTAAAAATAAGAGAAGAACCAGATGGATATTAAGCCCC

CCAACACACACTTTATCCTTCCTTCCTTCATCTTTTTTCATCTGTGGGGAAGAAAATAAGGT

CTTGCCTTTGGTGTTTATATTTCCATAACCTTTTAATTCTATTTTTCATTTGAGCTGACTTG

TAGCCACTTCAGACTATCAATGGAATCTTATGTTGAGCCTTTCTCTGGCTTTCCTTCCTCCA

CTATCTCTCCAACTTTAGAGATCATCCCCTCTCCCTCCAGT<u>GCGTTCTATCTCCCCCACACC</u>

CACCCAAGCTTGGCGTAATC

Type 4: ZBTB20-E1-E1A-E1B-LSAMP-E4
(SEQ ID NO: 35)

ACATGGGGAAGTTTAGGAGTTGAGGAAAGAAGATTAAAGAGCGCGAGGA*GATTTTATAGACC*

*AGTGGAATACAGCCCTTGTGCATATGAAGATCAGGT GACAAGTTTGSTGCCTACCAGCCTCC*

*ACAGCAATATGCCCTTTCACG* AGTCCCTATCGCCCAGGCTGGAGTGCAGTGGCGTGATCTCT

GCTCACTGCAACCTCCGCCTCCCGGGTTCAAGTGATTCTCTTGCCTCAGCCTCCCGAGTAGC

TGGGATTACAGGA*AGGGAATTTGAAGGAGAAGAAGAATATCTGGAGATCCTT*<u>GG*CATCACCA*</u>

<u>*GGGAGCAGTCAGGCAAAA*</u>GCTTGGCGTAATC

Type 5: ZBTB20-E1*A-LSAMP-E4
(SEQ ID NO: 36)

ACATGGGGGAGGAAAGAAGATTAAAGAGCGCGAGGAGATTTTATAGACCAGTGGAATACAGG

CCTTGTGCATATGAAGATCAGGTGACAAGTTTGCTGCCTACCAGCCTCCACAGCAATATGCC

CTTTCACGGA*AGGGAATTTGAAGGAGAAGAAGAATATCTGGAGATCCTT*<u>GGCATCACCAGGG</u>

<u>AGCAGTCAGGCAAAA</u>GCTTGGCGTAATC

Type 6: ZBTB20-E1-E1B-LSAMP-E4
(SEQ ID NO: 37)

ACATGGGGGAGGAAAGAAGATTAAAGAGCGCGAGGAGACAG*AGTCCCTATCGCCCAG*

*GCTGGAGTGCAGTGGCGTGATCTCTGCTCACTGCAACCTCCGCCTCCCGGGTTCAAGTGATT*

*CTCTTGCCTCAGCCTCCCGAGTAGCTGGGATTACAGGAAGGGAATTTGAAGGAGAAGAAGAA*

*TATCTGGAGATCCTT*<u>GGCATCACCAGGGAGCAGTCAGGCAAAAG</u>

-continued

Type 7: ZBTB20-F1-LSAMP-E4

(SEQ ID NO: 38)

ACATGGGGAAGTTTAGGAGTTGAGGAAAGAAGATTAAAGAGCGCGAGGAGGAAGGGAATTTG
AAGGAGAAGAAGAATATCTGGAGATCCTTGGCATCACCAGGGAGCAGTCAGGCAAAAGCTTG
GSGTAATC

Type 8: ZBTB20-E1-LSAMP-E3*-E4

(SEQ ID NO: 39)

ACATGGGGGGGCGGGGGAAGTTTAGGAGTTGAGGAAAGAAGATTAAAGAGCGCGAGGAGAT

TAACTTACTCTTAATGATCTTCCAACACTTGAGAAGGTCAGTAGCCCTCCATCTGTCATTCT

CCAAGTTCACCAACAGCTTATCCACCCATCAAAGGTGCTTTTGTAACAAAATCCATGCATAA

TGAAACCAAGAAAGGAAGGGAATTTGAAGGAGAAGAAGAATATCTGGAGATCCTTGGCATCA

CCAGGGAGCAGTCAGGCAAAAGCTTGGCGTAATC

Type 9. ZETB20-E1C LSAMP-E4

(SEQ ID NO: 40)

**ACATGGGGAAGAGCAGGAAAATGGACTCATTAGGGAGGCAGGCAGTCATTACCACTCACACT
GTACTTCCAGGGAGACACCGATTATAAGAAGAGAAACTCAGCGCTGGGGAAGAAG**GAAGGGA

ATTTGAAGGAGAAGAAGAATATCTGGAGATCCTTGGCATCACCAGGGAGCAGTCAGGCAAAA

GCTTGGCGTAATC

Type 10: ZBTB20-E1C-LSAMP-E3*-E4

(SEQ ID NO: 41)

**ACATGGGGAGTACATGGGGATATACACAACATCAAGAGCAGGAAAATGGACTCATTAGGGAG

GCAGGCAGTCATTACCACTCACACTGTACTTCCAGGGAGACACCGATTATAAGAAGAGAAAC

TCAGCGCTGGGGAAGA**AGATTAACTTACTCTTAATGATCTTCCAACACTTGAGAAGGTCAGT

AGCCCTCCATCTGTCATTCTCCAAGTTCACCAACAGCTTATCCACCCATCAAAGGTGCTTTT

GTAACAAAATCCATGCATAATGAAACCAAGAAAGGAAGGGAATTTGAAGGAGAAGAAGAATA

TCTGGAGATCCTTGGCATCACCAGGGAGCAGTCAGGCAAAAGCTTGGCGTAATC

LPCS1: LSAMP-E0*-E1-E2-E3-E4

(SEQ ID NO: 46)

GGAGGAGGATAGGAAGCAGGAAAGCGGGAGAGCTCGAGGGACAAGGGGGCTCGGTGTGTTTA

CACCAGGCACGGGCTACGAGCGTCCATCCCGGCCCCTGGCTTGCGCTCCCGAAGAGGAGAGC

AAGGCTGTTCTGGGATCCGGCCGTCGTGCGGCAAGAGGCTTGTCTGTCCGGGTTGCCGGAAC

CAGGAGAACCCAGAGGGAAACCGAGGGAAAGGAGCGGCGCGTTTTACTAGAGAGAGCGCGAG

CGGAAGAGGCGAGAGCAGGAGCGCGCGAGGGAGCATCGAGCGCAGCGGAGACATGAGGACCT

ACTGGCTGCACAGCGTCTGGGTGCTGGGCTTTTTCCTGTCCCTCTTCTCATTGCAAGGACTG

CCTGTTCGCAGCGTGGATTTTAACCGAGGCACGGACAACATCACCGTGAGGCAGGGGACAC

AGCCATCCTCAGGTGCGTTGTAGAAGACAAGAACTCAAAGGTGGCCTGGTTGAACCGTTCTG

GCATCATTTTTGCTGGACATGACAAGTGGTCTCTGGACCCACGGGTTGAGCTGGAGAAACGC

CATTCTCTGGAATACAGCCTCCGAATCCAGAAGGTGGATGTCTATGATGAGGGTTCCTACAC

TTGCTCAGTTCAGACACAGCATGAGCCCAAGACCTCCCAAGTTTACTTGATCGTACAAGTCC

CACCAAAGATCTCCAATATCTCCTCGGATGTCACTGTGAATGAGGGCAGCAACGTGACTCTG

GTCTGCATGGCCAATGGCCGTCCTGAACCTGTTATCACCTGGAGACACCTTACACCAACTGG

AAGGGAATTTGAAGGAGAAGAAGAATATCTGGAGATCCTTGGCATCACCAGGGAGCAGTCAG

GCAAAAGCTTGGCGTAATCC

All cDNA sequences were distinct from the wild type LSAMP and ZBTB20 sequences. Seven of the ten fusion transcripts involved a fusion between exon 1 of ZBTB20 and exon 4 of LSAMP. FIG. 5. The remaining three fusion transcripts involved a fusion between exon 1 of ZBTB20 and exon 3* of LSAMP. FIG. 5. Exon 3* represents a novel exon sequence from the LSAMP locus that has not been previously annotated and that is associated with the genomic rearrangement of the ZBTB20 and LSAMP genes. The nucleotide sequence of exon 3* corresponds to SEQ ID NO:45. Open reading frame (ORF) searches predicted severe N-terminal truncation of the LSAMP protein or the absence of ORF in the LSAMP cDNA.

One of ordinary skill in the art can design primers for amplifying these ZBTB20/LSAMP gene fusion transcripts. In one embodiment, the forward primer is designed to hybridize to a region of exon 1 of ZBTB20 (e.g., E1, E1A, E1B, or E1C) and the reverse primer is designed to hybridize to exon 3* or exon 4 of LSAMP. In another embodiment, the primers are designed to amplify an amplification product that comprises a first region from exon 1 of ZBTB20 (e.g., E1, E1A, E1B, or E1C) and a second region from exon 3* or exon 4 of LSAMP, wherein detecting the amplification product indicates the presence of a ZBTB20/LSAMP gene fusion transcript. In certain embodiments, the forward primer hybridizes under conditions of high stringency to a region within E1 of the ZBTB20 gene and the reverse primer (e.g., SEQ ID NO:44) hybridizes under conditions of high stringency to a region within exon 4 of LSAMP. Exon 4 of LSAMP corresponds to nucleotides 1022-1156 of SEQ ID NO: 10. These primers could be used to amplify, for example, the Type 1, 4, 5, 6, 7, and 8 fusion transcripts in FIG. 5. In other embodiments, the forward primer hybridizes under stringent conditions to a region within E1C of the ZBTB20 gene and the reverse primer (e.g., SEQ ID NO:44) hybridizes under stringent conditions to a region within exon 4 of LSAMP. These primers could be used to amplify, for example, the Type 2, 3, 9, and 10 fusion transcripts in FIG. 5. In certain embodiments, the reverse primer (e.g., SEQ ID NO:42 or SEQ ID NO:43) hybridizes to a region within exon 7 of LSAMP or a sequence complementary thereto. Because exon 3* is a unique LSAMP exon associated with the genomic arrangement of the ZBTB20 and LSAMP genes, it is also possible to design primers to amplify unique regions of exon 3* or a unique region that spans the junction between exon 3* and exon 4 of LSAMP and, thus, can be used to specifically identify the genomic arrangement of the ZBTB20 and LSAMP genes.

LPCS1 (SEQ ID NO:46) represents an alternatively spliced cDNA of the LSAMP locus and includes exon 0*, a novel exon sequence from the LSAMP locus that has not been previously annotated and that is associated with the genomic rearrangement of the ZBTB20 and LSAMP genes. The nucleotide sequence of exon 0* corresponds to SEQ ID NO:47. Because exon 0* is a unique LSAMP exon associated with the genomic arrangement of the ZBTB20 and LSAMP genes, one of skill in the art can design primers to amplify unique regions of exon 0* or a unique region that spans the junction between exon 0* and exon 1 of LSAMP and, thus, can be used to specifically identify the genomic arrangement of the ZBTB20 and LSAMP genes.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

The following references are cited in the application and provide general information on the field of the invention and provide assays and other details discussed in the application. The following references are incorporated herein by reference in their entirety.

1. Siegel, R.; Naishadham, D.; Jemal, A. Cancer statistics. *CA Cancer J. Clin.* 2013, 63, 11-30.
2. Chornokur, G.; Dalton, K.; Borysova, M. E.; Kumar, N. B. Disparities at presentation, diagnosis, treatment, and survival in African American men affected by prostate cancer. *Prostate* 2011, 71, 985-997.
3. Schwartz, K.; Powell, I. J.; Underwood, W., 3rd; George, J.; Yee, C.; Banerjee, M. Interplay of race, socioeconomic status, and treatment on survival of patients with prostate cancer. *Urology* 2009, 74, 1296-1302.
4. Major, J. M.; Oliver, M. N.; Doubeni, C. A.; Hollenbeck, A. R.; Graubard, B. I.; Sinha, R. Socioeconomic status, healthcare density, and risk of prostate cancer among African American and Caucasian men in a large prospective study. *Cancer Causes Control* 2012, 23, 1185-1191.
5. Sridhar, G.; Masho, S. W.; Adera, T.; Ramakrishnan, V.; Roberts, J. D. Do African American men have lower survival from prostate cancer compared with White men?A meta-analysis. *Am. J Mens. Health* 2010, 4, 189-206.
6. Cullen, J.; Brassell, S.; Chen, Y.; Porter, C.; L'Esperance, J.; Brand, T.; McLeod, D. G. Racial/ethnic patterns in prostate cancer outcomes in an active surveillance cohort. *Prostate Cancer* 2011, 2011, doi: 10.1155/2011/234519.
7. Berger, A. D.; Satagopan, J.; Lee, P.; Taneja, S. S.; Osman, I. Differences in clinicopathologic features of prostate cancer between black and white patients treated in the 1990s and 2000s. *Urology* 2006, 67, 120-124.
8. Kheirandish, P.; Chinegwundoh, F. Ethnic differences in prostate cancer. *Br. J. Cancer* 2011, 105, 481-485.
9. Odedina, F. T.; Akinremi, T. O.; Chinegwundoh, F.; Roberts, R.; Yu, D.; Reams, R. R.; Freedman, M. L.; Rivers, B.; Green, B. L.; Kumar, N. Prostate cancer disparities in black men of African descent: A comparative literature review of prostate cancer burden among black men in the United States, Caribbean, United Kingdom, and West Africa. *Infect. Agents Cancer* 2009, 4, doi:10.1186/1750-9378-4S1-S2.
10. Heath, E. I.; Kattan, M. W.; Powell, I. J.; Sakr, W.; Brand, T. C.; Rybicki, B. A.; Thompson, I. M.; Aronson, W. J.; Tenrris, M. K.; Kane, C. J.; et al. The effect of race/ethnicity on the accuracy of the 2001 Partin Tables for predicting pathologic stage of localized prostate cancer. *Urology* 2008, 71, 151-155.
11. Moul, J. W.; Sesterhenn, I. A.; Connelly, R. R.; Douglas, T.; Srivastava, S.; Mostofi, F. K.; McLeod, D. G. Prostate-specific antigen values at the time of prostate cancer diagnosis in African-American men. *JAMA* 1995, 274, 1277-1281.
12. Tewari, A.; Horninger, W.; Badani, K. K.; Hasan, M.; Coon, S.; Crawford, E. D.; Gamito, E. J.; Wei, J.; Taub, D.; Montie, J.; et al. Racial differences in serum prostate-specific (PSA) doubling time, histopathological variables and long-term PSA recurrence between African-American and white American men undergoing radical prostatectomy for clinically localized prostate cancer. *BJU Int.* 2005, 96, 29-33.

13. Wallace, T. A.; Prueitt, R. L.; Yi, M.; Howe, T. M.; Gillespie, J. W.; Yfantis, H. G.; Stephens, R. M.; Caporaso, N. E.; Loffredo, C. A.; Ambs, S. Tumor immunobiological differences in prostate cancer between African-American and Caucasian-American men. *Cancer Res.* 2008, 68, 927-936.
14. Prensner, J. R.; Rubin, M. A.; Wei, J. T.; Chinnaiyan, A. M. Beyond PSA: The next generation of prostate cancer biomarkers. *Sci. Transl. Med.* 2012, 4, doi: 10.1126/scitranslmed.3003180.
15. Rubin, M. A.: Maher, C. A.; Chinnaiyan, A. M. Common gene rearrangements in prostate cancer. *J. Clin. Oncol.* 2011, 29, 3659-3668.
16. Sreenath, T. L.; Dobi, A.; Petrovics, G.; Srivastava, S. Oncogenic activation of ERG: A predominant mechanism in prostate cancer. *J. Carcinog.* 2011, 11, 10-21.
17. Petrovics, G.; Liu, A.; Shaheduzzaman, S.; Furasato, B.; Sun, C.; Chen, Y.; Nau, M. Ravindranath, L.; Chen, Y.; Dobi, A.; et al. Frequent overexpression of ETS-related gene-1 (ERG1) in prostate cancer transcriptome. *Oncogene* 2005, 24, 3847-3852.
18. Tomlins, S. A.; Rhodes, D. R.; Perner, S.; Dhanasekaran, S. M.; Mehra, R.; Sun, X. W.; Varambally, S.; Cao, X.; Tchinda, J.; Kuefer, R.; et al. Recurrent fusion of TMPRSS2 and ETS transcription factor genes in prostate cancer. *Science* 2005, 310, 644-648.
19. Magi-Galluzzi, C.; Tsusuki, T.; Elson, P.; Simmerman, K.; LaFarque, C.; Esqueva, R.; Klein, E.; Rubin, M. A.; Zhou, M. TMPRSS2-ERG gene fusion prevalence and class are significantly different in prostate cancer of Caucasian, African-American and Japanese patients. *Prostate* 2011, 71, 489-497.
20. Rosen, P.; Pfister, D.; Young, D.; Petrovics, G.; Chen, Y.; Cullen, J.; Bohm, D.; Pemer, S.; Dobi, A.; McLeod, D. G.; et al. Differences in frequency of ERG oncoprotein expression between index tumors of Caucasian and African American patients with prostate cancer. *Urology* 2012, 80, 749-753.
21. Hu, Y.; Dobi, A.; Sreenath, T.; Cook, C.; Tadase, A. Y.; Ravindranath, L.; Cullen, J.; Furusato, B.; Chen, Y.; Thanqapazham, R. L.; et al. Delineation of TMPRSS2-ERG splice variants in prostate cancer. *Clin. Cancer Res.* 2008, 14, 4719-4725.
22. Gary K Geiss, et al. (2008) Direct multiplexed measurement of gene expression with color-coded probe pairs, *Nature Biotecmology* 26:317-25.
23. Paolo Fortina and Saul Surrey, (2008) Digital mRNA Profiling, *Nature Biotechnology* 26:317-25.
Farrell J, Petrovics G, McLeod D G, Srivastava S.: Genetic and molecular differences in prostate carcinogenesis between African American and Caucasian American men. *International Journal of Molecular Sciences.* 2013; 14(8): 15510-31.
25. Rodriquez-Suarez et al., Urine as a source for clinical proteome analysis: From discovery to clinical application, *Biochimica et Biophysica Acta* (2013).
26. Shi et al., Antibody-free, targeted mass-spectrometric approach for quantification of proteins at low picogram per milliliter levels in human plasma/serum, *PNAS,* 109 (38):15395-15400 (2012).
27. Elentiboba-Johnson and Lim, Fusion peptides from oncogenic chimeric proteins as specific biomarkers of cancer, *Mol Cell Proteomics,* 12:2714 (2013).
28. Ras/Raf/MEK/ERK and PI3K/PTEN/Akt/mTOR Cascade Inhibitors: How Mutations Can Result in Therapy Resistance and How to Overcome Resistance, *Oncotarget,* 3(10):1068-1111 (2012).
29. Kuhn et al., High-resolution genomic profiling of adult and pediatric core-binding factor acute myeloid leukemia reveals new recurrent genomic alterations, Blood, 119 (10):e67 (2012).
30. Pasic et al., Recurrent Focal Copy Number Changes and Loss of Heterozygosity Implicate Two Non-Coding RNAs and One Tumor Suppressor Gene at Chromosome 3q13.31 in Osteosarcoma, Cancer Research, 70(1):160-71 (2010).
31. Chen et al., The t(1; 3) breakpoint-spanning genes LSAMP and NORE1 are involved in clear cell renal cell carcinomas, Cancer Cell, 4:405-413 (2003).
32. Ntougkos et al., Clin Cancer Res, 11:5764-5768 (2005).
33. Huang et al., Eur J Cancer 49:3729-37 (2013).
34. Mao et al., Cancer Res, 70:5207-5212 (2010).
35. Blattner et al., Neoplasia 16(1):14-20 (2014).
36. Khani et al., Clin Cancer Res 20(18):4925-34 (2014).

What is claimed:

1. A method of detecting a genomic rearrangement in a biological sample, the method comprising detecting the genomic rearrangement in the biological sample obtained from a subject, wherein the subject is a human and wherein the biological sample comprises prostate cells or nucleic acid or polypeptides isolated from the prostate cells and wherein the genomic rearrangement occurs in chromosome region 3q13 and is a gene fusion, a gene deletion, or a gene duplication of a ZBTB20 gene and an LSAMP gene and wherein detecting the genomic rearrangement in the biological sample comprises:
   (a) detecting a gene duplication that results in a fusion between exon 1 of the ZBTB20 gene and exon 4 of the LSAMP gene;
   (b) detecting a fusion between exon 1 of the ZBTB20 gene and exon 3* of the LSAMP gene; or
   (c) detecting a deletion in chromosome region 3q13, wherein the deletion spans both the ZBTB20 and LSAMP genes or results in a fusion between the ZBTB20 and LSAMP genes.

2. The method of claim 1, wherein the subject self-identifies as being of African descent.

3. The method of claim 1, wherein detecting the presence of the genomic rearrangement in the biological sample comprises detecting a deletion in chromosome region 3q13, wherein the deletion spans the ZBTB20 and LSAMP genes.

4. The method of claim 1, wherein detecting the presence of the genomic rearrangement in the biological sample comprises detecting a mRNA or cDNA transcript comprising SEQ ID NO: 47 or SEQ ID NO:45.

5. The method of claim 1, wherein detecting the genomic rearrangement in the biological sample comprises hybridizing a probe under high stringency conditions to a junction of a chimeric nucleic acid, wherein the chimeric nucleic acid comprises a first portion from a ZBTB20 gene and a second portion from a LSAMP gene, and wherein the probe detects a deletion involving a fusion between the ZBTB20 gene and the LSAMP gene.

6. The method of claim 1, wherein detecting the presence of the genomic rearrangement in the biological sample comprises hybridizing a probe under high stringency conditions to the chromosome region 3q13, wherein the probe detects a deletion spanning both the ZBTB20 and LSAMP genes.

* * * * *

SEQUENCE LISTING

<160> NUMBER OF SEQ ID NOS: 50

<210> SEQ ID NO 1
<211> LENGTH: 602
<212> TYPE: DNA
<213> ORGANISM: Homo sapiens

<400> SEQUENCE: 1

```
ctcgagaaca gtgagcaata aattttctt tatacattac ccagtctgtg gtattctgtt      60
atggcaacac aaaataaact aagacagtat tatgtatttt ttcttttgtt ttacatttta     120
ctaagtgccg acttattcga aaaggtaatt agctttggtt aattatcaaa gttttgtctt     180
tcctttccta cttttgtccc actaagcaaa aaacaaaaca atgagcattg acctttacct     240
ttctctggta agggagtatg gaaggttttc tactactttg taaaaatact gctacagatg     300
gagagtctct tctttgggtc tcttccacat agcttgtttg taatctccaa gaaagacttc     360
acattacagg ctgaaaagaa tcacctacgg tttccatatt ttgaaagaaa ttttaaaaa     420 ccatgaaaac aaacaaacaa aaatcctagt ttcctttata aaatagcaaa ggaaagttct     480
```

```
ctctcctgtc accaggaata tgattatgat cagttggtta tttaggtcac atgtgaaaga      540
aatgaaagag gaggcatggg aatgtaaggg agaatagtag tctgccctca agtctgcaaa      600
cg                                                                    602

<210> SEQ ID NO 2
<211> LENGTH: 301
<212> TYPE: DNA
<213> ORGANISM: Homo sapiens

<400> SEQUENCE: 2
agagtctctt ctttgggtct cttccacata gcttgtttgt aatctccaag aaagacttca       60
cattacaggc tgaaaagaat cacctacggt ttccatattt tgaaagaaat ttttaaaaac      120
catgaaaaca aacaaacaaa aatcctagtt tcctttataa aatagcaaag gaaagttctc      180
tctcctgtca ccaggaatat gattatgatc agttggttat ttaggtcaca tgtgaaagaa      240
atgaaagagg aggcatggga atgtaaggga gaatagtagt ctgccctcaa gtctgcaaac      300
g                                                                    301

<210> SEQ ID NO 3
<211> LENGTH: 301
<212> TYPE: DNA
<213> ORGANISM: Homo sapiens

<400> SEQUENCE: 3
ctcgagaaca gtgagcaata aattttctt tatacattac ccagtctgtg gtattctgtt       60
atggcaacac aaaataaact aagacagtat tatgtatttt ttcttttgtt ttacatttta      120
ctaagtgccg acttattcga aaaggtaatt agctttggtt aattatcaaa gttttgtctt      180
tcctttccta cttttgtccc actaagcaaa aaacaaaaca atgagcattg acctttacct      240
ttctctggta agggagtatg gaaggttttc tactactttg taaaaatact gctacagatg      300
g                                                                    301

<210> SEQ ID NO 4
<211> LENGTH: 621
<212> TYPE: DNA
<213> ORGANISM: Homo sapiens

<400> SEQUENCE: 4
cacaacatca agagcaggaa aatggactca ttagggaggc aggcagtcat taccactcac       60
actgtacttc cagggagaca ccgattataa gaagagaaac tcagcgctgg ggaagaagga      120
agggaatttg aaggagaaga agaatatctg gagatccttg gcatcaccag ggagcagtca      180
ggcaaatatg agtgcaaagc tgccaacgag gtctcctcgg cggatgtcaa acaagtcaag      240
gtcactgtga actatcctcc cactatcaca gaatccaaga gcaatgaagc caccacagga      300
cgacaagctt cactcaaatg tgaggcctcg gcagtgcctg cacctgactt tgagtggtac      360
cgggatgaca ctaggataaa tagtgccaat ggccttgaga ttaagagcac ggagggccag      420
tcttccctga cggtgaccaa cgtcactgag gagcactacg gcaactacac ctgtgtggct      480
gccaacaagc tggggtcac caatgccagc ctagtccttt tcagacctgg gtcggtgaga      540
ggaataaatg gatccatcag tctggccgta ccactgtggc tgctggcagc atctctgctc      600
tgccttctca gcaaatgtta a                                               621

<210> SEQ ID NO 5
<211> LENGTH: 118
```

-continued

```
<212> TYPE: DNA
<213> ORGANISM: Homo sapiens

<400> SEQUENCE: 5
cacaacatca agagcaggaa aatggactca ttagggaggc aggcagtcat taccactcac   60
actgtacttc cagggagaca ccgattataa gaagagaaac tcagcgctgg ggaagaag    118

<210> SEQ ID NO 6
<211> LENGTH: 503
<212> TYPE: DNA
<213> ORGANISM: Homo sapiens

<400> SEQUENCE: 6
gaagggaatt tgaaggagaa gaagaatatc tggagatcct tggcatcacc agggagcagt   60
caggcaaata tgagtgcaaa gctgccaacg aggtctcctc ggcggatgtc aaacaagtca  120
aggtcactgt gaactatcct cccactatca cagaatccaa gagcaatgaa gccaccacag  180
gacgacaagc ttcactcaaa tgtgaggcct cggcagtgcc tgcacctgac tttgagtggt  240
accgggatga cactaggata aatagtgcca atggccttga gattaagagc acggagggcc  300
agtcttccct gacggtgacc aacgtcactg aggagcacta cggcaactac acctgtgtgg  360
ctgccaacaa gctgggggtc accaatgcca gcctagtcct tttcagacct gggtcggtga  420
gaggaataaa tggatccatc agtctggccg taccactgtg gctgctggca gcatctctgc  480
tctgccttct cagcaaatgt taa                                           503

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcaggcagtc attaccactc                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgacttgttt gacatccgcc                                                20

<210> SEQ ID NO 9
<211> LENGTH: 338
<212> TYPE: PRT
<213> ORGANISM: Homo sapiens

<400> SEQUENCE: 9

Met Val Arg Arg Val Gln Pro Asp Arg Lys Gln Leu Pro Leu Val Leu
1               5                   10                  15

Leu Arg Leu Leu Cys Leu Leu Pro Thr Gly Leu Pro Val Arg Ser Val
                20                  25                  30

Asp Phe Asn Arg Gly Thr Asp Asn Ile Thr Val Arg Gln Gly Asp Thr
            35                  40                  45

Ala Ile Leu Arg Cys Val Val Glu Asp Lys Asn Ser Lys Val Ala Trp
```

```
                    50                  55                  60
        Leu Asn Arg Ser Gly Ile Ile Phe Ala Gly His Asp Lys Trp Ser Leu
        65                  70                  75                  80

Asp Pro Arg Val Glu Leu Glu Lys Arg His Ser Leu Glu Tyr Ser Leu
                        85                  90                  95

Arg Ile Gln Lys Val Asp Val Tyr Asp Gly Ser Tyr Thr Cys Ser
                    100                 105                 110

Val Gln Thr Gln His Glu Pro Lys Thr Ser Gln Val Tyr Leu Ile Val
                    115                 120                 125

Gln Val Pro Pro Lys Ile Ser Asn Ile Ser Ser Asp Val Thr Val Asn
                130                 135                 140

Glu Gly Ser Asn Val Thr Leu Val Cys Met Ala Asn Gly Arg Pro Glu
        145                 150                 155                 160

Pro Val Ile Thr Trp Arg His Leu Thr Pro Thr Gly Arg Glu Phe Glu
                        165                 170                 175

Gly Glu Glu Glu Tyr Leu Glu Ile Leu Gly Ile Thr Arg Glu Gln Ser
                    180                 185                 190

Gly Lys Tyr Glu Cys Lys Ala Ala Asn Glu Val Ser Ser Ala Asp Val
                    195                 200                 205

Lys Gln Val Lys Val Thr Val Asn Tyr Pro Pro Thr Ile Thr Glu Ser
                    210                 215                 220

Lys Ser Asn Glu Ala Thr Thr Gly Arg Gln Ala Ser Leu Lys Cys Glu
        225                 230                 235                 240

Ala Ser Ala Val Pro Ala Pro Asp Phe Glu Trp Tyr Arg Asp Asp Thr
                        245                 250                 255

Arg Ile Asn Ser Ala Asn Gly Leu Glu Ile Lys Ser Thr Glu Gly Gln
                    260                 265                 270

Ser Ser Leu Thr Val Thr Asn Val Thr Glu Glu His Tyr Gly Asn Tyr
                    275                 280                 285

Thr Cys Val Ala Ala Asn Lys Leu Gly Val Thr Asn Ala Ser Leu Val
                    290                 295                 300

Leu Phe Arg Pro Gly Ser Val Arg Gly Ile Asn Gly Ser Ile Ser Leu
        305                 310                 315                 320

Ala Val Pro Leu Trp Leu Leu Ala Ala Ser Leu Leu Cys Leu Leu Ser
                        325                 330                 335

Lys Cys

<210> SEQ ID NO 10
<211> LENGTH: 9478
<212> TYPE: DNA
<213> ORGANISM: Homo sapiens

<400> SEQUENCE: 10
ggaggagggg gagagaggct ctgggttgct gctgcttctg ctgctgctgc tgctgtgtgg      60
ctgtttctgt acactcactg gcaggcttgg tgccggctcc ctcgcccgcc cgcccgccag     120
cctgggaaag tgggttacag agcgaaggag ctcagctcag acactggcag aggagcatcc     180
agtcacagag agaccaaaca gaaccctttc ctttggcttc ctcttcagcc tcttccagag     240
ggcttgctat ttgcactctc tcttttgaaa ttgtgttgct tttactttc acccttctgc      300 ttgggtttta tgagggcttt gttaagtctt agagggaaaa gagactgagc gagggaaaga     360
gagaggcaaa gtgaaagga ccataaactg gcaaagcccg ctctgcgctc gctgtggatg      420
aaagccccgt gttggtgaag cctctcctcg cgagcagcgc gcaccccctcc agagcacccc     480
```

```
gcggacccgc acctcggcgt ggccaccatg gtcaggagag ttcagccgga tcggaaacag    540
ttgccactgg tcctactgag attgctctgc cttcttccca caggactgcc tgttcgcagc    600
gtggatttta accgaggcac ggacaacatc accgtgaggc agggggacac agccatcctc    660
aggtgcgttg tagaagacaa gaactcaaag gtggcctggt tgaaccgttc tggcatcatt    720
tttgctggac atgacaagtg gtctctggac ccacggggttg agctggagaa acgccattct   780
ctggaataca gcctccgaat ccagaaggtg gatgtctatg atgagggttc ctacacttgc    840
tcagttcaga cacagcatga gcccaagacc tcccaagttt acttgatcgt acaagtccca    900
ccaaagatct ccaatatctc ctcggatgtc actgtgaatg agggcagcaa cgtgactctg    960
gtctgcatgg ccaatggccg tcctgaacct gttatcacct ggagacacct tacaccaact   1020
ggaagggaat tgaaggaga agaagaatat ctggagatcc ttggcatcac cagggagcag    1080
tcaggcaaat atgagtgcaa agctgccaac gaggtctcct cggcggatgt caaacaagtc   1140
aaggtcactg tgaactatcc tcccactatc acagaatcca agagcaatga agccaccaca   1200
ggacgacaag cttcactcaa atgtgaggcc tcggcagtgc ctgcacctga ctttgagtgg   1260
taccgggatg acactaggat aaatagtgcc aatggccttg agattaagag cacggagggc   1320
cagtcttccc tgacggtgac caacgtcact gaggagcact acggcaacta cacctgtgtg   1380
gctgccaaca gctgggggt caccaatgcc agcctagtcc ttttcagacc tgggtcggtg    1440
agaggaataa atggatccat cagtctggcc gtaccactgt ggctgctggc agcatctctg   1500
ctctgccttc tcagcaaatg ttaatagaat aaaaatttaa aataattta aaaacacac     1560
aaaaatgcgt cacacagaat acagagagag agacagag agagagagag agagagat       1620
gggggagacc gtttatttca caactttgtg tgtttataca tgaagggga ataagaaag     1680
tgaagaagaa aatacaacat ttaaaacaat tttacagtcc atcattaaaa atttatgtat   1740
cattcaggat ggagaaggtt ctactgggat atgtttatat ctactaagca aatgtatgct   1800
gtgtaaagac tacaccacac taaggacatc tggatgctgt aaaataaga gaagaaccag    1860
atggatatta agccccccaa cacacacttt atccttcctt ccttcatctt ttttcatctg   1920
tggggaagaa aataaggtct tgcctttggt gtttatattt cataacctt ttaattctat    1980
ttttcatttg agctgacttg tagccacttc agactatcaa tggaatctta tgttgagcct   2040
ttctctggct ttccttcctc cactatctct ccaactttag agatcatccc ctctccctcc   2100
agtgcgttct atctcccccca cacccaccct agatactccc ttttcaccca cctttcctcc   2160
ctcacctctc ctcacctcca cccctcccc agagcactag tcatgccgca aatgctagga   2220
agtgccattt tcatttctc cactgtgcgt gtgtgctcaa gtctttcgct ctcacgtggg   2280
tgtacatgtg tgtgagcgtg tgtgtgtctc tctctaaagc atgccaaggg aatggtccat   2340
gtgtacatag actcattgtg ctgtagatac tgtcctgcat tgtaattgtg agatgcggct   2400
gtaacaagtt gctgggggag atggcgggga aagaggcaag gagcagagtc ctccctacat   2460
ccatggctgt cacatggcat cagtgtgtat tcaaaccaag ctatgctcct tccaagggca   2520
ggacccata ttcctcctag tccatcatc agaaccgagt ggggagtcac tcagaatatc     2580
actgtaaatg aaagtgccta ctatcgatgg ggtaagcaaa cagcataagg aattatgacg   2640
tggacgaggt gacctaggag agaaaatttc agattttact ctcatttcat gagtctgagg   2700
gattcttata tttcctggca tttaacaggg taggccctgc tccactgtga aaatgagcag   2760
catgtgttga gtaaatcccc agaaacagga aggtctccaa gtgtcaactc ccagtgaaag   2820
aatgatgaac cacttggaga tcctaagcag ccctgtttta cctcctccct aatcttaaat   2880
```

```
aacatttgtc ccatgaattc ccctgagcag agattgtttc ctatttcaga taaaatacag   2940
tgaaagtgag caaggcagaa aaagtcaaca gatgcccagg ctcctactgt attctggaga   3000
tactgtcaga gctctaatac agagcactgg ccataatgaa aagcagttca ctccttgtgc   3060
tcctctgcag atgtttttcc cagtgttcta ggttaatgtt ttatttggtt gcctgcataa   3120
tccctgttct gtttcactga tggtgtttgc agcaccactg ttcatggtgg tccactgtta   3180
tcctatgcca gggtgctaag aattgcatga tattcatctt ccctgctcta tttaaattta   3240
catctataag agtcatcttg acattaacac tgaaatgtga tctaggtcct taaccaaaat   3300
tgctgggcaa cttgtaataa atttagacag aaatttatg agtaccacaa agcttggtgt    3360
taccacatca ccagaaggat ttcttaggaa atgtcttgcc gagagagctg gctctctgca   3420
tatagatgtc tttgtcagaa aaccaaccct tgctctcact tacacagtag taagcactga   3480
aagtggttca gttcatgaga ggacagagaa ttattttgag attatatttg aatgtaatct   3540
tgcagagcca aatatggtat gtcattaagt tggaaccttg taaatagctg ttccatgtta   3600
taaaatgaga aactttgtaa ctggaaaaaa agaaaggaaa gaaggaagga aggaaggaag   3660
gaaggcaggg aggggggggac ggggaagggg gggagggagg gagggaggga gggagggagg   3720
gagggaggga ggaaggaagg aaggaaggaa ggaaggagaa aggaaaggaa ggcaggaggg   3780
agaaagatct aagtagcatt gttaatttct tcaatttctt ctaagggatt ttattgtttg   3840
ttttagaagc ttatcacagc cttctttcat gattttgcag tttagacttg atacaaggaa   3900
aaattcagct tggggatggt taagagtgtt tatagcagat tctgacatag gagagaaaac   3960
aaattctcat ccaagaaggt agctagtaaa atataggaa ggtgagccat attcctatgc    4020
agcatcaatt tattgacaat caggtatttc tcttaacagt ttggtcttct tagttcaaga   4080
ataaagggta tcatctttaa taataagcat tccccaaaaa ttgaagaggc agtcacacac   4140
ttaagtgtgt ggctttagaa aagcgcatgc taatttaaag atatacagga agagaaaagt   4200
aggagttaag ttggatgttg ttagaagttg gatgttagta ttaccttcag gaacagatcc   4260
ccatggcatg tcacaggcct taattatata cctggctttc ttattgtctc cactttatca   4320
tgaggacaag gtcttggttt catgggagga acttctccat tgaaataaat gtctgccatg   4380
tcagcaccgt ttgttccctc agttttaata taatggacca tatattaaac ataattaaac   4440
atatatttaa atgtggtgtt tgcctgtgtc tctagcagga tcttgaaatt ttaaaaattt   4500
gcttctggtt cctgtttcag agaaaacatt gtccccagaa atttcatagg attgaaagtg   4560
ttccctaagc agtgtgaaca atggaggaaa atatagttta gagaaaagtc agggaaaggt   4620
agggccagag gactgacacc aagaaatcat tgaatctcaa cataagactt cttggaattt   4680
agttaatcat attggaataa attccttcaa gaatcttgtc ccttggtaat caaagtttga   4740
aaccccgcac tgaaaagcac caactggttg gaaataatat actgagagga gtgaaattca   4800
tcaattaatc tgagtggcta atatatttaa tatcctttgt atacaaagta aaactccacc   4860
attcgtaaaa ggaaatcctt agacccaact ttcagttaac aaaaacagaa atgactttga   4920
cccagggtgc ttcctgaaga atgagaacta tccagggctt tacaactgca gaattgtaat   4980
tatgctctgt gcaattgttg agcaaaggtt ttgccttgct ggataaaaag tcttgtttgt   5040
ttcgagacat gaaatcccca tgtcttaaaa gaactaaggc ttatagaaaa gcagatgggt   5100
tttctctcag gaaggactgc cccattgacc tttgccttct cttccaagtc agacagactt   5160
ctcgcttgcc atgggcattt ttttactaca tagtcagact actggggcta cttatagaga   5220
```

```
ccttgtaaaa gtactcgtga ttttcacgtt cttggaggac caaacaaaaa tctgtttctc    5280
ctccaaaaat ggacttacct cctttgcaca caaaagctaa actcctcagc atgaaattgt    5340
ttgagttatt actttaccaa gttgtgagct tcttgaatcc tccagagtcg cagattccat    5400
ccctgagttg gttgtggttt cactgtttct attggctatt ctccctgaat ttttcatttt    5460
gttctttgca gggctcgaat tatttgtgga aaacaataat atatatgtgt gtgtatttt     5520 tatctttata gatgctatat ttacaataat gtatgtatta aagacaaat taagaataat    5580 gttttgatct aaaaggaag aaaagtactg aatttggttg tttagaaaga aaatctatgc     5640
tcacgtagaa agacatagag ccccacttt tccgttttgt aattatttgg cgaaaagaaa     5700
tttgcttata gactatgttt aatgggatta accatgtcct catttttctt ttcatcctca    5760
tcacttttta gcctgcattt agtcttggtt accaatatca tttttaaga gaatgtaag      5820 tacagtgcta tatcttacct acataaacta ttaatatttt gaagacaaat gtgaaacaca    5880
ccacaaaaat ggtgagataa gaaacaaaaa tgcagtttag gaagcctcct ccttgcttaa    5940
atgtttagaa tatttcttct ccaaagactg catttgcctc agtgatgtaa attttccatc    6000
atggttggca taatatctgt aaacatctca ctaaatgcaa aatggagttt acatttatgt    6060
gcatactagc agaaaagaag taaactattc tcatttgcat gtagctatgc tgttcaaatg    6120
tcgccaacca aaatttagga aagaatttgt tttcacccag catgtacatc tcacttttct    6180 cttgcaagg aagctggtgt taacgttggg tttaggttta acatttacac cagcgaaaat    6240
gtttatgaat attatggaaa acttatttta aaccttgatt tcttttgagc acatttacat    6300
gctgcgtgct gattaataaa ttaggcacca atcatgtgta aatcaatgta aatcactagt    6360
ttatgtacat aatataaact atgtaaactt catttttcat gcagtgccca actactgcta    6420
aggtttacta tgattcttaa ggaaaaaaaa atcaaataaa aataaataaa aactgaaacg    6480
tttcacagtt cagaatcgga agaattacga ctaaagctcc aaatatgagg ttgccttagc    6540
caaaggaagc agacccacag gaacagttca aggtttatat cctgctcaag tcacctcttt    6600
ggtctttcag gatctaagtg gagattgtcc caactgttgc tgtagttgtc tcacccgacc    6660
ccaaagcaag ggaaatagag ggaaggttt taagggctat atgtctgctg tatccactcc    6720
cagctatctt ctttttactc ctttctcacc atctaagatg tcttatttaa atagctccaa    6780
ggaagtgacc taaccttga tgagcaaaat attactcagt ttttattttc cattcaacaa     6840
aagcagtggg aaagcttgcc atctggattc taagaaattg tgcaatataa aaaatgttat    6900
atcctcgaga aatatcttgc tgagtcaccc taggaaataa ctacctttta tttatctggt    6960
agcctaatgt ttccacacat ttatcctgaa tattgcaagt gagggactga atcattttta    7020
attgggagtt atcttttctca ggcatgttct cttggagtct ttttgaagtg cctgacacgt   7080
gtaacaggat gacatatata tcattcctac aatatgaaca actgttacat aaaaaattat    7140
caaggagatg atttcaggaa acaagtgaac tttctgcaaa gacttataaa aattttaggt    7200
caaattaact tcaggcttta aatgcactaa tctacctaag agaaaaaaaa agaaaaaaaa    7260
caggaaggag ttttaagggc tcatgtgcct gttgtatcaa cccccaagtg tcttcttggt    7320
actgcttcct catcatctaa gataaactga caactttaaa gtgaggtaga aggtgtattg    7380
aattgggagt caggagaatt gggttctaac cccaagttca gccacaaata aagctgtgag    7440
acattggcaa gtcatttaac tttcctgagt cttggttttc tcatcctgaa agtgagggat    7500
tcggctgacg tctctaaaat ctctttcaac tctaaccttt attctgaata agaatttaat    7560
attcacttag tgctgtgccc agcactgttt gtaaacagca gctgtttgtt atctctagtt    7620
```

-continued

```
tggtctctgt attctcatca cttctcagaa ctatcattct accgtcttca tttctaaacc    7680
caaaactgct agaatacagg gactctggac tgggtctgta aattttttct gatcaaaact    7740
ttatagcagt gtagagaagg gacacattca aattacacta aggacattga catagctggg    7800
gttgtttcct tgtttatatt ataaaaccta aatgtggaac tatattctaa taatctttca    7860
taggaaggaa aatagccaga ctgggtatta tgcatgtaac aaatgaggac attgtgcata    7920 agaaggaaa cattagtttt ctgtcatcct gggccaagta cctcattaca gtaaatgtgt     7980
gtctttggaa actctttgct tgtgctgatg gcggtaagca tggggtccca ggcaggttca    8040
aaggctgaac tgtaagaaat gggcaagaca atacattttg ttttggaagg aatttctcat    8100
gggataagtt tcccaaagct tgaattatag gctatgaaat aaagcaaata gatggagaga    8160
aaacaagtat tgttttcaaa aagtacaagt caattctatt taaagaagac aagctgaaaa    8220
taaaacaaaa ataaacacaa tttaggaggt tacagagttg aagacagtat gaattgttgt    8280
gaaggccaaa atcaaatgtg aaagttaggt tctctgagaa aagggtaagc agaaaggatg    8340
atttctcaag caattaataa ggaattattt tcttgtgcca tgttctagat gcattgagca    8400
cagatcctct tgtcctaagc tgtcctagag gctcaggtta gcatctatcc aaagttgtcc    8460
tttgatttta ttgtctgaaa gaacagaagg catcagagtt tccagtcact gaagagtagg    8520
gtttgttcat cacttcccag caatcacatc actttgtgta ggtaaggata tatgatgtgc    8580
ttagattact tatgaagctc tctctaagtg ggagaatgac ctgtccatgg gacaactccc    8640
cgttttcatg gtcatttcag aagtacctct ttttgggcag tgctcctgga tctacttcta    8700
cagccacatt ctactctgca caatcctccc tatgtaaagc caggcacagt acaaatatgc    8760
ttcttgcaag tgaagaaaac ccatggaagt cctagcttca tggcacgctg cagcaatccc    8820
aagctaccag gagcctcttt tgaacccact tccctaagtc tttgctcttc accagagaat    8880
ggaaattgtt catcctggtg aactgtggcc aagttctgct ccctaagtat ttacttggag    8940
tagggaggtt aaagggaaga aattcagggg gagagaagca aaagagaaca cttccaactc    9000
cctcccccat ctcccaatgc tccccacctt ccttatcact gctctactga agggtgtata    9060
aatcctgctc ttggttagaa ttctccttat taacagtgtt atatacatat aaatatatat    9120
ataaatatat tcctttttc agccctgtag acatgaactg atcttccctt gaagatacaa     9180
acacatggcc atttttgtt tgggatttt tgttttcaa ggttttcat ttttgttat        9240 taggtggatt ttttcccctg ggtactagct ctgtgaagga gataaaaagc gcaatgtgtg    9300
ttaaaaaaaa aaattaaaa ttaaaatgaa aaaaagcttt ttttcttttc tttttaaatg     9360
tatttaaatt ctgtttctct cttctgttac tttacacgta tgaatgctct gctcttctgt    9420
gatcttaaaa caaatgaaa taaacgtgaa aaggagatgt gtcttcattg acctgtca     9478
```

<210> SEQ ID NO 11
<211> LENGTH: 741
<212> TYPE: PRT
<213> ORGANISM: Homo sapiens

<400> SEQUENCE: 11

```
Met Leu Glu Arg Lys Lys Pro Lys Thr Ala Glu Asn Gln Lys Ala Ser
1               5                   10                  15

Glu Glu Asn Glu Ile Thr Gln Pro Gly Gly Ser Ser Ala Lys Pro Gly
            20                  25                  30

Leu Pro Cys Leu Asn Phe Glu Ala Val Leu Ser Pro Asp Pro Ala Leu
        35                  40                  45
```

```
Ile His Ser Thr His Ser Leu Thr Asn Ser His Ala His Thr Gly Ser
     50                  55                  60

Ser Asp Cys Asp Ile Ser Cys Lys Gly Met Thr Glu Arg Ile His Ser
65                  70                  75                  80

Ile Asn Leu His Asn Phe Ser Asn Ser Val Leu Glu Thr Leu Asn Glu
                85                  90                  95

Gln Arg Asn Arg Gly His Phe Cys Asp Val Thr Val Arg Ile His Gly
            100                 105                 110

Ser Met Leu Arg Ala His Arg Cys Val Leu Ala Ala Gly Ser Pro Phe
        115                 120                 125

Phe Gln Asp Lys Leu Leu Leu Gly Tyr Ser Asp Ile Glu Ile Pro Ser
    130                 135                 140

Val Val Ser Val Gln Ser Val Gln Lys Leu Ile Asp Phe Met Tyr Ser
145                 150                 155                 160

Gly Val Leu Arg Val Ser Gln Ser Glu Ala Leu Gln Ile Leu Thr Ala
                165                 170                 175

Ala Ser Ile Leu Gln Ile Lys Thr Val Ile Asp Glu Cys Thr Arg Ile
            180                 185                 190

Val Ser Gln Asn Val Gly Asp Val Phe Pro Gly Ile Gln Asp Ser Gly
        195                 200                 205

Gln Asp Thr Pro Arg Gly Thr Pro Glu Ser Gly Thr Ser Gly Gln Ser
    210                 215                 220

Ser Asp Thr Glu Ser Gly Tyr Leu Gln Ser His Pro Gln His Ser Val
225                 230                 235                 240

Asp Arg Ile Tyr Ser Ala Leu Tyr Ala Cys Ser Met Gln Asn Gly Ser
                245                 250                 255

Gly Glu Arg Ser Phe Tyr Ser Gly Ala Val Val Ser His His Glu Thr
            260                 265                 270

Ala Leu Gly Leu Pro Arg Asp His His Met Glu Asp Pro Ser Trp Ile
        275                 280                 285

Thr Arg Ile His Glu Arg Ser Gln Gln Met Glu Arg Tyr Leu Ser Thr
    290                 295                 300

Thr Pro Glu Thr Thr His Cys Arg Lys Gln Pro Arg Pro Val Arg Ile
305                 310                 315                 320

Gln Thr Leu Val Gly Asn Ile His Ile Lys Gln Glu Met Glu Asp Asp
                325                 330                 335

Tyr Asp Tyr Tyr Gly Gln Gln Arg Val Gln Ile Leu Glu Arg Asn Glu
            340                 345                 350

Ser Glu Glu Cys Thr Glu Asp Thr Asp Gln Ala Glu Gly Thr Glu Ser
        355                 360                 365

Glu Pro Lys Gly Glu Ser Phe Asp Ser Gly Val Ser Ser Ser Ile Gly
    370                 375                 380

Thr Glu Pro Asp Ser Val Glu Gln Gln Phe Gly Pro Gly Ala Ala Arg
385                 390                 395                 400

Asp Ser Gln Ala Glu Pro Thr Gln Pro Glu Gln Ala Ala Glu Ala Pro
                405                 410                 415

Ala Glu Gly Gly Pro Gln Thr Asn Gln Leu Glu Thr Gly Ala Ser Ser
            420                 425                 430

Pro Glu Arg Ser Asn Glu Val Glu Met Asp Ser Thr Val Ile Thr Val
        435                 440                 445

Ser Asn Ser Ser Asp Lys Ser Val Leu Gln Gln Pro Ser Val Asn Thr
    450                 455                 460
```

```
Ser Ile Gly Gln Pro Leu Pro Ser Thr Gln Leu Tyr Leu Arg Gln Thr
465                 470                 475                 480

Glu Thr Leu Thr Ser Asn Leu Arg Met Pro Leu Thr Leu Thr Ser Asn
                485                 490                 495

Thr Gln Val Ile Gly Thr Ala Gly Asn Thr Tyr Leu Pro Ala Leu Phe
            500                 505                 510

Thr Thr Gln Pro Ala Gly Ser Gly Pro Lys Pro Phe Leu Phe Ser Leu
        515                 520                 525

Pro Gln Pro Leu Ala Gly Gln Gln Thr Gln Phe Val Thr Val Ser Gln
545                 550                 555                 560

Pro Gly Leu Ser Thr Phe Thr Ala Gln Leu Pro Ala Pro Gln Pro Leu
545                 550                 555                 560

Ala Ser Ser Ala Gly His Ser Thr Ala Ser Gly Gln Gly Glu Lys Lys
                565                 570                 575

Pro Tyr Glu Cys Thr Leu Cys Asn Lys Thr Phe Thr Ala Lys Gln Asn
            580                 585                 590

Tyr Val Lys His Met Phe Val His Thr Gly Glu Lys Pro His Gln Cys
        595                 600                 605

Ser Ile Cys Trp Arg Ser Phe Ser Leu Lys Asp Tyr Leu Ile Lys His
610                 615                 620

Met Val Thr His Thr Gly Val Arg Ala Tyr Gln Cys Ser Ile Cys Asn
625                 630                 635                 640

Lys Arg Phe Thr Gln Lys Ser Ser Leu Asn Val His Met Arg Leu His
                645                 650                 655

Arg Gly Glu Lys Ser Tyr Glu Cys Tyr Ile Cys Lys Lys Lys Phe Ser
            660                 665                 670

His Lys Thr Leu Leu Glu Arg His Val Ala Leu His Ser Ala Ser Asn
        675                 680                 685

Gly Thr Pro Pro Ala Gly Thr Pro Pro Gly Ala Arg Ala Gly Pro Pro
690                 695                 700

Gly Val Val Ala Cys Thr Glu Gly Thr Thr Tyr Val Cys Ser Val Cys
705                 710                 715                 720

Pro Ala Lys Phe Asp Gln Ile Glu Gln Phe Asn Asp His Met Arg Met
                725                 730                 735

His Val Ser Asp Gly
            740

<210> SEQ ID NO 12
<211> LENGTH: 3317
<212> TYPE: DNA
<213> ORGANISM: Homo sapiens

<400> SEQUENCE: 12
gttgggaaac agcccagtgg tataaggatg aggaaactga agcccagaga ggtgaagtga      60
ggtgcccaag gccacacagc aagttagagg cacagctagt acggtagctc aagtctcctg     120
actcccagtc cagtgctcct cccattactc cacgagtcct gtctctaagc ttcctgacaa     180
atgctagaac ggaagaaacc caagacagct gaaaaccaga aggcatctga ggagaatgag     240
attactcagc cgggtggatc cagcgccaag ccgggccttc cctgcctgaa ctttgaagct     300
gttttgtctc cagacccagc cctcatccac tcaacacatt cactgacaaa ctctcacgct     360
cacaccgggt catctgattg tgacatcagt tgcaagggga tgaccgagcg cattcacagc     420 atcaacttc acaacttcag caattccgtg ctcgagaccc tcaacgagca gcgcaaccgt     480
ggccacttct gtgacgtaac ggtgcgcatc cacgggagca tgctgcgcgc acaccgctgc     540
```

```
gtgctggcag ccggcagccc cttcttccag acaaactgc tgcttggcta cagcgacatc    600
gagatcccgt cggtggtgtc agtgcagtca gtgcaaaagc tcattgactt catgtacagc    660
ggcgtgctac gggtctcgca gtcggaagct ctgcagatcc tcacggccgc cagcatcctg    720
cagatcaaaa cagtcatcga cgagtgcacg cgcatcgtgt cacagaacgt gggcgatgtg    780
ttcccgggga tccaggactc gggccaggac acgccgcggg gcactcccga gtcaggcacg    840
tcaggccaga gcagcgacac ggagtcgggc tacctgcaga gccacccaca gcacagcgtg    900
gacaggatct actcggcact ctacgcgtgc tccatgcaga atggcagcgg cgagcgctct    960
ttttacagcg gcgcagtggt cagccaccac gagactgcgc tcggcctgcc ccgcgaccac   1020
cacatggaag accccagctg gatcacacgc atccatgagc gctcgcagca gatggagcgc   1080
tacctgtcca ccaccccga gaccacgcac tgccgcaagc agccccggcc tgtgcgcatc   1140
cagaccctag tgggcaacat ccacatcaag caggagatgg aggacgatta cgactactac   1200
gggcagcaaa gggtgcagat cctggaacgc aacgaatccg aggagtgcac ggaagacaca   1260
gaccaggccg agggcaccga gagtgagccc aaaggtgaaa gcttcgactc gggcgtcagc   1320
tcctccatag gcaccgagcc tgactcggtg gagcagcagt ttgggcctgg ggcggcgcgg   1380
gacagccagg ctgaacccac ccaacccgag caggctgcag aagccccgc tgagggtggt   1440 ccgcagacaa accagctaga aacaggtgct tcctctccgg agagaagcaa tgaagtggag   1500
atggacagca ctgttatcac tgtcagcaac agctccgaca gagcgtcct acaacagcct   1560 tcggtcaaca cgtccatcgg gcagccattg ccaagtaccc agctctactt acgccagaca   1620
gaaaccctca ccagcaacct gaggatgcct ctgaccttga ccagcaacac gcaggtcatt   1680
ggcacagctg gcaacaccta cctgccagcc ctcttcacta cccagcccgc gggcagtggc   1740
cccaagcctt tcctcttcag cctgccacag cccctggcag gccagcagac ccagtttgtg   1800
acagtgtccc agcccggtct gtcgaccttt actgcacagc tgccagcgcc acagcccctg   1860
gcctcatccg caggccacag cacagccagt gggcaaggcg aaaaaaagcc ttatgagtgc   1920
actctctgca acaagacttt caccgccaaa cagaactacg tcaagcacat gttcgtacac   1980
acaggtgaga agccccacca atgcagcatc tgttggcgct ccttctcctt aaaggattac   2040
cttatcaagc acatggtgac acacacagga gtgagggcat accagtgtag tatctgcaac   2100
aagcgcttca cccagaagag ctccctcaac gtgcacatgc gcctccaccg gggagagaag   2160
tcctacgagt gctacatctg caaaaagaag ttctctcaca gaccctcct ggagcgacac   2220 gtggccctgc acagtgccag caatgggacc ccccctgcag gcacacccc aggtgcccgc   2280 gctggccccc caggcgtggt ggcctgcacg gaggggacca cttacgtctg ctccgtctgc   2340
ccagcaaagt ttgaccaaat cgagcagttc aacgaccaca tgaggatgca tgtgtctgac   2400
ggataagtag tatctttctc tctttcttat gaacaaaaca aacaacaac aaaaacaaa     2460 caaacaaaaa agctatggca ctagaattta agaaatgttt tggtttcatt tttactttct   2520
gtttttgttt ttgtttcgtt tcattttgta ctacatgaag aactgttttt tgcctgctgg   2580
tacattacat ttccggaggc ttgggtgaat aatagttttc ccagtctccc tcggatggtg   2640
gccttaaggc ctggtagtgc ttcaagaggt ccactggttg gatctctagc tactggcctc   2700
taaatacaac ccttctttac aaaaaaatct tttaaaaaaa agtaaaaaaa aaaaaaaat    2760 ttccacttgt gaagagcact acaaaaaata taacaaaaa tctaaaaggc ctactgtctt    2820
taagtacacc gcttgcagtg tttcagtgga cattttcaca attctggccg cttggacttc   2880
```

```
acagtaacca gttaaaactg tggaatatca cttctggttg aaaacccaga ggaaaggccc   2940
tgctgttttc cacctaccac gttgtctgat tcataaaag gctgtgggg gtgggaaggg    3000 cagtgggttc ggtggtgtgg gaaagaaaga cgaatggcag gcttcttccc cagattctgc  3060
ccgggtccac acaccctggc ccaccttctc catatccccc tcttgcagca gaagccagga  3120
agacttggac aagcaacaag caacagtggc tatcgtattt attcagtgtc ttcgctgagc  3180
cacagcctca gcacaatcaa gagggacttt catgaaaggc aggaatgcag ataaaacaaa  3240
gatatcagaa atttgcacct atgtttctag gtacaagaga aggattattt ccaacaatct  3300
ttgcaaaaaa aaaaaaa                                                 3317
```

<210> SEQ ID NO 13
<211> LENGTH: 668
<212> TYPE: PRT
<213> ORGANISM: Homo sapiens

<400> SEQUENCE: 13

```
Met Thr Glu Arg Ile His Ser Ile Asn Leu His Asn Phe Ser Asn Ser
1               5                   10                  15

Val Leu Glu Thr Leu Asn Glu Gln Arg Asn Arg Gly His Phe Cys Asp
            20                  25                  30

Val Thr Val Arg Ile His Gly Ser Met Leu Arg Ala His Arg Cys Val
        35                  40                  45

Leu Ala Ala Gly Ser Pro Phe Phe Gln Asp Lys Leu Leu Leu Gly Tyr
    50                  55                  60

Ser Asp Ile Glu Ile Pro Ser Val Val Ser Val Gln Ser Val Gln Lys
65                  70                  75                  80

Leu Ile Asp Phe Met Tyr Ser Gly Val Leu Arg Val Ser Gln Ser Glu
                85                  90                  95

Ala Leu Gln Ile Leu Thr Ala Ala Ser Ile Leu Gln Ile Lys Thr Val
            100                 105                 110

Ile Asp Glu Cys Thr Arg Ile Val Ser Gln Asn Val Gly Asp Val Phe
        115                 120                 125

Pro Gly Ile Gln Asp Ser Gly Gln Asp Thr Pro Arg Gly Thr Pro Glu
    130                 135                 140

Ser Gly Thr Ser Gly Gln Ser Ser Asp Thr Glu Ser Gly Tyr Leu Gln
145                 150                 155                 160

Ser His Pro Gln His Ser Val Asp Arg Ile Tyr Ser Ala Leu Tyr Ala
                165                 170                 175

Cys Ser Met Gln Asn Gly Ser Gly Glu Arg Ser Phe Tyr Ser Gly Ala
            180                 185                 190

Val Val Ser His His Glu Thr Ala Leu Gly Leu Pro Arg Asp His His
        195                 200                 205

Met Glu Asp Pro Ser Trp Ile Thr Arg Ile His Glu Arg Ser Gln Gln
    210                 215                 220

Met Glu Arg Tyr Leu Ser Thr Thr Pro Glu Thr Thr His Cys Arg Lys
225                 230                 235                 240

Gln Pro Arg Pro Val Arg Ile Gln Thr Leu Val Gly Asn Ile His Ile
                245                 250                 255

Lys Gln Glu Met Glu Asp Asp Tyr Asp Tyr Tyr Gly Gln Arg Val
            260                 265                 270

Gln Ile Leu Glu Arg Asn Glu Ser Glu Glu Cys Thr Glu Asp Thr Asp
        275                 280                 285

Gln Ala Glu Gly Thr Glu Ser Glu Pro Lys Gly Glu Ser Phe Asp Ser
```

```
            290                 295                 300
Gly Val Ser Ser Ile Gly Thr Glu Pro Asp Ser Val Glu Gln Gln
305                 310                 315                 320

Phe Gly Pro Gly Ala Arg Asp Ser Gln Ala Glu Pro Thr Gln Pro
                325                 330                 335

Glu Gln Ala Ala Glu Ala Pro Ala Glu Gly Gly Pro Gln Thr Asn Gln
                340                 345                 350

Leu Glu Thr Gly Ala Ser Ser Pro Glu Arg Ser Asn Glu Val Glu Met
                355                 360                 365

Asp Ser Thr Val Ile Thr Val Ser Asn Ser Ser Asp Lys Ser Val Leu
370                 375                 380

Gln Gln Pro Ser Val Asn Thr Ser Ile Gly Gln Pro Leu Pro Ser Thr
385                 390                 395                 400

Gln Leu Tyr Leu Arg Gln Thr Glu Thr Leu Thr Ser Asn Leu Arg Met
                405                 410                 415

Pro Leu Thr Leu Thr Ser Asn Thr Gln Val Ile Gly Thr Ala Gly Asn
                420                 425                 430

Thr Tyr Leu Pro Ala Leu Phe Thr Thr Gln Pro Ala Gly Ser Gly Pro
                435                 440                 445

Lys Pro Phe Leu Phe Ser Leu Pro Gln Pro Leu Ala Gly Gln Gln Thr
                450                 455                 460

Gln Phe Val Thr Val Ser Gln Pro Gly Leu Ser Thr Phe Thr Ala Gln
465                 470                 475                 480

Leu Pro Ala Pro Gln Pro Leu Ala Ser Ser Ala Gly His Ser Thr Ala
                485                 490                 495

Ser Gly Gln Gly Glu Lys Lys Pro Tyr Glu Cys Thr Leu Cys Asn Lys
                500                 505                 510

Thr Phe Thr Ala Lys Gln Asn Tyr Val Lys His Met Phe Val His Thr
                515                 520                 525

Gly Glu Lys Pro His Gln Cys Ser Ile Cys Trp Arg Ser Phe Ser Leu
                530                 535                 540

Lys Asp Tyr Leu Ile Lys His Met Val Thr His Thr Gly Val Arg Ala
545                 550                 555                 560

Tyr Gln Cys Ser Ile Cys Asn Lys Arg Phe Thr Gln Lys Ser Ser Leu
                565                 570                 575

Asn Val His Met Arg Leu His Arg Gly Glu Lys Ser Tyr Glu Cys Tyr
                580                 585                 590

Ile Cys Lys Lys Lys Phe Ser His Lys Thr Leu Leu Glu Arg His Val
                595                 600                 605

Ala Leu His Ser Ala Ser Asn Gly Thr Pro Ala Gly Thr Pro Pro
610                 615                 620

Gly Ala Arg Ala Gly Pro Pro Gly Val Val Ala Cys Thr Glu Gly Thr
625                 630                 635                 640

Thr Tyr Val Cys Ser Val Cys Pro Ala Lys Phe Asp Gln Ile Glu Gln
                645                 650                 655

Phe Asn Asp His Met Arg Met His Val Ser Asp Gly
                660                 665

<210> SEQ ID NO 14
<211> LENGTH: 3541
<212> TYPE: DNA
<213> ORGANISM: Homo sapiens

<400> SEQUENCE: 14
```

```
gaagaagtag gggcgggggg aagtttagga gttgaggaaa gaagattaaa gagcgcgagg      60
agacaaataa aaagaagtgt taagaattgc ctttgggact ctgaaggctg aagaattgat     120
gaattgcaag tttgtgcccc atagctgcac agactgcctg aagttacatt tagagactga     180
aatcactgca ccttaaaaac aaaagattga gctgcactgt attcctaatg tttcatcatt     240
actaacagga tattcctcat gacattgctg tctgatcttt gaccatcagt ctgtgacctg     300
ccccttctct ttacatgcag ccgctctctg ctccctgccc caatgaacat ctgcactagg     360
cccaagcctt ggagtaattt acctgaagag tgacaccatt gattttgaaa ctactgaaga     420
aacccaagac agctgaaaac cagaaggcat ctgaggagaa tgagattact cagccgggtg     480
gatccagcgc caagccgggc cttccctgcc tgaactttga agctgttttg tctccagacc     540
cagccctcat ccactcaaca cattcactga caaactctca cgctcacacc gggtcatctg     600
attgtgacat cagttgcaag gggatgaccg agcgcattca cagcatcaac cttcacaact     660
tcagcaattc cgtgctcgag accctcaacg agcagcgcaa ccgtggccac ttctgtgacg     720
taacggtgcg catccacggg agcatgctgc gcgcacaccg ctgcgtgctg gcagccggca     780
gccccttctt ccaggacaaa ctgctgcttg gctacagcga catcgagatc ccgtcggtgg     840
tgtcagtgca gtcagtgcaa aagctcattg acttcatgta cagcggcgtg ctacgggtct     900
cgcagtcgga agctctgcag atcctcacgg ccgccagcat cctgcagatc aaaacagtca     960
tcgacgagtg cacgcgcatc gtgtcacaga acgtgggcga tgtgttcccg gggatccagg    1020
actcgggcca ggacacgccg cggggcactc ccgagtcagg cacgtcaggc cagagcagcg    1080
acacggagtc gggctacctg cagagccacc cacagcacag cgtggacagg atctactcgg    1140
cactctacgc gtgctccatg cagaatggca gcggcgagcg ctcttttac agcggcgcag    1200
tggtcagcca ccacgagact gcgctcggcc tgccccgcga ccaccacatg gaagacccca    1260
gctggatcac acgcatccat gagcgctcgc agcagatgga gcgctacctg tccaccaccc    1320
ccgagaccac gcactgccgc aagcagcccc ggcctgtgcg catccagacc ctagtgggca    1380
acatccacat caagcaggag atggaggacg attacgacta ctacgggcag caagggtgc    1440
agatcctgga acgcaacgaa tccgaggagt gcacggaaga cacagaccag gccgagggca    1500
ccgagagtga gcccaaaggt gaaagcttcg actcgggcgt cagctcctcc ataggcaccg    1560
agcctgactc ggtggagcag cagtttgggc ctggggcggc gcgggacagc caggctgaac    1620
ccacccaacc cgagcaggct gcagaagccc ccgctgaggg tggtccgcag acaaaccagc    1680
tagaaacagg tgcttcctct ccggagagaa gcaatgaagt ggagatggac agcactgtta    1740
tcactgtcag caacagctcc gacaagagcg tcctacaaca gccttcggtc aacacgtcca    1800
tcgggcagcc attgccaagt acccagctct acttacgcca gacagaaacc ctcaccagca    1860
acctgaggat gcctctgacc ttgaccagca acacgcaggt cattggcaca gctggcaaca    1920
cctacctgcc agccctcttc actacccagc ccgcgggcag tggcccccaag cctttcctct    1980
tcagcctgcc acagccctg gcaggccagc agacccagtt tgtgacagtg tcccagccg    2040
gtctgtcgac ctttactgca cagctgccag cgccacagcc cctggcctca tccgcaggcc    2100
acagcacagc cagtgggcaa ggcgaaaaaa agccttatga gtgcactctc tgcaacaaga    2160
cttttcaccgc caaacagaac tacgtcaagc acatgttcgt acacacaggt gagaagcccc    2220
accaatgcag catctgttgg cgctccttct ccttaaagga ttaccttatc aagcacatgg    2280
tgacacacac aggagtgagg gcataccagt gtagtatctg caacaagcgc ttcacccaga    2340
agagctccct caacgtgcac atgcgcctcc accggggaga gaagtcctac gagtgctaca    2400
```

-continued

```
tctgcaaaaa gaagttctct cacaagaccc tcctggagcg acacgtggcc ctgcacagtg    2460
ccagcaatgg gaccccccct gcaggcacac ccccaggtgc ccgcgctggc cccccaggcg    2520
tggtggcctg cacggagggg accacttacg tctgctccgt ctgcccagca agtttgacc     2580 aaatcgagca gttcaacgac cacatgagga tgcatgtgtc tgacggataa gtagtatctt    2640
tctctctttc ttatgaacaa aacaaaacaa caacaaaaaa caaacaaaca aaaaagctat    2700
ggcactagaa tttaagaaat gttttggttt cattttact ttctgttttt gttttgttt      2760 cgtttcattt tgtactacat gaagaactgt tttttgcctg ctggtacatt acatttccgg    2820
aggcttgggt gaataatagt tttcccagtc tccctcggat ggtggcctta aggcctggta    2880
gtgcttcaag aggtccactg gttggatctc tagctactgg cctctaaata caaccttct     2940 ttacaaaaaa atcttttaaa aaaagtaaa aaaaaaaaa aaatttccac ttgtgaagag      3000
cactacaaaa aatatataac aaaatctaaa aggcctactg tctttaagta caccgcttgc    3060
agtgtttcag tggacatttt cacaattctg gccgcttgga cttcacagta accagttaaa    3120
actgtggaat atcacttctg gttgaaaacc cagaggaaag gccctgctgt tttccaccta    3180
ccacgttgtc tgatttcata aagggctgt ggggtggga agggcagtgg gttcggtggt      3240
gtgggaaaga aagacgaatg gcaggcttct tccccagatt ctgcccgggt ccacacaccc    3300
tggcccacct tctccatatc cccctcttgc agcagaagcc aggaagactt ggacaagcaa    3360
caagcaacag tggctatcgt atttattcag tgtcttcgct gagccacagc ctcagcacaa    3420
tcaagaggga ctttcatgaa aggcaggaat gcagataaaa caaagatatc agaaatttgc    3480
acctatgttt ctaggtacaa gagaaggatt atttccaaca atctttgcaa aaaaaaaaa     3540 a                                                                     3541
```

<210> SEQ ID NO 15
<211> LENGTH: 403
<212> TYPE: PRT
<213> ORGANISM: Homo sapiens

<400> SEQUENCE: 15

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160
```

-continued

```
Arg Asp Lys Lys Gly Val Thr Ile Pro Ser Gln Arg Arg Tyr Val Tyr
            165                 170                 175

Tyr Tyr Ser Tyr Leu Leu Lys Asn His Leu Asp Tyr Arg Pro Val Ala
        180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
        210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Glu Thr Ser Glu
                275                 280                 285

Lys Val Glu Asn Gly Ser Leu Cys Asp Gln Ile Asp Ser Ile Cys
        290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Ser Thr Ser Val Thr Pro Asp
                355                 360                 365

Val Ser Asp Asn Glu Pro Asp His Tyr Arg Tyr Ser Asp Thr Thr Asp
        370                 375                 380

Ser Asp Pro Glu Asn Glu Pro Phe Asp Glu Asp Gln His Thr Gln Ile
385                 390                 395                 400

Thr Lys Val

<210> SEQ ID NO 16
<211> LENGTH: 5572
<212> TYPE: DNA
<213> ORGANISM: Homo sapiens

<400> SEQUENCE: 16
cctcccctcg cccggcgcgg tcccgtccgc ctctcgctcg cctcccgcct ccctcggtc       60 ttccgaggcg cccgggctcc cggcgcggcg gcggaggggg cggcaggcc ggcgggcggt      120 gatgtggcgg gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga    300 gccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg     480
aggcgcggcg gcgcggcggg cacctcccgc tcctggagcg gggggagaa gcggcggcgg    540 cggcggccgc ggcggctgca gctccaggga ggggtctga gtcgcctgtc accatttcca     600
gggctgggaa cgccggagag ttggtctctc cccttctact gcctccaaca cggcggcggc     660
ggcggcggca catccaggga cccgggccgg ttttaaacct cccgtccgcc gccgccgcac     720
```

```
ccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt tccatcctgc    960
agaagaagcc ccgccaccag cagcttctgc catctctctc ctccttttc ttcagccaca    1020
ggctcccaga catgacagcc atcatcaaag agatcgttag cagaaacaaa aggagatatc    1080
aagaggatgg attcgactta gacttgacct atatttatcc aaacattatt gctatgggat    1140
ttcctgcaga aagacttgaa ggcgtataca ggaacaatat tgatgatgta gtaaggtttt    1200
tggattcaaa gcataaaaac cattacaaga tatacaatct ttgtgctgaa agacattatg    1260
acaccgccaa atttaattgc agagttcac aatatccttt tgaagaccat aacccaccac    1320
agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaattttaa aggcacaaga ggccctagat ttctatgggg    1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaaagt agaaaatgga agtctatgtg    1920
atcaagaaat cgatagcatt tgcagtatag agcgtgcaga taatgacaag gaatatctag    1980
tacttacttt aacaaaaaat gatcttgaca agcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga acctttgat gaagatcagc    2220
atacacaaat tacaaagtc tgaattttt tttatcaaga gggataaaac accatgaaaa    2280
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaaggt tgtgtagctg tgtcatgtat    2460
ataccttttt gtgtcaaaag gacatttaaa attcaattag gattaataaa gatggcactt    2520
tcccgtttta ttccagtttt ataaaaagtg gagacagact gatgtgtata cgtaggaatt    2580
ttttcctttt gtgttctgtc accaactgaa gtggctaaag gctttgtga tatactggtt    2640
cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga ataattttta tgctggactc tggaccatat accatctcca gctatttaca    2820
cacccttc tttagcatgc tacagttatt aatctggaca ttcgaggaat tggccgctgt    2880
cactgcttgt tgtttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
```

```
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatacctg ctgtggatgc ttcatgtgct gcctgcaagc ttcttttttc    3300
tcattaaata taaaatattt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac atttttaaa    3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggttttttt tttttttttt tttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt tttccagaaa tttggtgtct    3900
tcaaattata ccttcacctt gacatttgaa tatccagcca ttttgtttct taatggtata    3960
aaattccatt ttcaataact tattggtgct gaaattgttc actagctgtg gtctgaccta    4020
gttaatttac aaatacagat tgaataggac ctactagagc agcatttata gagtttgatg    4080
gcaaatagat taggcagaac ttcatctaaa atattcttag taaataatgt tgacacgttt    4140
tccataccct gtcagtttca ttcaacaatt tttaaatttt taacaaagct cttaggagattt    4200 acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat actttttaaaa gggtagttga ataaatagca    4980
tcaccattct ttgctgtggc acaggttata aacttaagtg gagtttaccg gcagcatcaa    5040
atgtttcagc tttaaaaaat aaaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
```

```
ccatttgtta ttgtgtttgt taacaaccct ttatctctta gtgttataaa ctccacttaa    5520
aactgattaa agtctcattc ttgtcaaaaa aaaaaaaaaa aaaaaaaaaa aa             5572
```

<210> SEQ ID NO 17
<211> LENGTH: 264
<212> TYPE: PRT
<213> ORGANISM: Homo sapiens

<400> SEQUENCE: 17

```
Met Ile Met Ser Ser Tyr Leu Met Asp Ser Asn Tyr Ile Asp Pro Lys
1               5                   10                  15

Phe Pro Pro Cys Glu Glu Tyr Ser Gln Asn Ser Tyr Ile Pro Glu His
            20                  25                  30

Ser Pro Glu Tyr Tyr Gly Arg Thr Arg Glu Ser Gly Phe Gln His His
        35                  40                  45

His Gln Glu Leu Tyr Pro Pro Pro Pro Arg Pro Ser Tyr Pro Glu
    50                  55                  60

Arg Gln Tyr Ser Cys Thr Ser Leu Gln Gly Pro Gly Asn Ser Arg Gly
65                  70                  75                  80

His Gly Pro Ala Gln Ala Gly His His His Pro Glu Lys Ser Gln Ser
                85                  90                  95

Leu Cys Glu Pro Ala Pro Leu Ser Gly Ala Ser Ala Ser Pro Ser Pro
            100                 105                 110

Ala Pro Pro Ala Cys Ser Gln Pro Ala Pro Asp His Pro Ser Ser Ala
        115                 120                 125

Ala Ser Lys Gln Pro Ile Val Tyr Pro Trp Met Lys Lys Ile His Val
    130                 135                 140

Ser Thr Val Asn Pro Asn Tyr Asn Gly Gly Glu Pro Lys Arg Ser Arg
145                 150                 155                 160

Thr Ala Tyr Thr Arg Gln Gln Val Leu Glu Leu Glu Lys Glu Phe His
                165                 170                 175

Tyr Asn Arg Tyr Leu Thr Arg Arg Arg Ile Glu Ile Ala His Ser
            180                 185                 190

Leu Cys Leu Ser Glu Arg Gln Ile Lys Ile Trp Phe Gln Asn Arg Arg
        195                 200                 205

Met Lys Trp Lys Lys Asp His Arg Leu Pro Asn Thr Lys Val Arg Ser
    210                 215                 220

Ala Pro Pro Ala Gly Ala Pro Ser Thr Leu Ser Ala Ala Thr Pro
225                 230                 235                 240

Gly Thr Ser Glu Asp His Ser Gln Ser Ala Thr Pro Pro Glu Gln Gln
                245                 250                 255

Arg Ala Glu Asp Ile Thr Arg Leu
            260
```

<210> SEQ ID NO 18
<211> LENGTH: 2328
<212> TYPE: DNA
<213> ORGANISM: Homo sapiens

<400> SEQUENCE: 18

```
aacttttat tgtggtttgt ccgttccgag cgctccgcag aacagtcctc cctgtaagag      60
cctaaccatt gccagggaaa cctgccctgg gcgctccctt cattagcagt attttttta    120 aattaatctg attaataatt attttttcccc catttaattt ttttttcctcc caggtggagt   180 tgccgaagct gggggcagct ggggagggtg gggatgggag gggagagaca gaagttgagg    240
```

```
gcatctctct cttccttccc gaccctctgg cccccaaggg gcaggaggaa tgcaggagca      300
ggagttgagc ttgggagctg cagatgcctc cgcccctcct ctctcccagg ctcttcctcc      360
tgcccccttc ttgcaactct ccttaatttt gtttggcttt tggatgatta taattatttt      420
tatttttgaa tttatataaa gtatatgtgt gtgtgtgtgg agctgagaca ggctcggcag      480
cggcacagaa tgagggaaga cgagaaagag agtgggagag agagaggcag agagggagag      540
agggagagtg acagcagcgc tcgcggggc tcaaccccca gacctccaga aatgacgtca       600
gaatcatttg catcccgctg cctctacctg cctggtccag ctgggaccct gcctcgccgg      660
ccgcatggcc agagggttgg aaattaatga tcatgagctc gtatttgatg gactctaact      720
acatcgatcc gaaatttcct ccatgcgaag aatattcgca aaatagctac atccctgaac      780
acagtccgga atattacggc cggaccaggg aatcgggatt ccagcatcac caccaggagc      840
tgtacccacc accgcctccg cgccctagct accctgagcg ccagtatagc tgcaccagtc      900
tccaggggcc cggcaattcg cgaggccacg ggcggccca ggcggccac caccaccccg        960 agaaatcaca gtcgctctgc gagccggcgc ctctctcagg cgcctccgcc tccccgtccc     1020
cagccccgcc agcctgcagc cagccagccc ccgaccatcc ctccagcgcc gccagcaagc     1080
aacccatagt ctacccatgg atgaaaaaaa ttcacgttag cacggtgaac cccaattata     1140
acggagggga acccaagcgc tcgaggacag cctatacccg gcagcaagtc ctggaattag     1200
agaaagagtt tcattacaac cgctacctga cccgaaggag aaggatcgag atcgcccact     1260
cgctgtgcct ctctgagagg cagatcaaaa tctggttcca aaaccgtcgc atgaaatgga     1320
agaaggacca ccgactcccc aacaccaaag tcaggtcagc accccggcc ggcgctgcgc      1380 ccagcaccct ttcggcagct accccgggta cttctgaaga ccactcccag agcgccacgc     1440
cgccggagca gcaacgggca gaggacatta ccaggttata aaacataact cacacccctg     1500
cccccacccc atgcccccac cctcccctca cacacaaatt gactcttatt tatagaattt     1560
aatatatata tatatatata tatatatagg ttctttttctc tcttcctctc accttgtccc     1620
ttgtcagttc caaacagaca aaacagataa acaaacaagc ccctgccct cctctcccct      1680 ccactgttaa ggacccttttt aagcatgtga tgttgtctta gcatggtacc tgctgggtgt    1740
ttttttttaa aaggccattt tgggggggtta tttattttttt aagaaaaaaa gctgcaaaaa    1800
ttatatattg caaggtgtga tggtctggct tgggtgaatt tcaggggaaa tgaggaaaag     1860
aaaaaaggaa agaaattttta aagccaattc tcatccttct cctcctcctc cttcccccc     1920 tctttcctta ggcctttttgc attgaaaatg caccagggga ggttagtgag ggggaagtca    1980
ttttaaggag aacaaagcta tgaagttctt ttgtattatt gttgggggg ggtgtgggag      2040 gagaggggc gaagacagca gacaaagcta aatgcatctg gagagcctct cagagctgtt     2100
cagtttgagg agccaaaaga aaatcaaaat gaactttcag ttcagagagg cagtctatag     2160
gtagaatctc tccccacccc tatcgtggtt attgtgtttt tggactgaat ttacttgatt    2220
attgtaaaac ttgcaataaa gaattttagt gtcgatgtga aatgccccgt gatcaataat    2280
aaaccagtgg atgtgaatta gttttaaaaa aaaaaaaaaa aaaaaaaa                  2328
```

<210> SEQ ID NO 19  
<211> LENGTH: 264  
<212> TYPE: PRT  
<213> ORGANISM: Homo sapiens

<400> SEQUENCE: 19

Met Ile Met Ser Ser Tyr Leu Met Asp Ser Asn Tyr Ile Asp Pro Lys

```
             1               5                  10                 15
           Phe Pro Pro Cys Glu Glu Tyr Ser Gln Asn Ser Tyr Ile Pro Glu His
                         20                  25                  30

Ser Pro Glu Tyr Tyr Gly Arg Thr Arg Glu Ser Gly Phe Gln His His
                         35                  40                  45

His Gln Glu Leu Tyr Pro Pro Pro Pro Arg Pro Ser Tyr Pro Glu
                50                  55                  60

Arg Gln Tyr Ser Cys Thr Ser Leu Gln Gly Pro Gly Asn Ser Arg Gly
            65                  70                  75                  80

His Gly Pro Ala Gln Ala Gly His His Pro Glu Lys Ser Gln Ser
                             85                  90                  95

Leu Cys Glu Pro Ala Pro Leu Ser Gly Ala Ser Ala Ser Pro Ser Pro
                            100                 105                 110

Ala Pro Pro Ala Cys Ser Gln Pro Ala Pro Asp His Pro Ser Ser Ala
                            115                 120                 125

Ala Ser Lys Gln Pro Ile Val Tyr Pro Trp Met Lys Lys Ile His Val
                        130                 135                 140

Ser Thr Val Asn Pro Asn Tyr Asn Gly Gly Glu Pro Lys Arg Ser Arg
           145                 150                 155                 160

Thr Ala Tyr Thr Arg Gln Gln Val Leu Glu Leu Lys Glu Phe His
                             165                 170                 175

Tyr Asn Arg Tyr Leu Thr Arg Arg Arg Ile Glu Ile Ala His Ser
                        180                 185                 190

Leu Cys Leu Ser Glu Arg Gln Ile Lys Ile Trp Phe Gln Asn Arg Arg
                        195                 200                 205

Met Lys Trp Lys Lys Asp His Arg Leu Pro Asn Thr Lys Val Arg Ser
                210                 215                 220

Ala Pro Pro Ala Gly Ala Ala Pro Ser Thr Leu Ser Ala Ala Thr Pro
           225                 230                 235                 240

Gly Thr Ser Glu Asp His Ser Gln Ser Ala Thr Pro Pro Glu Gln Gln
                             245                 250                 255

Arg Ala Glu Asp Ile Thr Arg Leu
                        260

<210> SEQ ID NO 20
<211> LENGTH: 2459
<212> TYPE: DNA
<213> ORGANISM: Homo sapiens

<400> SEQUENCE: 20
acacacgtgt tacatggata cagctcctag ccagaagcaa gcaggctcta cccacacagg      60
cctccctctt agctagcggg ggctcaaccc ccagacctcc agaaatgacg tcagaatcat     120
ttgcatcccg ctgcctctac ctgcctggtc cagctgggac cctgcctcgc cggccgcatg     180
gccagagggt tgggtgagtg tgtatgggga agaggggctg gactctggta tccttggatg     240
gggggcactc caggctctcc agcctcctcg gctcagcctg gcccctccc catccaacat      300 ccactccagt cctcattcaa cttcctcttc ctgcgaaaga ggggcgctgc cccgtgacct     360
acacagactg agacacgatc gccatgaatg agagacctctg gaaaagctca ggagccgagg    420
cccacggggc ccagcagagg cctgagggga daccctgggc gggggctgaa tcactgcctc     480
ccgacagtcc cccaatgccc gggctttgga ggggagccgg gagcttccca tctccttttg     540
caggggaggg ttgtcagtct ggcgggatgt gcactggggg cactccaacc tctgctagct     600
aaccccacat caccacccac cccgcctcc cagcaccacc accaccacac acacaaaaaa      660
```

| | |
|---|---|
| attggataca ttttgaataa agcgattcgg ttccttatcc ggggactggg ttgctccgtg | 720 |
| tgattggccg gaggagtcac atggtgaaag taacttttaca gggtcgctag ctagtaggag | 780 |
| ggctttatgg agcagaaaaa cgacaaagcg agaaaaatta ttttccactc cagaaattaa | 840 |
| tgatcatgag ctcgtatttg atggactcta actacatcga tccgaaattt cctccatgcg | 900 |
| aagaatattc gcaaaatagc tacatccctg aacacagtcc ggaatattac ggccggacca | 960 |
| gggaatcggg attccagcat caccaccagg agctgtaccc accaccgcct ccgcgcccta | 1020 |
| gctaccctga gcgccagtat agctgcacca gtctccaggg gcccggcaat cgcgaggcc | 1080 |
| acgggccggc ccaggcgggc caccaccacc ccgagaaatc acagtcgctc tgcgagccgg | 1140 |
| cgcctctctc aggcgcctcc gcctcccgt cccagcccc gccagcctgc agccagccag | 1200 |
| cccccgacca tccctccagc gccgccagca agcaacccat agtctaccca tggatgaaaa | 1260 |
| aaattcacgt tagcacggtg aaccccaatt ataacggagg ggaacccaag cgctcgagga | 1320 |
| cagcctatac ccggcagcaa gtcctggaat tagagaaaga gtttcattac aaccgctacc | 1380 |
| tgacccgaag gagaaggatc gagatcgccc actcgctgtg cctctctgag aggcagatca | 1440 |
| aaatctggtt ccaaaaccgt cgcatgaaat ggaagaagga ccaccgactc ccaacacca | 1500 |
| aagtcaggtc agcaccccg gccggcgctg cgcccagcac cctttcggca gctaccccgg | 1560 |
| gtacttctga agaccactcc cagagcgcca cgccgccgga gcagcaacgg gcagaggaca | 1620 |
| ttaccaggtt ataaaacata actcacaccc ctgccccac ccatgcccc caccctcccc | 1680 |
| tcacacacaa attgactctt atttatagaa tttaatatat atatatatat atatatatat | 1740 |
| aggttctttt ctctcttcct ctcaccttgt cccttgtcag ttccaaacag acaaaacaga | 1800 |
| taaacaaaca agccccctgc cctcctctcc ctcccactgt taaggaccct tttaagcatg | 1860 |
| tgatgttgtc ttagcatggt acctgctggg tgtttttttt taaaaggcca ttttgggggg | 1920 |
| ttatttattt tttaagaaaa aaagctgcaa aaattatata ttgcaaggtg tgatggtctg | 1980 |
| gcttgggtga atttcagggg aaatgaggaa agaaaaaag gaaagaaatt ttaaagccaa | 2040 |
| ttctcatcct tctcctcctc ctccttcccc ccctctttcc ttaggccttt tgcattgaaa | 2100 |
| atgcaccagg ggaggttagt gagggggaag tcattttaag gagaacaaag ctatgaagtt | 2160 |
| cttttgtatt attgttgggg gggggtgtgg gaggagaggg ggcgaagaca gcagacaaag | 2220 |
| ctaaatgcat ctggagagcc tctcagagct gttcagtttg aggagccaaa agaaaatcaa | 2280 |
| aatgaacttt cagttcagag aggcagtcta taggtagaat ctctccccac ccctatcgtg | 2340 |
| gttattgtgt ttttggactg aatttacttg attattgtaa aacttgcaat aaagaatttt | 2400 |
| agtgtcgatg tgaaatgccc cgtgatcaat aataaaccag tggatgtgaa ttagttttta | 2459 |

<210> SEQ ID NO 21
<211> LENGTH: 2120
<212> TYPE: PRT
<213> ORGANISM: Homo sapiens

<400> SEQUENCE: 21

Met Arg Ser Phe Lys Arg Val Asn Phe Gly Thr Leu Leu Ser Ser Gln
1               5                   10                  15

Lys Glu Ala Glu Glu Leu Leu Pro Ala Leu Lys Glu Phe Leu Ser Asn
            20                  25                  30

Pro Pro Ala Gly Phe Pro Ser Ser Arg Ser Asp Ala Glu Arg Arg Gln
        35                  40                  45

Ala Cys Asp Ala Ile Leu Arg Ala Cys Asn Gln Gln Leu Thr Ala Lys

```
            50                  55                  60
Leu Ala Cys Pro Arg His Leu Gly Ser Leu Leu Glu Leu Ala Glu Leu
65                  70                  75                  80

Ala Cys Asp Gly Tyr Leu Val Ser Thr Pro Gln Arg Pro Leu Tyr
                85                  90                  95

Leu Glu Arg Ile Leu Phe Val Leu Leu Arg Asn Ala Ala Gln Gly
                100                 105                 110

Ser Pro Glu Ala Thr Leu Arg Leu Ala Gln Pro Leu His Ala Cys Leu
            115                 120                 125

Val Gln Cys Ser Arg Glu Ala Ala Pro Gln Asp Tyr Glu Ala Val Ala
            130                 135                 140

Arg Gly Ser Phe Ser Leu Leu Trp Lys Gly Glu Ala Leu Leu Glu
145                 150                 155                 160

Arg Arg Ala Ala Phe Ala Ala Arg Leu Lys Ala Leu Ser Phe Leu Val
                165                 170                 175

Leu Leu Glu Asp Glu Ser Thr Pro Cys Glu Val Pro His Phe Ala Ser
                180                 185                 190

Pro Thr Ala Cys Arg Ala Val Ala Ala His Gln Leu Phe Asp Ala Ser
                195                 200                 205

Gly His Gly Leu Asn Glu Ala Asp Ala Asp Phe Leu Asp Asp Leu Leu
            210                 215                 220

Ser Arg His Val Ile Arg Ala Leu Val Gly Glu Arg Gly Ser Ser Ser
225                 230                 235                 240

Gly Leu Leu Ser Pro Gln Arg Ala Leu Cys Leu Leu Glu Leu Thr Leu
                245                 250                 255

Glu His Cys Arg Arg Phe Cys Trp Ser Arg His His Asp Lys Ala Ile
                260                 265                 270

Ser Ala Val Glu Lys Ala His Ser Tyr Leu Arg Asn Thr Asn Leu Ala
            275                 280                 285

Pro Ser Leu Gln Leu Cys Gln Leu Gly Val Lys Leu Leu Gln Val Gly
            290                 295                 300

Glu Glu Gly Pro Gln Ala Val Ala Lys Leu Leu Ile Lys Ala Ser Ala
305                 310                 315                 320

Val Leu Ser Lys Ser Met Glu Ala Pro Ser Pro Leu Arg Ala Leu
                325                 330                 335

Tyr Glu Ser Cys Gln Phe Phe Leu Ser Gly Leu Glu Arg Gly Thr Lys
                340                 345                 350

Arg Arg Tyr Arg Leu Asp Ala Ile Leu Ser Leu Phe Ala Phe Leu Gly
            355                 360                 365

Gly Tyr Cys Ser Leu Leu Gln Gln Leu Arg Asp Asp Gly Val Tyr Gly
            370                 375                 380

Gly Ser Ser Lys Gln Gln Gln Ser Phe Leu Gln Met Tyr Phe Gln Gly
385                 390                 395                 400

Leu His Leu Tyr Thr Val Val Tyr Asp Phe Ala Gln Gly Cys Gln
                405                 410                 415

Ile Val Asp Leu Ala Asp Leu Thr Gln Leu Val Asp Ser Cys Lys Ser
                420                 425                 430

Thr Val Val Trp Met Leu Glu Ala Leu Glu Gly Leu Ser Gly Gln Glu
                435                 440                 445

Leu Thr Asp His Met Gly Met Thr Ala Ser Tyr Thr Ser Asn Leu Ala
            450                 455                 460

Tyr Ser Phe Tyr Ser His Lys Leu Tyr Ala Glu Ala Cys Ala Ile Ser
465                 470                 475                 480
```

```
Glu Pro Leu Cys Gln His Leu Gly Leu Val Lys Pro Gly Thr Tyr Pro
            485                 490                 495

Glu Val Pro Pro Glu Lys Leu His Arg Cys Phe Arg Leu Gln Val Glu
            500                 505                 510

Ser Leu Lys Lys Leu Gly Lys Gln Ala Gln Gly Cys Lys Met Val Ile
            515                 520                 525

Leu Trp Leu Ala Ala Leu Gln Pro Cys Ser Pro Glu His Met Ala Glu
            530                 535                 540

Pro Val Thr Phe Trp Val Arg Val Lys Met Asp Ala Ala Arg Ala Gly
545                 550                 555                 560

Asp Lys Glu Leu Gln Leu Lys Thr Leu Arg Asp Ser Leu Ser Gly Trp
                565                 570                 575

Asp Pro Glu Thr Leu Ala Leu Leu Arg Glu Glu Leu Gln Ala Tyr
                580                 585                 590

Lys Ala Val Arg Ala Asp Thr Gly Gln Glu Arg Phe Asn Ile Ile Cys
                595                 600                 605

Asp Leu Leu Glu Leu Ser Pro Glu Glu Thr Pro Ala Gly Ala Trp Ala
            610                 615                 620

Arg Ala Thr His Leu Val Glu Leu Ala Gln Val Leu Cys Tyr His Asp
625                 630                 635                 640

Phe Thr Gln Gln Thr Asn Cys Ser Ala Leu Asp Ala Ile Arg Glu Ala
                645                 650                 655

Leu Gln Leu Leu Asp Ser Val Arg Pro Glu Ala Gln Ala Arg Asp Gln
                660                 665                 670

Leu Leu Asp Asp Lys Ala Gln Ala Leu Leu Trp Leu Tyr Ile Cys Thr
            675                 680                 685

Leu Glu Ala Lys Met Gln Glu Gly Ile Glu Arg Asp Arg Arg Ala Gln
            690                 695                 700

Ala Pro Gly Asn Leu Glu Glu Phe Glu Val Asn Asp Leu Asn Tyr Glu
705                 710                 715                 720

Asp Lys Leu Gln Glu Asp Arg Phe Leu Tyr Ser Asn Ile Ala Phe Asn
                725                 730                 735

Leu Ala Ala Asp Ala Ala Gln Ser Lys Cys Leu Asp Gln Ala Leu Ala
            740                 745                 750

Leu Trp Lys Glu Leu Leu Thr Lys Gly Gln Ala Pro Ala Val Arg Cys
            755                 760                 765

Leu Gln Gln Thr Ala Ala Ser Leu Gln Ile Leu Ala Ala Leu Tyr Gln
            770                 775                 780

Leu Val Ala Lys Pro Met Gln Ala Leu Glu Val Leu Leu Leu Leu Arg
785                 790                 795                 800

Ile Val Ser Glu Arg Leu Lys Asp His Ser Lys Ala Ala Gly Ser Ser
                805                 810                 815

Cys His Ile Thr Gln Leu Leu Leu Thr Leu Gly Cys Pro Ser Tyr Ala
            820                 825                 830

Gln Leu His Leu Glu Glu Ala Ala Ser Ser Leu Lys His Leu Asp Gln
            835                 840                 845

Thr Thr Asp Thr Tyr Leu Leu Leu Ser Leu Thr Cys Asp Leu Leu Arg
850                 855                 860

Ser Gln Leu Tyr Trp Thr His Gln Lys Val Thr Lys Gly Val Ser Leu
865                 870                 875                 880

Leu Leu Ser Val Leu Arg Asp Pro Ala Leu Gln Lys Ser Lys Ala
                885                 890                 895
```

```
Trp Tyr Leu Leu Arg Val Gln Val Leu Gln Leu Val Ala Ala Tyr Leu
            900                 905                 910

Ser Leu Pro Ser Asn Asn Leu Ser His Ser Leu Trp Glu Gln Leu Cys
        915                 920                 925

Ala Gln Gly Trp Gln Thr Pro Glu Ile Ala Leu Ile Asp Ser His Lys
        930                 935                 940

Leu Leu Arg Ser Ile Ile Leu Leu Met Gly Ser Asp Ile Leu Ser
945                 950                 955                 960

Thr Gln Lys Ala Ala Val Glu Thr Ser Phe Leu Asp Tyr Gly Glu Asn
            965                 970                 975

Leu Val Gln Lys Trp Gln Val Leu Ser Glu Val Leu Ser Cys Ser Glu
        980                 985                 990

Lys Leu Val Cys His Leu Gly Arg Leu Gly Ser Val Ser Glu Ala Lys
        995                 1000                1005

Ala Phe Cys Leu Glu Ala Leu Lys Leu Thr Thr Lys Leu Gln Ile
    1010                1015                1020

Pro Arg Gln Cys Ala Leu Phe Leu Val Leu Lys Gly Glu Leu Glu
    1025                1030                1035

Leu Ala Arg Asn Asp Ile Asp Leu Cys Gln Ser Asp Leu Gln Gln
    1040                1045                1050

Val Leu Phe Leu Leu Glu Ser Cys Thr Glu Phe Gly Gly Val Thr
    1055                1060                1065

Gln His Leu Asp Ser Val Lys Lys Val His Leu Gln Lys Gly Lys
    1070                1075                1080

Gln Gln Ala Gln Val Pro Cys Pro Pro Gln Leu Pro Glu Glu Glu
    1085                1090                1095

Leu Phe Leu Arg Gly Pro Ala Leu Glu Leu Val Ala Thr Val Ala
    1100                1105                1110

Lys Glu Pro Gly Pro Ile Ala Pro Ser Thr Asn Ser Ser Pro Val
    1115                1120                1125

Leu Lys Thr Lys Pro Gln Pro Ile Pro Asn Phe Leu Ser His Ser
    1130                1135                1140

Pro Thr Cys Asp Cys Ser Leu Cys Ala Ser Pro Val Leu Thr Ala
    1145                1150                1155

Val Cys Leu Arg Trp Val Leu Val Thr Ala Gly Val Arg Leu Ala
    1160                1165                1170

Met Gly His Gln Ala Gln Gly Leu Asp Leu Leu Gln Val Val Leu
    1175                1180                1185

Lys Gly Cys Pro Glu Ala Ala Glu Arg Leu Thr Gln Ala Leu Gln
    1190                1195                1200

Ala Ser Leu Asn His Lys Thr Pro Pro Ser Leu Val Pro Ser Leu
    1205                1210                1215

Leu Asp Glu Ile Leu Ala Gln Ala Tyr Thr Leu Leu Ala Leu Glu
    1220                1225                1230

Gly Leu Asn Gln Pro Ser Asn Glu Ser Leu Gln Lys Val Leu Gln
    1235                1240                1245

Ser Gly Leu Lys Phe Val Ala Ala Arg Ile Pro His Leu Glu Pro
    1250                1255                1260

Trp Arg Ala Ser Leu Leu Leu Ile Trp Ala Leu Thr Lys Leu Gly
    1265                1270                1275

Gly Leu Ser Cys Cys Thr Thr Gln Leu Phe Ala Ser Ser Trp Gly
    1280                1285                1290

Trp Gln Pro Pro Leu Ile Lys Ser Val Pro Gly Ser Glu Pro Ser
```

-continued

```
            1295                1300                1305

Lys Thr Gln Gly Gln Lys Arg Ser Gly Arg Gly Arg Gln Lys Leu
        1310                1315                1320

Ala Ser Ala Pro Leu Arg Leu Asn Asn Thr Ser Gln Lys Gly Leu
        1325                1330                1335

Glu Gly Arg Gly Leu Pro Cys Thr Pro Lys Pro Pro Asp Arg Ile
        1340                1345                1350

Arg Gln Ala Gly Pro His Val Pro Phe Thr Val Phe Glu Glu Val
        1355                1360                1365

Cys Pro Thr Glu Ser Lys Pro Glu Val Pro Gln Ala Pro Arg Val
        1370                1375                1380

Gln Gln Arg Val Gln Thr Arg Leu Lys Val Asn Phe Ser Asp Asp
        1385                1390                1395

Ser Asp Leu Glu Asp Pro Val Ser Ala Glu Ala Trp Leu Ala Glu
        1400                1405                1410

Glu Pro Lys Arg Arg Gly Thr Ala Ser Arg Gly Arg Gly Arg Ala
        1415                1420                1425

Arg Lys Gly Leu Ser Leu Lys Thr Asp Ala Val Val Ala Pro Gly
        1430                1435                1440

Ser Ala Pro Gly Asn Pro Gly Leu Asn Gly Arg Ser Arg Arg Ala
        1445                1450                1455

Lys Lys Val Ala Ser Arg His Cys Glu Glu Arg Arg Pro Gln Arg
        1460                1465                1470

Ala Ser Asp Gln Ala Arg Pro Gly Pro Glu Ile Met Arg Thr Ile
        1475                1480                1485

Pro Glu Glu Glu Leu Thr Asp Asn Trp Arg Lys Met Ser Phe Glu
        1490                1495                1500

Ile Leu Arg Gly Ser Asp Gly Glu Asp Ser Ala Ser Gly Gly Lys
        1505                1510                1515

Thr Pro Ala Pro Gly Pro Glu Ala Ala Ser Gly Glu Trp Glu Leu
        1520                1525                1530

Leu Arg Leu Asp Ser Ser Lys Lys Lys Leu Pro Ser Pro Cys Pro
        1535                1540                1545

Asp Lys Glu Ser Asp Lys Asp Leu Gly Pro Arg Leu Arg Leu Pro
        1550                1555                1560

Ser Ala Pro Val Ala Thr Gly Leu Ser Thr Leu Asp Ser Ile Cys
        1565                1570                1575

Asp Ser Leu Ser Val Ala Phe Arg Gly Ile Ser His Cys Pro Pro
        1580                1585                1590

Ser Gly Leu Tyr Ala His Leu Cys Arg Phe Leu Ala Leu Cys Leu
        1595                1600                1605

Gly His Arg Asp Pro Tyr Ala Thr Ala Phe Leu Val Thr Glu Ser
        1610                1615                1620

Val Ser Ile Thr Cys Arg His Gln Leu Leu Thr His Leu His Arg
        1625                1630                1635

Gln Leu Ser Lys Ala Gln Lys His Arg Gly Ser Leu Glu Ile Ala
        1640                1645                1650

Asp Gln Leu Gln Gly Leu Ser Leu Gln Glu Met Pro Gly Asp Val
        1655                1660                1665

Pro Leu Ala Arg Ile Gln Arg Leu Phe Ser Phe Arg Ala Leu Glu
        1670                1675                1680

Ser Gly His Phe Pro Gln Pro Glu Lys Glu Ser Phe Gln Glu Arg
        1685                1690                1695
```

```
Leu Ala Leu Ile Pro Ser Gly Val Thr Val Cys Val Leu Ala Leu
        1700                1705                1710

Ala Thr Leu Gln Pro Gly Thr Val Gly Asn Thr Leu Leu Leu Thr
        1715                1720                1725

Arg Leu Glu Lys Asp Ser Pro Pro Val Ser Val Gln Ile Pro Thr
        1730                1735                1740

Gly Gln Asn Lys Leu His Leu Arg Ser Val Leu Asn Glu Phe Asp
        1745                1750                1755

Ala Ile Gln Lys Ala Gln Lys Glu Asn Ser Ser Cys Thr Asp Lys
        1760                1765                1770

Arg Glu Trp Trp Thr Gly Arg Leu Ala Leu Asp His Arg Met Glu
        1775                1780                1785

Val Leu Ile Ala Ser Leu Glu Lys Ser Val Leu Gly Cys Trp Lys
        1790                1795                1800

Gly Leu Leu Leu Pro Ser Ser Glu Glu Pro Gly Pro Ala Gln Glu
        1805                1810                1815

Ala Ser Arg Leu Gln Glu Leu Leu Gln Asp Cys Gly Trp Lys Tyr
        1820                1825                1830

Pro Asp Arg Thr Leu Leu Lys Ile Met Leu Ser Gly Ala Gly Ala
        1835                1840                1845

Leu Thr Pro Gln Asp Ile Gln Ala Leu Ala Tyr Gly Leu Cys Pro
        1850                1855                1860

Thr Gln Pro Glu Arg Ala Gln Glu Leu Leu Asn Glu Ala Val Gly
        1865                1870                1875

Arg Leu Gln Gly Leu Thr Val Pro Ser Asn Ser His Leu Val Leu
        1880                1885                1890

Val Leu Asp Lys Asp Leu Gln Lys Leu Pro Trp Glu Ser Met Pro
        1895                1900                1905

Ser Leu Gln Ala Leu Pro Val Thr Arg Leu Pro Ser Phe Arg Phe
        1910                1915                1920

Leu Leu Ser Tyr Ser Ile Ile Lys Glu Tyr Gly Ala Ser Pro Val
        1925                1930                1935

Leu Ser Gln Gly Val Asp Pro Arg Ser Thr Phe Tyr Val Leu Asn
        1940                1945                1950

Pro His Asn Asn Leu Ser Ser Thr Glu Glu Gln Phe Arg Ala Asn
        1955                1960                1965

Phe Ser Ser Glu Ala Gly Trp Arg Gly Val Val Gly Glu Val Pro
        1970                1975                1980

Arg Pro Glu Gln Val Gln Glu Ala Leu Thr Lys His Asp Leu Tyr
        1985                1990                1995

Ile Tyr Ala Gly His Gly Ala Gly Ala Arg Phe Leu Asp Gly Gln
        2000                2005                2010

Ala Val Leu Arg Leu Ser Cys Arg Ala Val Ala Leu Leu Phe Gly
        2015                2020                2025

Cys Ser Ser Ala Ala Leu Ala Val Arg Gly Asn Leu Glu Gly Ala
        2030                2035                2040

Gly Ile Val Leu Lys Tyr Ile Met Ala Gly Cys Pro Leu Phe Leu
        2045                2050                2055

Gly Asn Leu Trp Asp Val Thr Asp Arg Asp Ile Asp Arg Tyr Thr
        2060                2065                2070

Glu Ala Leu Leu Gln Gly Trp Leu Gly Ala Gly Pro Gly Ala Pro
        2075                2080                2085
```

| Leu | Leu | Tyr | Tyr | Val | Asn | Gln | Ala | Arg | Gln | Ala | Pro | Arg | Leu | Lys |
|-----|-----|-----|-----|-----|-----|-----|-----|-----|-----|-----|-----|-----|-----|-----|
| 2090 | | | | | 2095 | | | | | 2100 | | | | |

| Tyr | Leu | Ile | Gly | Ala | Ala | Pro | Ile | Ala | Tyr | Gly | Leu | Pro | Val | Ser |
|-----|-----|-----|-----|-----|-----|-----|-----|-----|-----|-----|-----|-----|-----|-----|
| 2105 | | | | | 2110 | | | | | 2115 | | | | |

Leu Arg
　2120

<210> SEQ ID NO 22
<211> LENGTH: 6641
<212> TYPE: DNA
<213> ORGANISM: Homo sapiens

<400> SEQUENCE: 22

```
ggttacattt tggatcctcg cggagtactg gtcaggcggt taagtcctgt acctaggaaa      60
gagggcgagc tctgggcgc tctccggtgt catgaggagc ttcaaaagag tcaactttgg     120
gactctgcta agcagccaga aggaggctga agagttgctg cccgccttga aggagttcct     180
gtccaaccct ccagctggtt ttcccagcag ccgatctgat gctgagagga gacaagcttg     240
tgatgccatc ctgagggctt gcaaccagca gctgactgct aagctagctt gccctaggca     300
tctggggagc tgctggagc tggcagagct ggcctgtgat ggctacttag tgtctacccc     360
acagcgtcct ccctctacc tggaacgaat tctctttgtc ttactgcgga atgctgctgc     420
acaaggaagc ccagaggcca cactccgcct tgctcagccc ctccatgcct gcttggtgca     480
gtgctctcgc gaggctgctc cccaggacta tgaggccgtg gctcggggca gcttttctct     540
gctttggaag ggggcagaag ccctgttgga acggcgagct gcatttgcag ctcggctgaa     600
ggccttgagc ttcctagtac tcttggagga tgaaagtacc ccttgtgagg ttcctcactt     660
tgcttctcca acagcctgtc gagcggtagc tgcccatcag ctatttgatg ccagtggcca     720
tggtctaaat gaagcagatg ctgatttcct agatgacctg ctctccaggc acgtgatcag     780
agccttggtg ggtgagagag ggagctcttc tgggcttctt tctccccaga gggccctctg     840
cctcttggag ctcaccttgg aacactgccg tcgcttttgc tggagccgcc accatgacaa     900
agccatcagc gcagtggaga aggctcacag ttacctaagg aacaccaatc tagcccctag     960
ccttcagcta tgtcagctgg gggttaagct gctgcaggtt ggggaggaag gacctcaggc    1020
agtggccaag cttctgatca aggcatcagc tgtcctgagc aagagtatgg aggcaccatc    1080
accccccactt cgggcattgt atgagagctg ccagttcttc ctttcaggcc tggaacgagg    1140
caccaagagg cgctatagac ttgatgccat tctgagcctc tttgcttttc ttggagggta    1200
ctgctctctt ctgcagcagc tgcgggatga tggtgtgtat gggggctcct ccaagcaaca    1260
gcagtctttt cttcagatgt actttcaggg acttcacctc tacactgtgg tggtttatga    1320
ctttgcccaa ggctgtcaga tagttgattt ggctgacctg acccaactag tggacagttg    1380
taaatctacc gttgtctgga tgctggaggc cttagagggc ctgtcgggcc aagagctgac    1440
ggaccacatg gggatgaccg cttcttacac cagtaatttg gcctacagct tctatagtca    1500
caagctctat gccgaggcct gtgccatctc tgagccgctc tgtcagcacc tgggtttggt    1560
gaagccaggc acttatcccg aggtgcctcc tgagaagttg cacaggtgct tccggctaca    1620
agtagagagt ttgaagaaac tgggtaaaca ggcccagggc tgcaagatgg tgattttgtg    1680
gctggcagcc ctgcaaccct gtagccctga acacatggct gagccagtca ctttctgggt    1740
tcgggtcaag atggatgcgg ccagggctgg agacaaggag ctacagctaa agactctgcg    1800
agacagcctc agtggctggg acccggagac cctggccctc ctgctgaggg aggagctgca    1860
```

-continued

```
ggcctacaag gcggtgcggg ccgacactgg acaggaacgc ttcaacatca tctgtgacct      1920
cctggagctg agccccgagg agacaccagc cggggcctgg gcacgagcca cccacctggt      1980
agaactggct caggtgctct gctaccacga ctttacgcag cagaccaact gctctgctct      2040
ggatgctatc cgggaagccc tgcagcttct ggactctgtg aggcctgagg cccaggccag      2100
agatcagctt ctggacgata agcacaggcc cttgctgtgg ctttacatct gtactctgga      2160
agccaaaatg caggaaggta tcgagcggga tcggagagcc caggcccctg gtaacttgga      2220
ggaatttgaa gtcaatgacc tgaactatga agataaactc caggaagatc gtttcctata      2280
cagtaacatt gccttcaacc tggctgcaga tgctgctcag tccaaatgcc tggaccaagc      2340
cctggccctg tggaaggagc tgcttacaaa ggggcaggcc ccagctgtac ggtgtctcca      2400
gcagacagca gcctcactgc agatcctagc agccctctac cagctggtgg caaagcccat      2460
gcaggctctg gaggtcctcc tgctgctacg gattgtctct gagagactga aggaccactc      2520
gaaggcagct ggctcctcct gccacatcac ccagctcctc ctgacccteg gctgtcccag      2580
ctatgcccag ttacacctgg aagaggcagc atcgagcctg aagcatctcg atcagactac      2640
tgacacatac ctgctccttt ccctgacctg tgatctgctt cgaagtcaac tctactggac      2700
tcaccagaag gtgaccaagg gtgtctctct gctgctgtct gtgcttcggg atcctgccct      2760
ccagaagtcc tccaaggctt ggtacttgct gcgtgtccag gtcctgcagc tggtggcagc      2820
ttaccttagc ctcccgtcaa caacctctc acactccctg tgggagcagc tctgtgccca      2880
aggctggcag acacctgaga tagctctcat agactcccat aagctcctcc gaagcatcat      2940
cctcctgctg atgggcagtg acattctctc aactcagaaa gcagctgtgg agacatcgtt      3000
tttggactat ggtgaaaatc tggtacaaaa atggcaggtt ctttcagagg tgctgagctg      3060
ctcagagaag ctggtctgcc acctgggccg cctgggtagt gtgagtgaag ccaaggcctt      3120
ttgcttggag gccctaaaac ttacaacaaa gctgcagata ccacgccagt gtgccctgtt      3180
cctggtgctg aagggcgagc tggagctggc ccgcaatgac attgatctct gtcagtcgga      3240
cctgcagcag gttctgttct tgcttgagtc ttgcacagag tttggtgggg tgactcagca      3300
cctggactct gtgaagaagg tccacctgca gaaggggaag cagcaggccc aggtcccctg      3360
tcctccacag ctcccagagg aggagctctt cctaagaggc cctgctctag agctggtggc      3420
cactgtggcc aaggagcctg gccccatagc accttctaca aactcctccc cagtcttgaa      3480
aaccaagccc cagcccatac ccaacttcct gtcccattca cccacctgtg actgctcgct      3540
ctgcgccagc cctgtcctca cagcagtctg tctcgctgg gtattggtca cggcaggggt      3600
gaggctggcc atgggccacc aagcccaggg tctggatctg ctgcaggtcg tgctgaaggg      3660
ctgtcctgaa gccgctgagc gcctcaccca agctctccaa gcttccctga atcataaaaac      3720
acccccctcc ttggttccaa gcctcttgga tgagatcttg gctcaagcat acacactgtt      3780
ggcactggag ggcctgaacc agccatcaaa cgagagcctg cagaaggttc tacagtcagg      3840
gctgaagttt gtagcagcac ggatacccca cctagagccc tggcgagcca gcctgctctt      3900
gatttgggcc ctcacaaaac taggtggcct cagctgctgt actacccaac tttttgcaag      3960
ctcctggggc tggcagccac cattaataaa agtgtccct ggctcagagc cctctaagac      4020
tcagggccaa aaacgttctg gacgagggcg ccaaaagtta gcctctgctc cctgcgcct      4080
caataatacc tctcagaaag gtctggaagg tagaggactg ccctgcacac ctaaaccccc      4140
agaccggatc aggcaagctg gccctcatgt ccccttcacg gtgtttgagg aagtctgccc      4200
tacagagagc aagcctgaag taccccaggc ccccagggta caacagagag tccagacgcg      4260
```

```
cctcaaggtg aacttcagtg atgacagtga cttggaagac cctgtctcag ctgaggcctg   4320
gctggcagag gagcctaaga gacggggcac tgcttcccgg ggccggggggc gagcaaggaa   4380 gggcctgagc ctaaagacgg atgccgtggt tgccccaggt agtgcccctg ggaaccctgg   4440
cctgaatggc aggagccgga gggccaagaa ggtggcatca agacattgtg aggagcggcg   4500
tccccagagg gccagtgacc aggccaggcc tggccctgag atcatgagga ccatccctga   4560
ggaagaactg actgacaact ggagaaaaat gagctttgag atcctcaggg gctctgacgg   4620
ggaagactca gcctcaggtg ggaagactcc agctccgggc cctgaggcag cttctggaga   4680
atgggagctg ctgaggctgg attccagcaa gaagaagctg cccagcccat gcccagacaa   4740
ggagagtgac aaggaccttg gtcctcggct ccggctcccc tcagccccg tagccactgg   4800 tctttctacc ctggactcca tctgtgactc cctgagtgtt gctttccggg gcattagtca   4860
ctgtcctcct agtgggctct atgcccacct ctgccgcttc ctggccttgt gcctgggcca   4920
ccgggatcct tatgccactg ctttccttgt caccgagtct gtctccatca cctgtcgcca   4980
ccagctgctc acccacctcc acagacagct cagcaaggcc cagaagcacc gaggatcact   5040
tgaaatagca gaccagctgc agggactgag ccttcaggag atgcctggag atgtccccct   5100
ggcccgcatc cagcgcctct tttccttcag ggctttggaa tctggccact tcccccagcc   5160
tgaaaaggag agtttccagg agcgcctggc tctgatcccc agtggggtga ctgtgtgtgt   5220
gttggccctg gccacccctcc agcccggaac cgtgggcaac ccctcctgc tgacccggct   5280 ggaaaaggac agtcccccag tcagtgtgca gattcccact ggccagaaca agcttcatct   5340
gcgttcagtc ctgaatgagt ttgatgccat ccagaaggca cagaaagaga acagcagctg   5400
tactgacaag cgagaatggt ggacagggcg gctggcactg gaccacagga tggaggttct   5460
catcgcttcc ctagagaagt ctgtgctggg ctgctggaag gggctgctgc tgccgtccag   5520
tgaggagccc ggccctgccc aggaggcctc ccgcctacag gagctgctac aggactgtgg   5580
ctggaaatat cctgaccgca ctctgctgaa aatcatgctc agtggtgccg gtgccctcac   5640
ccctcaggac attcaggccc tggcctacgg gctgtgccca acccagccag agcgagccca   5700
ggagctcctg aatgaggcag taggacgtct acagggcctg acagtaccaa gcaatagcca   5760
ccttgtcttg gtcctagaca aggacttgca gaagctgccg tgggaaagca tgcccagcct   5820
ccaagcactg cctgtcaccc ggctgccctc cttccgcttc ctactcagct actccatcat   5880
caaagagtat ggggcctcgc cagtgctgag tcaaggggtg gatccacgaa gtaccttcta   5940
tgtcctgaac cctcacaata acctgtcaag cacagaggga caattcgag ccaatttcag   6000 cagtgaagct ggctggagag gagtggttgg ggaggtgcca agacctgaac aggtgcagga   6060
agccctgaca aagcatgatt tgtatatcta tgcaggcat ggggctggtg cccgcttcct   6120
tgatgggcag gctgtcctgc ggctgagctg tcgggcagtg gccctgctgt ttggctgtag   6180
cagtgcggcc ctggctgtgc gtggaaacct ggaggggct ggcatcgtgc tcaagtacat   6240
catggctggt tgccccttgt ttctgggtaa tctctgggat gtgactgacc gcgacattga   6300
ccgctacacg gaagctctgc tgcaaggctg gcttggagca ggcccagggg cccccttct   6360 ctactatgta aaccaggccc gccaagctcc ccgactcaag tatcttattg gggctgcacc   6420
tatagcctat ggcttgcctg tctctctgcg gtaacccat ggagctgtct tattgatgct   6480
agaagcctca taactgttct acctccaagg ttagatttaa tccttaggat aactctttta   6540
aagtgatttt ccccagtgtt ttatatgaaa catttccttt tgatttaacc tcagtataat   6600
```
aaagatacat catttaaacc ctgaaaaaaa aaaaaaaaaa a                6641

<210> SEQ ID NO 23
<211> LENGTH: 707
<212> TYPE: PRT
<213> ORGANISM: Homo sapiens

<400> SEQUENCE: 23

```
Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365
```

```
Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

<210> SEQ ID NO 24
<211> LENGTH: 2387
<212> TYPE: DNA
<213> ORGANISM: Homo sapiens

<400> SEQUENCE: 24
agacacctct gccctcacca tgagcctctg gcagcccctg gtcctggtgc tcctggtgct      60
gggctgctgc tttgctgccc ccagacagcg ccagtccacc cttgtgctct cccctggaga     120
cctgagaacc aatctcaccg acaggcagct ggcagaggaa tacctgtacc gctatggtta     180
```

```
cactcgggtg gcagagatgc gtggagagtc gaaatctctg gggcctgcgc tgctgcttct    240
ccagaagcaa ctgtccctgc ccgagaccgg tgagctggat agcgccacgc tgaaggccat    300
gcgaacccca cggtgcgggg tcccagacct gggcagattc caaacctttg agggcgacct    360
caagtggcac caccacaaca tcacctattg gatccaaaac tactcggaag acttgccgcg    420
ggcggtgatt gacgacgcct ttgcccgcgc cttcgcactg tggagcgcgg tgacgccgct    480
caccttcact cgcgtgtaca gccgggacgc agacatcgtc atccagtttg tgtcgcggga    540
gcacggagac gggtatccct tcgacgggaa ggacgggctc ctggcacacg cctttcctcc    600
tggccccggc attcagggag acgcccattt cgacgatgac gagttgtggt ccctgggcaa    660
gggcgtcgtg gttccaactc ggtttggaaa cgcagatggc gcggcctgcc acttcccctt    720
catcttcgag ggccgctcct actctgcctg caccaccgac ggtcgctccg acggcttgcc    780
ctggtgcagt accacggcca actacgacac cgacgaccgg tttggcttct gccccagcga    840
gagactctac acccaggacg gcaatgctga tgggaaaccc tgccagtttc cattcatctt    900
ccaaggccaa tcctactccg cctgcaccac ggacggtcgc tccgacggct accgctggtg    960
cgccaccacc gccaactacg accgggacaa gctcttcggc ttctgcccga cccgagctga   1020
ctcgacggtg atggggggca actcggcggg ggagctgtgc gtcttcccct tcactttcct   1080
gggtaaggag tactcgacct gtaccagcga gggccgcgga gatgggcgcc tctggtgcgc   1140
taccacctcg aactttgaca gcgacaagaa gtggggcttc tgcccggacc aaggatacag   1200
tttgttcctc gtggcggcgc atgagttcgg ccacgcgctg gcttagatc attcctcagt    1260 gccggaggcg ctcatgtacc ctatgtaccg cttcactgag gggccccct tgcataagga    1320 cgacgtgaat ggcatccggc acctctatgg tcctcgccct gaacctgagc cacggcctcc   1380
aaccaccacc acaccgcagc ccacggctcc cccgacggtc tgccccaccg acccccac    1440 tgtccacccc tcagacgccc cacagctggg ccccacaggt cccccctcag ctggcccac   1500 aggtcccccc actgctggcc cttctacggc cactactgtg cctttgagtc cggtggacga   1560
tgcctgcaac gtgaacatct tcgacgccat cgcggagatt gggaaccagc tgtatttgtt   1620
caaggatggg aagtactggc gattctctga gggcaggggg agccggccgc agggcccctt   1680
ccttatcgcc gacaagtggc ccgcgctgcc ccgcaagctg gactcggtct tgaggagcg    1740 gctctccaag aagcttttct tcttctctgg gcgccaggtg tgggtgtaca caggcgcgtc   1800
ggtgctgggc ccgaggcgtc tggacaagct gggcctggga ccgacgtgg cccaggtgac    1860 cggggccctc cggagtggca gggggaagat gctgctgttc agcgggcggc gcctctggag   1920
gttcgacgtg aaggcgcaga tggtggatcc ccggagcgcc agcgaggtgg accggatgtt   1980
ccccggggtg cctttggaca cgcacgacgt cttccagtac cgagagaaag cctatttctg   2040
ccaggaccgc ttctactggc gcgtgagttc ccggagtgag ttgaaccagg tggaccaagt   2100
gggctacgtg acctatgaca tcctgcagtg ccctgaggac tagggctccc gtcctgcttt   2160
ggcagtgcca tgtaaatccc cactgggacc aaccctgggg aaggagccag tttgccggat   2220
acaaactggt attctgttct ggaggaaagg gaggagtgga ggtgggctgg gccctctctt   2280
ctcacctttg ttttttgttg gagtgttct aataaacttg gattctctaa cctttaaaaa    2340
aaaaaaaaaa aaaaaaaaaa aaaaaaaaaa aaaaaaaaaa aaaaaaa                 2387
```

<210> SEQ ID NO 25
<211> LENGTH: 5058
<212> TYPE: PRT

```
<213> ORGANISM: Homo sapiens
<220> FEATURE:
<221> NAME/KEY: MOD_RES
<222> LOCATION: (283)..(283)
<223> OTHER INFORMATION: Any amino acid
<220> FEATURE:
<221> NAME/KEY: MOD_RES
<222> LOCATION: (2674)..(2674)
<223> OTHER INFORMATION: Any amino acid

<400> SEQUENCE: 25

Met Gly His Ala Gly Cys Gln Phe Lys Ala Leu Leu Trp Lys Asn Trp
1               5                   10                  15

Leu Cys Arg Leu Arg Asn Pro Val Leu Phe Leu Ala Glu Phe Phe Trp
                20                  25                  30

Pro Cys Ile Leu Phe Val Ile Leu Thr Val Leu Arg Phe Gln Glu Pro
            35                  40                  45

Pro Arg Tyr Arg Asp Ile Cys Tyr Leu Gln Pro Arg Asp Leu Pro Ser
        50                  55                  60

Cys Gly Val Ile Pro Phe Val Gln Ser Leu Leu Cys Asn Thr Gly Ser
65                  70                  75                  80

Arg Cys Arg Asn Phe Ser Tyr Glu Gly Ser Met Glu His His Phe Arg
                85                  90                  95

Leu Ser Arg Phe Gln Thr Ala Ala Asp Pro Lys Lys Val Asn Asn Leu
                100                 105                 110

Ala Phe Leu Lys Glu Ile Gln Asp Leu Ala Glu Ile His Gly Met
                115                 120                 125

Met Asp Lys Ala Lys Asn Leu Lys Arg Leu Trp Val Glu Arg Ser Asn
130                 135                 140

Thr Pro Asp Ser Ser Tyr Gly Ser Ser Phe Phe Thr Met Asp Leu Asn
145                 150                 155                 160

Lys Thr Glu Glu Val Ile Leu Lys Leu Glu Ser Leu His Gln Gln Pro
                165                 170                 175

His Ile Trp Asp Phe Leu Leu Leu Pro Arg Leu His Thr Ser His
                180                 185                 190

Asp His Val Glu Asp Gly Met Asp Val Ala Val Asn Leu Leu Gln Thr
                195                 200                 205

Ile Leu Asn Ser Leu Ile Ser Leu Glu Asp Leu Asp Trp Leu Pro Leu
        210                 215                 220

Asn Gln Thr Phe Ser Gln Val Ser Glu Leu Val Leu Asn Val Thr Ile
225                 230                 235                 240

Ser Thr Leu Thr Phe Leu Gln Gln His Gly Val Ala Val Thr Glu Pro
                245                 250                 255

Val Tyr His Leu Ser Met Gln Asn Ile Val Trp Asp Pro Gln Lys Val
                260                 265                 270

Gln Tyr Asp Leu Lys Ser Gln Phe Gly Phe Xaa Asp Leu His Thr Glu
        275                 280                 285

Gln Ile Leu Asn Ser Ser Ala Glu Leu Lys Glu Ile Pro Thr Asp Thr
        290                 295                 300

Ser Leu Glu Lys Met Val Cys Ser Val Leu Ser Ser Thr Ser Glu Asp
305                 310                 315                 320

Glu Ala Glu Lys Trp Gly His Val Gly Gly Cys His Pro Lys Trp Ser
                325                 330                 335

Glu Ala Lys Asn Tyr Leu Val His Ala Val Ser Trp Leu Arg Val Tyr
                340                 345                 350

Gln Gln Val Phe Val Gln Trp Gln Gln Gly Ser Leu Leu Gln Lys Thr
```

```
              355                 360                 365
Leu Thr Gly Met Gly His Ser Leu Glu Ala Leu Arg Asn Gln Phe Glu
370                 375                 380
Glu Glu Ser Lys Pro Trp Lys Val Val Glu Ala Leu His Thr Ala Leu
385                 390                 395                 400
Leu Leu Leu Asn Asp Ser Leu Ser Ala Asp Gly Pro Lys Asp Asn His
                405                 410                 415
Thr Phe Pro Lys Ile Leu Gln His Leu Trp Lys Leu Gln Ser Leu Leu
            420                 425                 430
Gln Asn Leu Pro Gln Trp Pro Ala Leu Lys Arg Phe Leu Gln Leu Asp
            435                 440                 445
Gly Ala Leu Arg Asn Ala Ile Ala Gln Asn Leu His Phe Val Gln Glu
        450                 455                 460
Val Leu Ile Cys Leu Glu Thr Ser Ala Asn Asp Phe Lys Trp Phe Glu
465                 470                 475                 480
Leu Asn Gln Leu Lys Leu Glu Lys Asp Val Phe Phe Trp Glu Leu Lys
                485                 490                 495
Gln Met Leu Ala Lys Asn Ala Val Cys Pro Asn Gly Arg Phe Ser Glu
            500                 505                 510
Lys Glu Val Phe Leu Pro Pro Gly Asn Ser Ser Ile Trp Gly Gly Leu
            515                 520                 525
Gln Gly Leu Leu Cys Tyr Cys Asn Ser Ser Glu Thr Ser Val Leu Asn
        530                 535                 540
Lys Leu Leu Gly Ser Val Glu Asp Ala Asp Arg Ile Leu Gln Glu Val
545                 550                 555                 560
Ile Thr Trp His Lys Asn Met Ser Val Leu Ile Pro Glu Glu Tyr Leu
                565                 570                 575
Asp Trp Gln Glu Leu Glu Met Gln Leu Ser Glu Ala Ser Leu Ser Cys
            580                 585                 590
Thr Arg Leu Phe Leu Leu Leu Gly Ala Asp Pro Ser Pro Glu Asn Asp
            595                 600                 605
Val Phe Ser Ser Asp Cys Lys His Gln Leu Val Ser Thr Val Ile Phe
        610                 615                 620
His Thr Leu Glu Lys Thr Gln Phe Phe Leu Glu Gln Ala Tyr Tyr Trp
625                 630                 635                 640
Lys Ala Phe Lys Lys Phe Ile Arg Lys Thr Cys Glu Val Ala Gln Tyr
                645                 650                 655
Val Asn Met Gln Glu Ser Phe Gln Asn Arg Leu Leu Ala Phe Pro Glu
            660                 665                 670
Glu Ser Pro Cys Phe Glu Glu Asn Met Asp Trp Lys Met Ile Ser Asp
            675                 680                 685
Asn Tyr Phe Gln Phe Leu Asn Leu Leu Lys Ser Pro Thr Ala Ser
        690                 695                 700
Ile Ser Arg Ala Leu Asn Phe Thr Lys His Leu Leu Met Met Glu Lys
705                 710                 715                 720
Lys Leu His Thr Leu Glu Asp Glu Gln Met Asn Phe Leu Leu Ser Phe
                725                 730                 735
Val Glu Phe Phe Glu Lys Leu Leu Pro Asn Leu Phe Asp Ser Ser
            740                 745                 750
Ile Val Pro Ser Phe His Ser Leu Pro Ser Leu Thr Glu Asp Ile Leu
            755                 760                 765
Asn Ile Ser Ser Leu Trp Thr Asn His Leu Lys Ser Leu Lys Arg Asp
        770                 775                 780
```

-continued

```
Pro Ser Ala Thr Asp Ala Gln Lys Leu Leu Glu Phe Gly Asn Glu Val
785                 790                 795                 800

Ile Trp Lys Met Gln Thr Leu Gly Ser His Trp Ile Arg Lys Glu Pro
            805                 810                 815

Lys Asn Leu Leu Arg Phe Ile Glu Leu Ile Leu Phe Gly Ile Asn Pro
        820                 825                 830

Lys Leu Leu Glu Leu Trp Ala Tyr Gly Ile Ser Lys Gly Lys Arg Ala
    835                 840                 845

Lys Leu Glu Asn Phe Phe Thr Leu Leu Asn Phe Ser Val Pro Glu Asn
    850                 855                 860

Glu Ile Leu Ser Thr Ser Phe Asn Phe Ser Gln Leu Phe His Ser Asp
865                 870                 875                 880

Trp Pro Lys Ser Pro Ala Met Asn Ile Asp Phe Val Arg Leu Ser Glu
            885                 890                 895

Ala Ile Ile Thr Ser Leu His Glu Phe Gly Phe Leu Glu Gln Glu Gln
        900                 905                 910

Ile Ser Glu Ala Leu Asn Thr Val Tyr Ala Ile Arg Asn Ala Ser Asp
    915                 920                 925

Leu Phe Ser Ala Leu Ser Glu Pro Gln Lys Gln Glu Val Asp Lys Ile
    930                 935                 940

Leu Thr His Ile His Leu Asn Val Phe Gln Asp Lys Asp Ser Ala Leu
945                 950                 955                 960

Leu Leu Gln Ile Tyr Ser Ser Phe Tyr Arg Tyr Ile Tyr Glu Leu Leu
            965                 970                 975

Asn Ile Gln Ser Arg Gly Ser Ser Leu Thr Phe Leu Thr Gln Ile Ser
        980                 985                 990

Lys His Ile Leu Asp Ile Ile Lys Gln Phe Asn Phe Gln Asn Ile Ser
    995                 1000                1005

Lys Ala Phe Ala Phe Leu Phe Lys Thr Ala Glu Val Leu Gly Gly
    1010                1015                1020

Ile Ser Asn Val Ser Tyr Cys Gln Gln Leu Leu Ser Ile Phe Asn
    1025                1030                1035

Phe Leu Glu Leu Gln Ala Gln Ser Phe Met Ser Thr Glu Gly Gln
    1040                1045                1050

Glu Leu Glu Val Ile His Thr Thr Leu Thr Gly Leu Lys Gln Leu
    1055                1060                1065

Leu Ile Ile Asp Glu Asp Phe Arg Ile Ser Leu Phe Gln Tyr Met
    1070                1075                1080

Ser Gln Phe Phe Asn Ser Ser Val Glu Asp Leu Leu Asp Asn Lys
    1085                1090                1095

Cys Leu Ile Ser Asp Asn Lys His Ile Ser Ser Val Asn Tyr Ser
    1100                1105                1110

Thr Ser Glu Glu Ser Ser Phe Val Phe Pro Leu Ala Gln Ile Phe
    1115                1120                1125

Ser Asn Leu Ser Ala Asn Val Ser Val Phe Asn Lys Phe Met Ser
    1130                1135                1140

Ile His Cys Thr Val Ser Trp Leu Gln Met Trp Thr Glu Ile Trp
    1145                1150                1155

Glu Thr Ile Ser Gln Leu Phe Lys Phe Asp Met Asn Val Phe Thr
    1160                1165                1170

Ser Leu His His Gly Phe Thr Gln Leu Leu Asp Glu Leu Glu Asp
    1175                1180                1185
```

-continued

```
Asp Val Lys Val Ser Lys Ser Cys Gln Gly Ile Leu Pro Thr His
    1190            1195                1200
Asn Val Ala Arg Leu Ile Leu Asn Leu Phe Lys Asn Val Thr Gln
    1205            1210                1215
Ala Asn Asp Phe His Asn Trp Glu Asp Phe Leu Asp Leu Arg Asp
    1220            1225                1230
Phe Leu Val Ala Leu Gly Asn Ala Leu Val Ser Val Lys Lys Leu
    1235            1240                1245
Asn Leu Glu Gln Val Glu Lys Ser Leu Phe Thr Met Glu Ala Ala
    1250            1255                1260
Leu His Gln Leu Lys Thr Phe Pro Phe Asn Glu Ser Thr Ser Arg
    1265            1270                1275
Glu Phe Leu Asn Ser Leu Leu Glu Val Phe Ile Glu Phe Ser Ser
    1280            1285                1290
Thr Ser Glu Tyr Ile Val Arg Asn Leu Asp Ser Ile Asn Asp Phe
    1295            1300                1305
Leu Ser Asn Asn Leu Thr Asn Tyr Gly Glu Lys Phe Glu Asn Ile
    1310            1315                1320
Ile Thr Glu Leu Arg Glu Ala Ile Val Phe Leu Arg Asn Val Ser
    1325            1330                1335
His Asp Arg Asp Leu Phe Ser Cys Ala Asp Ile Phe Gln Asn Val
    1340            1345                1350
Thr Glu Cys Ile Leu Glu Asp Gly Phe Leu Tyr Val Asn Thr Ser
    1355            1360                1365
Gln Arg Met Leu Arg Ile Leu Asp Thr Leu Asn Ser Thr Phe Ser
    1370            1375                1380
Ser Glu Asn Thr Ile Ser Ser Leu Lys Gly Cys Ile Val Trp Leu
    1385            1390                1395
Asp Val Ile Asn His Leu Tyr Leu Leu Ser Asn Ser Ser Phe Ser
    1400            1405                1410
Gln Gly Arg Leu Gln Asn Ile Leu Gly Asn Phe Arg Asp Ile Glu
    1415            1420                1425
Asn Lys Met Asn Ser Ile Leu Lys Ile Val Thr Trp Val Leu Asn
    1430            1435                1440
Ile Lys Lys Pro Leu Cys Ser Ser Asn Gly Ser His Ile Asn Cys
    1445            1450                1455
Val Asn Ile Tyr Leu Lys Asp Val Thr Asp Phe Leu Asn Ile Val
    1460            1465                1470
Leu Thr Thr Val Phe Glu Lys Glu Lys Pro Lys Phe Glu Ile
    1475            1480                1485
Leu Leu Ala Leu Leu Asn Asp Ser Thr Lys Gln Val Arg Met Ser
    1490            1495                1500
Ile Asn Asn Leu Thr Thr Asp Phe Asp Phe Ala Ser Gln Ser Asn
    1505            1510                1515
Trp Arg Tyr Phe Thr Glu Leu Ile Leu Arg Pro Ile Glu Met Ser
    1520            1525                1530
Asp Glu Ile Pro Asn Gln Phe Gln Asn Ile Trp Leu His Leu Ile
    1535            1540                1545
Thr Leu Gly Lys Glu Phe Gln Lys Leu Val Lys Gly Ile Tyr Phe
    1550            1555                1560
Asn Ile Leu Glu Asn Asn Ser Ser Ser Lys Thr Glu Asn Leu Leu
    1565            1570                1575
Asn Ile Phe Ala Thr Ser Pro Lys Glu Lys Asp Val Asn Ser Val
```

```
            1580                1585                1590

Gly Asn Ser Ile Tyr His Leu Ala Ser Tyr Leu Ala Phe Ser Leu
    1595                1600                1605

Ser His Asp Leu Gln Asn Ser Pro Lys Ile Ile Ile Ser Pro Glu
    1610                1615                1620

Ile Met Lys Ala Thr Gly Leu Gly Ile Gln Leu Ile Arg Asp Val
    1625                1630                1635

Phe Asn Ser Leu Met Pro Val Val His His Thr Ser Pro Gln Asn
    1640                1645                1650

Ala Gly Tyr Met Gln Ala Leu Lys Lys Val Thr Ser Val Met Arg
    1655                1660                1665

Thr Leu Lys Lys Ala Asp Ile Asp Leu Leu Val Asp Gln Leu Glu
    1670                1675                1680

Gln Val Ser Val Asn Leu Met Asp Phe Phe Lys Asn Ile Ser Ser
    1685                1690                1695

Val Gly Thr Gly Asn Leu Val Val Asn Leu Leu Val Gly Leu Met
    1700                1705                1710

Glu Lys Phe Ala Asp Ser Ser His Ser Trp Asn Val Asn His Leu
    1715                1720                1725

Leu Gln Leu Ser Arg Leu Phe Pro Lys Asp Val Val Asp Ala Val
    1730                1735                1740

Ile Asp Val Tyr Tyr Val Leu Pro His Ala Val Arg Leu Leu Gln
    1745                1750                1755

Gly Val Pro Gly Lys Asn Ile Thr Glu Gly Leu Lys Asp Val Tyr
    1760                1765                1770

Ser Phe Thr Leu Leu His Gly Ile Thr Ile Ser Asn Ile Thr Lys
    1775                1780                1785

Glu Asp Phe Ala Ile Val Ile Lys Ile Leu Leu Asp Thr Ile Glu
    1790                1795                1800

Leu Val Ser Asp Lys Pro Asp Ile Ile Ser Glu Ala Leu Ala Cys
    1805                1810                1815

Phe Pro Val Val Trp Cys Trp Asn His Thr Asn Ser Gly Phe Arg
    1820                1825                1830

Gln Asn Ser Lys Ile Asp Pro Cys Asn Val His Gly Leu Met Ser
    1835                1840                1845

Ser Ser Phe Tyr Gly Lys Val Ala Ser Ile Leu Asp His Phe His
    1850                1855                1860

Leu Ser Pro Gln Gly Glu Asp Ser Pro Cys Ser Asn Glu Ser Ser
    1865                1870                1875

Arg Met Glu Ile Thr Arg Lys Val Val Cys Ile His Glu Leu
    1880                1885                1890

Val Asp Trp Asn Ser Ile Leu Leu Glu Leu Ser Glu Val Phe His
    1895                1900                1905

Val Asn Ile Ser Leu Val Lys Thr Val Gln Lys Phe Trp His Lys
    1910                1915                1920

Ile Leu Pro Phe Val Pro Pro Ser Ile Asn Gln Thr Arg Asp Ser
    1925                1930                1935

Ile Ser Glu Leu Cys Pro Ser Gly Ser Ile Lys Gln Val Ala Leu
    1940                1945                1950

Gln Ile Ile Glu Lys Leu Lys Asn Val Asn Phe Thr Lys Val Thr
    1955                1960                1965

Ser Gly Glu Asn Ile Leu Asp Lys Leu Ser Ser Leu Asn Lys Ile
    1970                1975                1980
```

```
Leu Asn Ile Asn Glu Asp Thr Glu Thr Ser Val Gln Asn Ile Ile
1985                1990                1995

Ser Ser Asn Leu Glu Arg Thr Val Gln Leu Ile Ser Glu Asp Trp
2000                2005                2010

Ser Leu Glu Lys Ser Thr His Asn Leu Leu Ser Leu Phe Met Met
2015                2020                2025

Leu Gln Asn Ala Asn Val Thr Gly Ser Ser Leu Glu Ala Leu Ser
2030                2035                2040

Ser Phe Ile Glu Lys Ser Glu Thr Pro Tyr Asn Phe Glu Glu Leu
2045                2050                2055

Trp Pro Lys Phe Gln Gln Ile Met Lys Asp Leu Thr Gln Asp Phe
2060                2065                2070

Arg Ile Arg His Leu Leu Ser Glu Met Asn Lys Gly Ile Lys Ser
2075                2080                2085

Ile Asn Ser Met Ala Leu Gln Lys Ile Thr Leu Gln Phe Ala His
2090                2095                2100

Phe Leu Glu Ile Leu Asp Ser Pro Ser Leu Lys Thr Leu Glu Ile
2105                2110                2115

Ile Glu Asp Phe Leu Leu Val Thr Lys Asn Trp Leu Gln Glu Tyr
2120                2125                2130

Ala Asn Glu Asp Tyr Ser Arg Met Ile Glu Thr Leu Phe Ile Pro
2135                2140                2145

Val Thr Asn Glu Ser Ser Thr Glu Asp Ile Ala Leu Leu Ala Lys
2150                2155                2160

Ala Ile Ala Thr Phe Trp Gly Ser Leu Lys Asn Ile Ser Arg Ala
2165                2170                2175

Gly Asn Phe Asp Val Ala Phe Leu Thr His Leu Leu Asn Gln Glu
2180                2185                2190

Gln Leu Thr Asn Phe Ser Val Val Gln Leu Leu Phe Glu Asn Ile
2195                2200                2205

Leu Ile Asn Leu Ile Asn Asn Leu Ala Gly Asn Ser Gln Glu Ala
2210                2215                2220

Ala Trp Asn Leu Asn Asp Thr Asp Leu Gln Ile Met Asn Phe Ile
2225                2230                2235

Asn Leu Ile Leu Asn His Met Gln Ser Glu Thr Ser Arg Lys Thr
2240                2245                2250

Val Leu Ser Leu Arg Ser Ile Val Asp Phe Thr Glu Gln Phe Leu
2255                2260                2265

Lys Thr Phe Phe Ser Leu Phe Leu Lys Glu Asp Ser Glu Asn Lys
2270                2275                2280

Ile Ser Leu Leu Leu Lys Tyr Phe His Lys Asp Val Ile Ala Glu
2285                2290                2295

Met Ser Phe Val Pro Lys Asp Lys Ile Leu Glu Ile Leu Lys Leu
2300                2305                2310

Asp Gln Phe Leu Thr Leu Met Ile Gln Asp Arg Leu Met Asn Ile
2315                2320                2325

Phe Ser Ser Leu Lys Glu Thr Ile Tyr His Leu Met Lys Ser Ser
2330                2335                2340

Phe Ile Leu Asp Asn Gly Glu Phe Tyr Phe Asp Thr His Gln Gly
2345                2350                2355

Leu Lys Phe Met Gln Asp Leu Phe Asn Ala Leu Leu Arg Glu Thr
2360                2365                2370
```

```
Ser Met Lys Asn Lys Thr Glu Asn Asn Ile Asp Phe Phe Thr Val
2375                2380                2385

Val Ser Gln Leu Phe Phe His Val Asn Lys Ser Glu Asp Leu Phe
2390                2395                2400

Lys Leu Asn Gln Asp Leu Gly Ser Ala Leu His Leu Val Arg Glu
2405                2410                2415

Cys Ser Thr Glu Met Ala Arg Leu Leu Asp Thr Ile Leu His Ser
2420                2425                2430

Pro Asn Lys Asp Phe Tyr Ala Leu Tyr Pro Thr Leu Gln Glu Val
2435                2440                2445

Ile Leu Ala Asn Leu Thr Asp Leu Leu Phe Phe Ile Asn Asn Ser
2450                2455                2460

Phe Pro Leu Arg Asn Arg Ala Thr Leu Glu Ile Thr Lys Arg Leu
2465                2470                2475

Val Gly Ala Ile Ser Arg Ala Ser Glu Glu Ser His Val Leu Lys
2480                2485                2490

Pro Leu Leu Glu Met Ser Gly Thr Leu Val Met Leu Leu Asn Asp
2495                2500                2505

Ser Ala Asp Leu Arg Asp Leu Ala Thr Ser Met Asp Ser Ile Val
2510                2515                2520

Lys Leu Leu Lys Leu Val Lys Lys Val Ser Gly Lys Met Ser Thr
2525                2530                2535

Val Phe Lys Thr His Phe Ile Ser Asn Thr Lys Asp Ser Val Lys
2540                2545                2550

Phe Phe Asp Thr Leu Tyr Ser Ile Met Gln Gln Ser Val Gln Asn
2555                2560                2565

Leu Val Lys Glu Ile Ala Thr Leu Lys Lys Ile Asp His Phe Thr
2570                2575                2580

Phe Glu Lys Ile Asn Asp Leu Leu Val Pro Phe Leu Asp Leu Ala
2585                2590                2595

Phe Glu Met Ile Gly Val Glu Pro Tyr Ile Ser Ser Asn Ser Asp
2600                2605                2610

Ile Phe Ser Met Ser Pro Ser Ile Leu Ser Tyr Met Asn Gln Ser
2615                2620                2625

Lys Asp Phe Ser Asp Ile Leu Glu Glu Ile Ala Glu Phe Leu Thr
2630                2635                2640

Ser Val Lys Met Asn Leu Glu Asp Met Arg Ser Leu Ala Val Ala
2645                2650                2655

Phe Asn Asn Glu Thr Gln Thr Phe Ser Met Asp Ser Val Asn Leu
2660                2665                2670

Xaa Glu Glu Ile Leu Gly Cys Leu Val Pro Ile Asn Asn Ile Thr
2675                2680                2685

Asn Gln Met Asp Phe Leu Tyr Pro Asn Pro Ile Ser Thr His Ser
2690                2695                2700

Gly Pro Gln Asp Ile Lys Trp Glu Ile Ile His Glu Val Ile Leu
2705                2710                2715

Phe Leu Asp Lys Ile Leu Ser Gln Asn Ser Thr Glu Ile Gly Ser
2720                2725                2730

Phe Leu Lys Met Val Ile Cys Leu Thr Leu Glu Ala Leu Trp Lys
2735                2740                2745

Asn Leu Lys Lys Asp Asn Trp Asn Val Ser Asn Val Leu Met Thr
2750                2755                2760

Phe Thr Gln His Pro Asn Asn Leu Leu Lys Thr Ile Glu Thr Val
```

```
              2765                2770                2775

Leu Glu Ala Ser Ser Gly Ile Lys Ser Asp Tyr Glu Gly Asp Leu
            2780                2785                2790

Asn Lys Ser Leu Tyr Phe Asp Thr Pro Leu Ser Gln Asn Ile Thr
            2795                2800                2805

His His Gln Leu Glu Lys Ala Ile His Asn Val Leu Ser Arg Ile
            2810                2815                2820

Ala Leu Trp Arg Lys Gly Leu Arg Phe Asn Asn Ser Glu Trp Ile
            2825                2830                2835

Thr Ser Thr Arg Thr Leu Phe Gln Pro Leu Phe Glu Ile Phe Ile
            2840                2845                2850

Lys Ala Thr Thr Gly Lys Asn Val Thr Ser Glu Lys Glu Glu Arg
            2855                2860                2865

Thr Glu Lys Glu Met Ile Asp Phe Pro Tyr Ser Phe Lys Pro Phe
            2870                2875                2880

Phe Cys Leu Glu Lys Tyr Leu Gly Gly Leu Phe Val Leu Thr Lys
            2885                2890                2895

Tyr Trp Gln Gln Ile Pro Leu Thr Asp Gln Ser Val Val Glu Ile
            2900                2905                2910

Cys Glu Val Phe Gln Gln Thr Val Lys Pro Ser Glu Ala Met Glu
            2915                2920                2925

Met Leu Gln Lys Val Lys Met Met Val Arg Val Leu Thr Ile
            2930                2935                2940

Val Ala Glu Asn Pro Ser Trp Thr Lys Asp Ile Leu Cys Ala Thr
            2945                2950                2955

Leu Ser Cys Lys Gln Asn Gly Ile Arg His Leu Ile Leu Ser Ala
            2960                2965                2970

Ile Gln Gly Val Thr Leu Ala Gln Asp His Phe Gln Glu Ile Glu
            2975                2980                2985

Lys Ile Trp Ser Ser Pro Asn Gln Leu Asn Cys Glu Ser Leu Ser
            2990                2995                3000

Lys Asn Leu Ser Ser Thr Leu Glu Ser Phe Lys Ser Ser Leu Glu
            3005                3010                3015

Asn Ala Thr Gly Gln Asp Cys Thr Ser Gln Pro Arg Leu Glu Thr
            3020                3025                3030

Val Gln Gln His Leu Tyr Met Leu Ala Lys Ser Leu Glu Glu Thr
            3035                3040                3045

Trp Ser Ser Gly Asn Pro Ile Met Thr Phe Leu Ser Asn Phe Thr
            3050                3055                3060

Val Thr Glu Asp Val Lys Ile Lys Asp Leu Met Lys Asn Ile Thr
            3065                3070                3075

Lys Leu Thr Glu Glu Leu Arg Ser Ser Ile Gln Ile Ser Asn Glu
            3080                3085                3090

Thr Ile His Ser Ile Leu Glu Ala Asn Ile Ser His Ser Lys Val
            3095                3100                3105

Leu Phe Ser Ala Leu Thr Val Ala Leu Ser Gly Lys Cys Asp Gln
            3110                3115                3120

Glu Ile Leu His Leu Leu Leu Thr Phe Pro Lys Gly Glu Lys Ser
            3125                3130                3135

Trp Ile Ala Ala Glu Glu Leu Cys Ser Leu Pro Gly Ser Lys Val
            3140                3145                3150

Tyr Ser Leu Ile Val Leu Leu Ser Arg Asn Leu Asp Val Arg Ala
            3155                3160                3165
```

```
-continued

Phe Ile Tyr Lys Thr Leu Met Pro Ser Glu Ala Asn Gly Leu Leu
3170                3175                3180

Asn Ser Leu Leu Asp Ile Val Ser Ser Leu Ser Ala Leu Leu Ala
3185                3190                3195

Lys Ala Gln His Val Phe Glu Tyr Leu Pro Glu Phe Leu His Thr
3200                3205                3210

Phe Lys Ile Thr Ala Leu Leu Glu Thr Leu Asp Phe Gln Gln Val
3215                3220                3225

Ser Gln Asn Val Gln Ala Arg Ser Ser Ala Phe Gly Ser Phe Gln
3230                3235                3240

Phe Val Met Lys Met Val Cys Lys Asp Gln Ala Ser Phe Leu Ser
3245                3250                3255

Asp Ser Asn Met Phe Ile Asn Leu Pro Arg Val Lys Glu Leu Leu
3260                3265                3270

Glu Asp Asp Lys Glu Lys Phe Asn Ile Pro Glu Asp Ser Thr Pro
3275                3280                3285

Phe Cys Leu Lys Leu Tyr Gln Glu Ile Leu Gln Leu Pro Asn Gly
3290                3295                3300

Ala Leu Val Trp Thr Phe Leu Lys Pro Ile Leu His Gly Lys Ile
3305                3310                3315

Leu Tyr Thr Pro Asn Thr Pro Glu Ile Asn Lys Val Ile Gln Lys
3320                3325                3330

Ala Asn Tyr Thr Phe Tyr Ile Val Asp Lys Leu Lys Thr Leu Ser
3335                3340                3345

Glu Thr Leu Leu Glu Met Ser Ser Leu Phe Gln Arg Ser Gly Ser
3350                3355                3360

Gly Gln Met Phe Asn Gln Leu Gln Glu Ala Leu Arg Asn Lys Phe
3365                3370                3375

Val Arg Asn Phe Val Glu Asn Gln Leu His Ile Asp Val Asp Lys
3380                3385                3390

Leu Thr Glu Lys Leu Gln Thr Tyr Gly Gly Leu Leu Asp Glu Met
3395                3400                3405

Phe Asn His Ala Gly Ala Gly Arg Phe Arg Phe Leu Gly Ser Ile
3410                3415                3420

Leu Val Asn Leu Ser Ser Cys Val Ala Leu Asn Arg Phe Gln Ala
3425                3430                3435

Leu Gln Ser Val Asp Ile Leu Glu Thr Lys Ala His Glu Leu Leu
3440                3445                3450

Gln Gln Asn Ser Phe Leu Ala Ser Ile Ile Phe Ser Asn Ser Leu
3455                3460                3465

Phe Asp Lys Asn Phe Arg Ser Glu Ser Val Lys Leu Pro Pro His
3470                3475                3480

Val Ser Tyr Thr Ile Arg Thr Asn Val Leu Tyr Ser Val Arg Thr
3485                3490                3495

Asp Val Val Lys Asn Pro Ser Trp Lys Phe His Pro Gln Asn Leu
3500                3505                3510

Pro Ala Asp Gly Phe Lys Tyr Asn Tyr Val Phe Ala Pro Leu Gln
3515                3520                3525

Asp Met Ile Glu Arg Ala Ile Ile Leu Val Gln Thr Gly Gln Glu
3530                3535                3540

Ala Leu Glu Pro Ala Ala Gln Thr Gln Ala Ala Pro Tyr Pro Cys
3545                3550                3555
```

```
His Thr Ser Asp Leu Phe Leu Asn Asn Val Gly Phe Phe Phe Pro
    3560            3565            3570

Leu Ile Met Met Leu Thr Trp Met Val Ser Val Ala Ser Met Val
    3575            3580            3585

Arg Lys Leu Val Tyr Glu Gln Glu Ile Gln Ile Glu Glu Tyr Met
    3590            3595            3600

Arg Met Met Gly Val His Pro Val Ile His Phe Leu Ala Trp Phe
    3605            3610            3615

Leu Glu Asn Met Ala Val Leu Thr Ile Ser Ser Ala Thr Leu Ala
    3620            3625            3630

Ile Val Leu Lys Thr Ser Gly Ile Phe Ala His Ser Asn Thr Phe
    3635            3640            3645

Ile Val Phe Leu Phe Leu Leu Asp Phe Gly Met Ser Val Val Met
    3650            3655            3660

Leu Ser Tyr Leu Leu Ser Ala Phe Phe Ser Gln Ala Asn Thr Ala
    3665            3670            3675

Ala Leu Cys Thr Ser Leu Val Tyr Met Ile Ser Phe Leu Pro Tyr
    3680            3685            3690

Ile Val Leu Leu Val Leu His Asn Gln Leu Ser Phe Val Asn Gln
    3695            3700            3705

Thr Phe Leu Cys Leu Leu Ser Thr Thr Ala Phe Gly Gln Gly Val
    3710            3715            3720

Phe Phe Ile Thr Phe Leu Glu Gly Gln Glu Thr Gly Ile Gln Trp
    3725            3730            3735

Asn Asn Met Tyr Gln Ala Leu Glu Gln Gly Gly Met Thr Phe Gly
    3740            3745            3750

Trp Val Cys Trp Met Ile Leu Phe Asp Ser Ser Leu Tyr Phe Leu
    3755            3760            3765

Cys Gly Trp Tyr Leu Ser Asn Leu Ile Pro Gly Thr Phe Gly Leu
    3770            3775            3780

Arg Lys Pro Trp Tyr Phe Pro Phe Thr Ala Ser Tyr Trp Lys Ser
    3785            3790            3795

Val Gly Phe Leu Val Glu Lys Arg Gln Tyr Phe Leu Ser Ser Ser
    3800            3805            3810

Leu Phe Phe Phe Asn Glu Asn Phe Asp Asn Lys Gly Ser Ser Leu
    3815            3820            3825

Gln Asn Arg Glu Gly Glu Leu Glu Gly Ser Ala Pro Gly Val Thr
    3830            3835            3840

Leu Val Ser Val Thr Lys Glu Tyr Glu Gly His Lys Ala Val Val
    3845            3850            3855

Gln Asp Leu Ser Leu Thr Phe Tyr Arg Asp Gln Ile Thr Ala Leu
    3860            3865            3870

Leu Gly Thr Asn Gly Ala Gly Lys Thr Thr Ile Ile Ser Met Leu
    3875            3880            3885

Thr Gly Leu His Pro Pro Thr Ser Gly Thr Ile Ile Ile Asn Gly
    3890            3895            3900

Lys Asn Leu Gln Thr Asp Leu Ser Arg Val Arg Met Glu Leu Gly
    3905            3910            3915

Val Cys Pro Gln Gln Asp Ile Leu Leu Asp Asn Leu Thr Val Arg
    3920            3925            3930

Glu His Leu Leu Leu Phe Ala Ser Ile Lys Ala Pro Gln Trp Thr
    3935            3940            3945

Lys Lys Glu Leu His Gln Gln Val Asn Gln Thr Leu Gln Asp Val
```

```
                    3950                    3955                    3960
Asp Leu Thr Gln His Gln His Lys Gln Thr Arg Ala Leu Ser Gly
    3965                    3970                    3975
Gly Leu Lys Arg Lys Leu Ser Leu Gly Ile Ala Phe Met Gly Met
    3980                    3985                    3990
Ser Arg Thr Val Val Leu Asp Glu Pro Thr Ser Gly Val Asp Pro
    3995                    4000                    4005
Cys Ser Arg His Ser Leu Trp Asp Ile Leu Leu Lys Tyr Arg Glu
    4010                    4015                    4020
Gly Arg Thr Ile Ile Phe Thr Thr His His Leu Asp Glu Ala Glu
    4025                    4030                    4035
Ala Leu Ser Asp Arg Val Ala Val Leu Gln His Gly Arg Leu Arg
    4040                    4045                    4050
Cys Cys Gly Pro Pro Phe Cys Leu Lys Glu Ala Tyr Gly Gln Gly
    4055                    4060                    4065
Leu Arg Leu Thr Leu Thr Arg Gln Pro Ser Val Leu Glu Ala His
    4070                    4075                    4080
Asp Leu Lys Asp Met Ala Cys Val Thr Ser Leu Ile Lys Ile Tyr
    4085                    4090                    4095
Ile Pro Gln Ala Phe Leu Lys Asp Ser Ser Gly Ser Glu Leu Thr
    4100                    4105                    4110
Tyr Thr Ile Pro Lys Asp Thr Asp Lys Ala Cys Leu Lys Gly Leu
    4115                    4120                    4125
Phe Gln Ala Leu Asp Glu Asn Leu His Gln Leu His Leu Thr Gly
    4130                    4135                    4140
Tyr Gly Ile Ser Asp Thr Thr Leu Glu Glu Val Phe Leu Met Leu
    4145                    4150                    4155
Leu Gln Asp Ser Asn Lys Lys Ser His Ile Ala Leu Gly Thr Glu
    4160                    4165                    4170
Ser Glu Leu Gln Asn His Arg Pro Thr Gly His Leu Ser Gly Tyr
    4175                    4180                    4185
Cys Gly Ser Leu Ala Arg Pro Ala Thr Val Gln Gly Val Gln Leu
    4190                    4195                    4200
Leu Arg Ala Gln Val Ala Ala Ile Leu Ala Arg Arg Leu Arg Arg
    4205                    4210                    4215
Thr Leu Arg Ala Gly Lys Ser Thr Leu Ala Asp Leu Leu Leu Pro
    4220                    4225                    4230
Val Leu Phe Val Ala Leu Ala Met Gly Leu Phe Met Val Arg Pro
    4235                    4240                    4245
Leu Ala Thr Glu Tyr Pro Pro Leu Arg Leu Thr Pro Gly His Tyr
    4250                    4255                    4260
Gln Arg Ala Glu Thr Tyr Phe Phe Ser Ser Gly Gly Asp Asn Leu
    4265                    4270                    4275
Asp Leu Thr Arg Val Leu Leu Arg Lys Phe Arg Asp Gln Asp Leu
    4280                    4285                    4290
Pro Cys Ala Asp Leu Asn Pro Arg Gln Lys Asn Ser Ser Cys Trp
    4295                    4300                    4305
Arg Thr Asp Pro Phe Ser His Pro Glu Phe Gln Asp Ser Cys Gly
    4310                    4315                    4320
Cys Leu Lys Cys Pro Asn Arg Ser Ala Ser Ala Pro Tyr Leu Thr
    4325                    4330                    4335
Asn His Leu Gly His Thr Leu Leu Asn Leu Ser Gly Phe Asn Met
    4340                    4345                    4350
```

```
Glu Glu Tyr Leu Leu Ala Pro Ser Glu Lys Pro Arg Leu Gly Gly
4355                4360                4365

Trp Ser Phe Gly Leu Lys Ile Pro Ser Glu Ala Gly Gly Ala Asn
4370                4375                4380

Gly Asn Ile Ser Lys Pro Pro Thr Leu Ala Lys Val Trp Tyr Asn
4385                4390                4395

Gln Lys Gly Phe His Ser Leu Pro Ser Tyr Leu Asn His Leu Asn
4400                4405                4410

Asn Leu Ile Leu Trp Gln His Leu Pro Pro Thr Val Asp Trp Arg
4415                4420                4425

Gln Tyr Gly Ile Thr Leu Tyr Ser His Pro Tyr Gly Gly Ala Leu
4430                4435                4440

Leu Asn Glu Asp Lys Ile Leu Glu Ser Ile Arg Gln Cys Gly Val
4445                4450                4455

Ala Leu Cys Ile Val Leu Gly Phe Ser Ile Leu Ser Ala Ser Ile
4460                4465                4470

Gly Ser Ser Val Val Arg Asp Arg Val Ile Gly Ala Lys Arg Leu
4475                4480                4485

Gln His Ile Ser Gly Leu Gly Tyr Arg Met Tyr Trp Phe Thr Asn
4490                4495                4500

Phe Leu Tyr Asp Met Leu Phe Tyr Leu Val Ser Val Cys Leu Cys
4505                4510                4515

Val Ala Val Ile Val Ala Phe Gln Leu Thr Ala Phe Thr Phe Arg
4520                4525                4530

Lys Asn Leu Ala Ala Thr Ala Leu Leu Leu Ser Leu Phe Gly Tyr
4535                4540                4545

Ala Thr Leu Pro Trp Met Tyr Leu Met Ser Arg Ile Phe Ser Ser
4550                4555                4560

Ser Asp Val Ala Phe Ile Ser Tyr Val Ser Leu Asn Phe Ile Phe
4565                4570                4575

Gly Leu Cys Thr Met Pro Ile Thr Ile Met Pro Arg Leu Leu Ala
4580                4585                4590

Ile Ile Ser Lys Ala Lys Asn Leu Gln Asn Ile Tyr Asp Val Leu
4595                4600                4605

Lys Trp Val Phe Thr Ile Phe Pro Gln Phe Cys Leu Gly Gln Gly
4610                4615                4620

Leu Val Glu Leu Cys Tyr Asn Gln Ile Lys Tyr Asp Leu Thr His
4625                4630                4635

Asn Phe Gly Ile Asp Ser Tyr Val Ser Pro Phe Glu Met Asn Phe
4640                4645                4650

Leu Gly Trp Ile Phe Val Gln Leu Ala Ser Gln Gly Thr Val Leu
4655                4660                4665

Leu Leu Leu Arg Val Leu Leu His Trp Asp Leu Leu Arg Trp Pro
4670                4675                4680

Arg Gly His Ser Thr Leu Gln Gly Thr Val Lys Ser Ser Lys Asp
4685                4690                4695

Thr Asp Val Glu Lys Glu Glu Lys Arg Val Phe Glu Gly Arg Thr
4700                4705                4710

Asn Gly Asp Ile Leu Val Leu Tyr Asn Leu Ser Lys His Tyr Arg
4715                4720                4725

Arg Phe Phe Gln Asn Ile Ile Ala Val Gln Asp Ile Ser Leu Gly
4730                4735                4740
```

| | | | | | | | | | | |
|---|---|---|---|---|---|---|---|---|---|---|
|Ile|Pro|Lys|Gly|Glu|Cys|Phe|Gly|Leu|Leu|Gly|Val|Asn|Gly|Ala|
| |4745| | | |4750| | | |4755| |

Ile Pro Lys Gly Glu Cys Phe Gly Leu Leu Gly Val Asn Gly Ala
    4745                4750                4755

Gly Lys Ser Thr Thr Phe Lys Met Leu Asn Gly Glu Val Ser Leu
    4760                4765                4770

Thr Ser Gly His Ala Ile Ile Arg Thr Pro Met Gly Asp Ala Val
    4775                4780                4785

Asp Leu Ser Ser Ala Gly Thr Ala Gly Val Leu Ile Gly Tyr Cys
    4790                4795                4800

Pro Gln Gln Asp Ala Leu Asp Glu Leu Leu Thr Gly Trp Glu His
    4805                4810                4815

Leu Tyr Tyr Tyr Cys Ser Leu Arg Gly Ile Pro Arg Gln Cys Ile
    4820                4825                4830

Pro Glu Val Ala Gly Asp Leu Ile Arg Arg Leu His Leu Glu Ala
    4835                4840                4845

His Ala Asp Lys Pro Val Ala Thr Tyr Ser Gly Gly Thr Lys Arg
    4850                4855                4860

Lys Leu Ser Thr Ala Leu Ala Leu Val Gly Lys Pro Asp Ile Leu
    4865                4870                4875

Leu Leu Asp Glu Pro Ser Ser Gly Met Asp Pro Cys Ser Lys Arg
    4880                4885                4890

Tyr Leu Trp Gln Thr Ile Met Lys Glu Val Arg Glu Gly Cys Ala
    4895                4900                4905

Ala Val Leu Thr Ser His Ser Met Glu Glu Cys Glu Ala Leu Cys
    4910                4915                4920

Thr Arg Leu Ala Ile Met Val Asn Gly Ser Phe Lys Cys Leu Gly
    4925                4930                4935

Ser Pro Gln His Ile Lys Asn Arg Phe Gly Asp Gly Tyr Thr Val
    4940                4945                4950

Lys Val Trp Leu Cys Lys Glu Ala Asn Gln His Cys Thr Val Ser
    4955                4960                4965

Asp His Leu Lys Leu Tyr Phe Pro Gly Ile Gln Phe Lys Gly Gln
    4970                4975                4980

His Leu Asn Leu Leu Glu Tyr His Val Pro Lys Arg Trp Gly Cys
    4985                4990                4995

Leu Ala Asp Leu Phe Lys Val Ile Glu Asn Asn Lys Thr Phe Leu
    5000                5005                5010

Asn Ile Lys His Tyr Ser Ile Asn Gln Thr Thr Leu Glu Gln Val
    5015                5020                5025

Phe Ile Asn Phe Ala Ser Glu Gln Gln Gln Thr Leu Gln Ser Thr
    5030                5035                5040

Leu Asp Pro Ser Thr Asp Ser His His Thr His Leu Pro Ile
    5045                5050                5055

<210> SEQ ID NO 26
<211> LENGTH: 17209
<212> TYPE: DNA
<213> ORGANISM: Homo sapiens

<400> SEQUENCE: 26
ggactgagag cagggagcag caggcatggg gcatgccggg tgccagttca aagccctgct      60
gtggaagaat tggctctgca gactcaggaa cccggtcctt ttccttgctg aattcttctg     120
gccttgtatc ctgtttgtaa ttctgacagt tcttcgtttt caagaacctc ccagatacag     180
agacatttgt tatttgcagc cccgagatct acccagctgt ggtgttatcc cctttgttca     240

```
aagccttctt tgtaacactg atcaaggtg taggaacttc agctatgaag ggtcaatgga      300
gcatcatttt cgtttgtcta ggttccaaac tgcagctgac cccaagaaag tcaacaacct      360
ggccttttta aaagagatac aagacctggc agaggaaatt catggaatga tggacaaggc      420
aaaaaactta aaaagacttt gggtagaacg atccaacact ccagattctt cttatggttc      480
cagttttttt acaatggatc tcaataagac cgaggaggta atattgaaac tggaaagcct      540
ccatcagcag cctcatatct gggattttct acttttactg ccgagactac acacaagcca      600
tgatcatgtg aagatggca tggatgttgc agtgaacctt ctccagacca ttttgaattc       660
cttaatatcc ctagaagatt tagattggct tccactcaac caaactttt cccaggtttc       720
tgaacttgta ctgaatgtga ccatttcgac actgacattt ctgcagcaac atggagtagc      780
agtcaccgag ccagtttacc acctgtccat gcagaatata gtgtgggatc cacagaaagt      840
ccagtatgat ctcaaatccc agtttggctt tgrtgatctt cacacggaac agatcctgaa      900
ctcttcagct gaactgaagg agattccac agacacttcc ttggagaaga tggtgtgttc       960
agtcttgtct agcacatcag aggatgaagc tgagaaatgg ggccacgttg gaggctgcca     1020
ccctaagtgg tcagaagcca aaaactatct tgtccatgca gtcagctggc tgcgagtcta     1080
ccaacaggtg tttgttcagt ggcaacaggg tagcctgctt cagaagacac tcacaggcat     1140
gggccatagt ctggaggctc tcaggaatca gtttgaagaa gagagcaagc cctggaaggt     1200
ggtggaagct ctgcacactg cactgctcct gctgaatgac agcttgtcag cagatggccc     1260
aaaagataat catacatttc caaagatatt acagcatctg tggaaattgc aaagcttgct     1320
gcaaaacctg ccccagtggc cggcactgaa gagatttctt cagcttgatg gagctctcag     1380
aaatgcgata gctcagaatt tacatttgt ccaagaagtc ctcatttgcc tggagacatc      1440
agctaatgat tttaaatggt ttgaacttaa ccaattgaaa ctggaaaagg atgtgttctt     1500
ttgggagctg aaacagatgt tggcgaagaa tgctgtctgc ccgaatggtc gtttctctga     1560
gaaggaggtc ttttgccgc ctggaaactc cagcatatgg ggtggtctcc agggactgtt      1620
gtgctattgt aactcctctg agacgagtgt tttaaacaag ctacttggtt cagtagagga     1680
tgctgatcgt attttgcaag aggtcattac ttggcacaaa aatatgtcag ttttaatacc     1740
tgaagaatat ttggactggc aggaacttga gatgcagctg tcagaagcaa gccttttcctg    1800
tactcggctc ttcctgctgc tgggagctga tccctctcct gagaatgatg tcttttctag     1860
tgactgtaag caccagcttg tctccacagt gatatttcat acacttgaaa aaacacaatt     1920
tttcctggaa caagcatatt attggaaagc cttcaaaaag tttatcagga agacttgcga     1980
agtggcccaa tatgtaaata tgcaagagag tttccagaac agactattgg cttttcctga     2040
ggaatctcct tgtttttgaag aaaacatgga ttggaaaatg atcagtgata attattttca    2100
attttttgaat aacttactca agtctccaac agcttccata tccagggctt taaatttcac    2160
aaagcacctt ctaatgatgg aaaagaagtt gcacaccctt gaggatgaac aaatgaactt     2220
tcttttatca tttgtggaat tttttgagaa attattgttg cctaatcttt ttgactcctc     2280
cattgttccc agtttccaca gcctcccatc tctcacagag gatattctga atataagttc     2340
tctgtggaca aatcatttaa aaagtttaaa gagagaccca tctgccactg atgctcagaa     2400
actcttggaa tttggcaacg aagtgatttg gaaatgcag actctcggaa gtcactggat      2460
aaggaaggaa ccaaaaaatc ttttgagatt catagaatta atacttttg aaattaatcc      2520
caaattacta gaattatggg cctatggcat ttcaaaagga aaaagagcta aattggaaaa     2580
cttctttaca cttttaaatt tttctgttcc agaaaatgag attctgagta caagttttaa     2640
```

```
cttttcccag ttgttccatt cagattggcc taaatcacca gctatgaaca tagattttgt    2700
acgtttaagt gaggctataa taactagtct ccatgaattt ggattttgg agcaggaaca     2760 gatctcagaa gctctgaaca cagtctacgc tatcaggaat gcatctgatc ttttctcagc    2820
cctttctgaa ccacaaaaac aagaagttga taaaattttg actcacatac acctaaatgt    2880
cttccaggac aaggattcag ctttacttct gcaaatttat tcttcatttt accgatatat    2940
ttatgaatta ttgaatattc agagtagagg ctcttcgttg actttcctta cacaaatctc    3000
aaaacacatt ttggatatca taaaacaatt taatttccaa aacatcagta aagcatttgc    3060
atttttattt aagacagcag aggttcttgg gggaatttct aatgtatctt actgtcagca    3120
attgctttca attttaact ttttggagct tcaggcccaa tccttcatgt ctacagaggg     3180
ccaagaactg gaagtgatcc acactacttt gacaggcctc aaacagctgc tcataattga    3240
tgaagatttt cgtatttctt tatttcaata tatgagccaa ttcttcaaca gttcagtaga    3300
agacctattg gataataaat gcttgattttc ggacaataaa cacatttctt ccgtaaatta   3360
ttcaacaagt gaggagtctt catttgtttt tccattggca caattttttt caaacctctc    3420
agcaaatgtc agtgtgttca acaagtttat gtccattcac tgtaccgttt catggcttca    3480
aatgtggact gaaatctggg aaaccatatc tcaattattt aagtttgaca tgaatgtttt    3540
cacatctctt catcatggtt tcactcagct tttggatgaa ttggaagatg atgtgaaagt    3600
ctctaaaagc tgccagggta tacttcccac ccataatgtt gctagactca tattaaattt    3660
gtttaaaaat gtaactcaag ccaatgactt ccataattgg gaggacttcc tggatctcag    3720
ggattttttg gtagctttag gtaatgcatt agtttcagta aaaaaactta acttggagca    3780
agtggagaaa tcccttttca ccatggaagc tgccctgcat cagttgaaga catttccatt    3840
caacgaaagt acaagcagag agtttttaaa ttctctgctt gaagttttca ttgagtttag    3900
cagtacctca gaatatatag tcagaaatct agattcaata aatgactttc tttcaaataa    3960
tctcacaaat tatggagaaa aatttgaaaa tatcatcact gagctaagag aagcaatagt    4020
atttcttaga aatgtatcac atgatcgaga tttgttttcc tgtgctgata ttttccaaaa    4080
tgttactgag tgtattttag aagatggctt tttatatgta aatacctcac agaggatgtt    4140
acgtattcta gacacgttaa attccacatt ttcctctgag aacacaatta gcagtctgaa    4200
aggatgcatt gtatggttag atgtcataaa ccatttgtat ttgttgtcta actccagttt    4260
ttcacaaggt cgtcttcaaa atattttggg gaatttcaga gatatagaaa acaaaatgaa    4320
ctctatatta aaaattgtaa cttgggtgtt aaatataaaa aaacctcttt gttcatcaaa    4380
tggctcacat ataaattgtg tcaatattta cttgaaagat gtaactgact ttctaaatat    4440
tgtacttact acagtctttg aaaagagaa gaaacctaaa tttgagattt tattagctct    4500
tttaaatgat tccacaaagc aagtaaggat gagtatcaac aacttaacaa cagactttga    4560
ttttgcatct cagtccaatt ggagatattt tactgaatta attctaagac caatagaaat    4620
gtcagatgaa attcctaatc agtttcaaaa tatttggctt catttaataa cactggggaa    4680
ggaatttcag aagcttgtaa aaggtatttta ttttaacatc ctggaaaata attcctcttc    4740
taaaactgaa aacttgttaa acatatttgc caccagtcca aaagaaaagg atgtaaacag    4800
tgtaggcaat tccatttatc acttagctag ttaccttgcc ttcagcttat ctcatgacct    4860
ccaaaattca ccaaaaataa taatttcacc tgaaataatg aaagctacag gtcttggtat    4920
tcaactgata agggatgtgt tcaactcctt aatgcctgta gttcatcaca ctagtccaca    4980
```

```
aaatgcaggt tatatgcaag cttttgaagaa ggtaacttct gtcatgcgta cccttaagaa    5040
agcagacata gaccttttag tggatcagct tgaacaagtt agtgtaaacc taatggattt    5100
ctttaagaat atcagtagtg tgggaactgg caatttagtg gtcaatttgc ttgttggctt    5160
gatggaaaaa tttgcagaca gctcacattc ttggaatgtt aatcatctgc tgcagctctc    5220
acgcctgttt cctaaagatg ttgtggatgc tgtgatagat gtgtactatg tgcttcctca    5280
tgctgtaagg ctcctgcagg gagtacctgg taaaaacatc actgaaggcc tcaaggatgt    5340
ctacagcttc acactccttc atggcataac catttcaaat atcaccaagg aagacttcgc    5400
aattgtgata aaaattcttt tggatacaat tgaattagta tcagataagc cagatatatt    5460
ttcagaggct ttagcttgtt ttcctgtggt ttggtgctgg aatcacacaa attctggatt    5520
tcggcagaat tcaaagatag accccctgcaa tgtccatggg ctcatgtctt cttcctttta    5580
tggcaaagtg gccagtatac ttgatcattt ccacctgtct ccccaaggtg aagattcacc    5640
atgttcaaat gaaagctccc gaatggaaat aactaggaaa gtggtctgca taattcatga    5700
attagtggac tggaattcta ttcttctgga gctctctgaa gtcttccatg ttaacatttc    5760
tcttgtgaaa actgtgcaga aattttggca taagatatta ccgtttgtcc caccttcaat    5820
aaatcaaact agggatagca tctctgaact ctgtcctagt ggttccataa agcaagttgc    5880
tttgcaaatc atagaaaaac ttaaaaatgt caactttaca aaagttacat caggtgaaaa    5940
tattcttgac aaactaagta gtttaaacaa gatccttaac attaatgaag acacagagac    6000
atctgttcaa aatattattt cctcaaattt ggaaaggaca gtacaattga tttctgaaga    6060
ctggagccta gaaaaagta cgcataatct actctcttta ttcatgatgc tccagaatgc    6120
aaatgtcaca ggtagcagtt tagaagcatt atcaagtttt attgaaaaaa gtgaaacacc    6180
ttacaacttt gaagaactat ggcccaagtt tcaacaaatc atgaaagacc taacccaaga    6240
ttttagaatc agacacctgc tttctgaaat gaacaaagga atcaaaagta taaattcaat    6300
ggctcttcaa aagataactt tgcagttttgc ccatttcctg gaaatcctgg attcaccgtc    6360
attgaagaca ttagaaatta ttgaagattt tctattggtc acaaaaaact ggcttcagga    6420
atatgcaaat gaggattact ccagaatgat agaaacatta ttcattcctg tgaccaatga    6480
gagttcaact gaagatatag ctttgttagc caaagctatt gctacttttt ggggctcttt    6540
aaaaaatata tctagagcag gcaattttga tgttgccttt cttacccatc tgctaaatca    6600
agaacagctg actaatttct cagttgttca gctgcttttt gaaaacatcc taattaattt    6660
gatcaataac ttagctggga attctcagga agcagcttgg aacttaaatg atactgacct    6720
tcaaataatg aatttcatta accttatctt gaaccatatg cagtcagaaa ctagtaggaa    6780
aacagttctc tctctgagaa gcatagtaga tttcacagaa cagtttttga aaacattctt    6840 ctccctttt ctaaaggaag attctgagaa caaaatatct cttctgctga atatttcca    6900 caaagatgtt attgcagaga tgagttttgt cccaaaagat aaaattctag aaattctgaa    6960
actggatcaa tttcttaccc tgatgataca agacagattg atgaacattt ttcaagtttt    7020
aaaggagact atatatcacc taatgaaaag ttcatttata ttagacaatg gagaattta    7080 ttttgatact catcaaggac tgaagttcat gcaagattta tttaatgccc ttctcaggga    7140
aacttcaatg aaaaataaga ctgaaaataa tatagacttt ttcacagtgg tgagtcagtt    7200 gttttttccat gtgaataagt ctgaggacct cttcaaactc aatcaagatc ttgggtcagc    7260
tcttcacctt gtaagagaat gttcaacaga gatggcaaga cttctggata caattttaca    7320
ctctcctaat aaggacttct atgctttgta tcctacccc aagaagttta tacttgctaa    7380
```

```
tctaacggat tgcttttct ttataaataa ttcattccct ctaagaaaca gagcaacatt    7440
agaaattact aagagattag ttggtgctat ttcaagagca agtgaagaaa gtcacgtcct    7500 gaaaccctc ttagaaatgt ctgggactct ggtcatgctg ttgaatgaca gtgctgacct     7560
gagagatctt gccacatcaa tggactccat tgtgaaactt cttaagctgg tcaagaaagt    7620
ttcggggaag atgtccacag ttttaaaac tcattttatc tccaatacca aggacagtgt     7680
gaaattcttt gacactctgt attccatcat gcaacaaagt gttcaaaatc ttgtgaaaga    7740
aatagctact ttaaaaaaaa tagatcattt cacatttgaa aagataaatg atttgttggt    7800
gccatttctt gacttggcct ttgaaatgat tggggtagaa ccttatatat catcaaactc    7860
tgatattttc agtatgtcac ctagcatact ctcatatatg aaccaatcta aggactttc     7920 tgatattttg gaagaaattg ctgaatttt aacatctgtg aaaatgaact tggaagatat     7980
gaggagtctt gcggtagcat ttaacaatga gactcaaaca ttttctatgg attctgtcaa    8040
cttaygggaa gaaattctgg gttgcttagt tcctataaat aacatcacca accaaatgga    8100
cttcttatac cctaatccaa tttccactca tagtggccct caagatataa aatgggaaat    8160
aattcatgaa gtgatccttt ttttggataa aatattatca caaaacagca cagaaatagg    8220
atctttcttg aaaatggtga tctgtctcac cttagaagct cttttggaaaa acttaaagaa    8280 agataattgg aatgtttcta atgtgttgat gacgttact cagcatccaa ataaccttt      8340 gaaaaccata gaaacagttt tagaggcctc cagtggaatt aaaagtgact atgaaggtga    8400
tttgaataaa agtttatatt ttgacacacc tttgagtcag aatataactc atcatcaact    8460
tgaaaaagca atccataatg ttttaagtag aatagctctc tggaggaaag gacttcgttt    8520
taacaactct gaatggataa cttccacaag aactttgttt cagccacttt ttgagatttt    8580
cattaaagca accaccggaa agaatgtcac atcagaaaaa gaagagagaa ccgagaaaga    8640
gatgattgac tttccttata gtttcaaacc attttttctgt ttggagaaat acctgggagg    8700
attatttgta ttgactaaat actggcaaca aatcccacta acagatcaaa gtgttgttga    8760
gatttgtgaa gttttccagc agactgtgaa gccctcagaa gccatggaga tgctgcagaa    8820
agtgaagatg atggtcgtac gtgtgctcac catcgttgca gaaaacccctt cctggaccaa    8880 ggacattttg tgtgctactc tgagttgcaa gcaaaatggg ataaggcatc tcattttatc    8940
tgctatacaa ggggtcactt tggcgcagga ccacttccag gaaattgaaa agatatggtc    9000
ctcgccgaat cagctaaatt gtgaaagtct tagcaagaat ctttctagca ccttggagag    9060
cttcaagagc agcttggaaa atgccactgg ccaggactgc acaagccagc cgaggctgga    9120
gacggtgcag cagcacttgt acatgttggc caaaagcctc gaggaaactt ggtcatcagg    9180
gaatcccatc atgacttttc tcagcaattt cacagtaact gaggatgtaa aaataaaaga    9240
tttgatgaag aatatcacca agttgactga ggagcttcgc tcttccatcc aaatctcgaa    9300
tgagactatc catagcattc tagaagcaaa tatttcccac tccaaggttc tcttcagtgc    9360
cctcaccgta gctctgtctg aaagtgtgga tcaggaaatc cttcatctcc tgctgacatt    9420
tcccaaaggg gaaaaatctt ggatcgcagc ggaggaactc tgtagcctgc cagggtcaaa    9480
agtgtattct ctgattgtgt tgctgagtcg aaacttggat gtgcgagctt tcatttacaa    9540
gactctgatg ccttctgaag caaatggctt gctcaactcc ttgctggata tagtttccag    9600
cctcagcgcc ttgcttgcca aagcccagca cgtctttgag tatcttcctg agtttcttca    9660
cacatttaaa atcactgcct tgctagaaac cctggacttt caacaggttt cacaaaatgt    9720
```

```
ccaggccaga agttcagctt ttggttcttt ccagtttgtg atgaagatgg tttgcaagga    9780
ccaagcatca ttccttagcg attctaatat gtttattaat ttgcccagag ttaaggaact    9840
cttggaagat gacaaagaaa aattcaacat tcctgaagat tcaacaccgt tttgcttgaa    9900
gctttatcag gaaattctac aattgccaaa tggtgctttg gtgtggacct tcctaaaacc    9960
catattgcat ggaaaaatac tatacacacc aaacactcca gaaattaaca aggtcattca   10020
aaaggctaat tacacctttt atattgtgga caaactaaaa actttatcag aaacactgct   10080
ggaaatgtcc agccttttcc agagaagtgg aagtggccag atgttcaacc agctgcagga   10140
ggccctgaga acaaatttg taagaaactt tgtagaaaac cagttgcaca ttgatgtaga    10200
caaacttact gaaaaactcc agacatacgg agggctgctg gatgagatgt ttaaccatgc   10260
aggcgctgga cgcttccgtt tcttgggcag catcttggtc aatctctctt cctgcgtggc   10320
actgaaccgt ttccaggctc tgcagtctgt cgacatcctg gagactaaag cacatgaact   10380
cttgcagcag aacagcttct tggccagtat cattttcagc aattccttat tcgacaagaa   10440
cttcagatca gagtctgtca aactgccacc ccatgtctca tacacaatcc ggaccaatgt   10500
gttatacagc gtgcgaacag atgtggtaaa aaacccttct tggaagttcc accctcagaa   10560
tctaccagct gatgggttca atataacta cgtctttgcc ccactgcaag acatgatcga    10620
aagagccatc attttggtgc agactgggca ggaagccctg gaaccagcag cacagactca   10680
ggcggcccct tacccctgcc ataccagcga cctattcctg aacaacgttg gtttcttttt   10740
tccactgata atgatgctga cgtggatggt gtctgtggcc agcatggtca gaaagttggt   10800
gtatgagcag gagatacaga tagaagagta tatgcggatg atgggagtgc atccagtgat   10860
ccatttcctg gcctggttcc tggagaacat ggctgtgttg accataagca gtgctactct   10920
ggccatcgtt ctgaaaacaa gtggcatctt tgcacacagc aataccttta ttgttttcct   10980
cttttctcttg gatttttggga tgtcagtcgt catgctgagc tacctcttga gtgcattttt   11040
cagccaagct aatacagcgg ccctttgtac cagcctggtg tacatgatca gctttctgcc   11100
ctacatagtt ctattggttc tacataacca attaagtttt gttaatcaga catttctgtg   11160
ccttctttcg acaaccgcct ttggacaagg ggtattttt attacattcc tggaaggaca   11220
agagacaggg attcaatgga ataatatgta ccaggctctg gaacaagggg gcatgacatt   11280
tggctgggtt tgctgatga ttcttttttga ttcaagcctt tattttttgt gtggatggta    11340
cttgagcaac ttgattcctg aacatttggg tttacggaaa ccatggtatt tccccttta     11400
tgcctcatat tggaagagtg tgggtttctt ggtggagaaa aggcaatact ttctaagttc   11460
tagtctgttc ttcttcaatg agaactttga caataaaggg tcatcactgc aaaacaggga   11520
aggagagctt gaaggaagtg cccccgggagt caccctggtg tctgtgacca aggaatatga   11580
gggccacaag gctgtggtcc aagacctcag cctgaccttc tacagagacc aaatcaccgc   11640
cctgctgggg acaaacggtg ccgggaaaac cactatcata tccatgttga cggggctcca   11700
ccctcccact tctggaacca tcatcatcaa tggcaagaac ctacagacag acctgtcgag   11760
ggtcagaatg gagcttggtg tgtgtccgca gcaggacatc ctgttggaca acctcaccgt   11820
ccgggaacat ttgctgctct ttgcttccat aaaggcgcct cagtgaccaa agaaggagct   11880
gcatcagcaa gtcaatcaaa ctcttcagga tgtggactta actcagcatc agcacaaaca   11940
gacccgagct ctgtctggag gcctgaagag gaagctctcc cttggcattg ctttcatggg   12000
catgtcgagc accgtggttc tggatgagcc caccagtggg gtggaccctt gctcccggca   12060
tagcctgtgg gacattctgc tcaagtaccg agaaggtcgt acgatcatct tcacaaccca   12120
```

```
ccacctggat gaagccgaag cgctgagtga ccgcgtggcc gtcctccagc atgggaggct   12180
caggtgctgc ggtcctccct tctgcctgaa ggaggcatat ggccagggc tccgcctgac    12240 actcacgagg cagccttctg ttctggaggc ccatgatctg aaagacatgg cttgtgttac   12300
atccctgata aagatctata ttccacaagc atttctcaaa gacagcagtg gaagtgagct   12360
gacctacacc attccaaagg acacagacaa ggcctgcttg aaagggctct tccaggccct   12420
ggatgagaac ctgcatcagc tgcacctgac gggctatggg atctcagaca ccaccttaga   12480
agaggtgttt ttgatgcttt tgcaagattc caacaagaaa tctcacattg ccctggggac   12540
tgagtcagag ctgcagaacc acaggcctac aggacatctg tctggctact gtggctccct   12600
agcacggccc gcaactgtgc agggcgtcca gctgctccgc gcacaagtgg ccgcgatcct   12660
ggcccggagg ctccgccgca cgctgcgcgc cgggaagagc accctcgccg acctgctgct   12720
gccagtcctc ttcgtggcct tggccatggg cttgttcatg gtgagacccc tggccaccga   12780
gtaccctccc ctcagactca cacctggaca ttaccagcgg gccgagacct actttttcag   12840 cagtggggc gacaacttgg acctcacccg tgtgcttctg cggaagttta gagatcaaga    12900
tttgccctgt gcagatttaa acccacgcca gaagaattct tcatgctggc gcacagatcc   12960 ctttctcac ccagaattcc aggattcatg tggctgcctg aagtgtccaa atagaagtgc    13020
tagtgctccc tacctgacca accacctggg ccacacactg ttgaatctct caggcttcaa   13080
tatggaggag tacttgctgg caccatctga aaaaccaagg cttggaggtt ggtcttttgg   13140
attaaaaatc cccagtgaag ctggaggtgc aaatggaaac atatcaaaac ccccaactct   13200
ggcaaaggtg tggtataatc agaagggttt tcattcccta ccttcctact aaatcatct    13260 aaacaacctt attttgtggc agcacctacc ccctactgtg gactgagac aatacggaat    13320 aacactctac agccacccat atggagggc cttgctgaac gaggacaaga tcctggagag    13380
catccgtcag tgtggagtgg ccctctgcat cgtgctggga ttctccatcc tgtctgcatc   13440
catcggcagc tctgtggtga gggacagggt gattggagcc aaaaggttgc agcacataag   13500
tggccttggc tacaggatgt actggttcac aaacttccta tatgacatgc tcttttactt   13560
ggtttccgtc tgcctgtgtg ttgccgttat tgtcgccttc cagttaacag cttttacttt   13620
ccgcaagaac ttggcagcca cggccctcct gctgtcactt ttcggatatg caactcttcc   13680
atggatgtac ctgatgtcca gaatcttttc cagttcggac gtggctttca tttcctatgt   13740
ctcactaaac ttcatctttg cctttgtac catgcccata accattatgc cccggttgct   13800
agccatcatc tccaaagcta agaatttaca gaatatctat gatgtcctca gtgggtctt    13860 tactattttt cctcaattct gtcttggtca aggactggta gaactctgct ataatcagat   13920
caaatatgac ctgacccaca acttcggcat tgattcctat gtgagtccct ttgagatgaa   13980
ctttctgggc tggatcttcg tgcaactggc ctcgcagggc acagtacttc tcctcttgag   14040
ggttctgcta cactgggacc ttctgcgatg gccaagggt cattctactc tccaaggcac    14100
agtcaaatct tctaaggata cagatgttga aaagaggaa aagagagtgt tgaaggaag    14160 gaccaatgga gacattcttg tgttatacaa ccttagtaaa cattatcgac gcttttcca    14220 gaatattatt gctgtgcaag atattagttt ggcatacca aaaggagagt gctttggact    14280
tctaggggtg aatggagctg ggaagagcac gactttcaaa atgctgaatg gtgaagtttc   14340
tctaacttca ggacatgcta tcatcaggac tcccatggga gacgccgtgg acctgtcttc   14400
tgctggcacg gcaggcgtgc tcattggcta ctgtccccag caggatgccc tggacagagct  14460
```

```
tctgactggt tgggaacatc tctattatta ctgtagctta cgcgggattc caaggcagtg   14520
catccctgag gttgctggag acctcatcag gcgcttacac ctcgaagccc acgcggacaa   14580
acctgtggcc acctacagtg ggggaaccaa gcggaaactc tctacagccc tggccctggt   14640
ggggaaacct gacattcttt tattggatga gcccagctct gggatggatc cctgctctaa   14700
gcggtacctg tggcaaacaa taatgaagga ggttcgggaa ggctgtgctg cggtgctgac   14760
ctcccacagc atggaggagt gtgaggctct ttgcacaaga ctggccataa tggttaacgg   14820
cagcttcaaa tgtcttggtt ctcctcagca catcaaaaat aggtttggtg atggttatac   14880
agtcaaagtt tggctctgta aggaagcaaa tcaacattgc actgtttctg accacttgaa   14940
gctttatttt ccaggaattc agttcaaggg acagcacctg aatttattag aatatcatgt   15000
gccaaaaaga tggggatgcc tagctgactt gttcaaagtt atagagaaca ataaaacctt   15060
cttgaatatt aagcattatt ccattaacca aaccactttg gagcaggtat ttattaattt   15120
tgcttctgag cagcagcaaa ctctacaatc tactcttgat ccatccactg acagtcacca   15180
cacacatcac ttgcccatct gagcactaaa gaagtttcca taaggaataa aaccttgtct   15240
tccattacaa ttaacagtca aggataaaac aagcacgcgc acaatcaagg agctggaaca   15300
cactctccag gccgtcaaat tattctcttg ttcattttct attttgaatc tccttgttag   15360
ttaataacca ccaaatggaa aggtcattct ttctgcagac ttttggggag ctcctccaaa   15420
acatttgttc tctttaccat gccagatgga caccagcttc tttgtgacaa aggcatgaat   15480
gatttgacag tgtccaaact gagacattct ggagctggaa agcctgtcac actagagtgt   15540
gtgtgacatg tccactctaa acatgtcact tttctgttaa gaaaactgag cccctcccc   15600 acaggttaaa aaactttagt aacttgtttg tatagaaaat agtaacaagg actattttct   15660
attgttgtca tctatttact agatacatgt ttttaatgat tttaatgtaa gcttttatta   15720
atactgatga cattatatgg tatgatatga aaaaatcacc aatttttac atataaaaga   15780 tacctttta aaaaaatagg ttttaagagc tcttttagta tacactttag caaaattaat   15840
taaattgaac tagttactct gtatcaatta cagtagttct accagaatct cccaggttat   15900
aatttatgag ggtagagaaa taaaatgtag atgcattttc tttttcttca tttggatgaa   15960
taattactgt ttttttgttat tctaagtcag tgttttttcaa agcgtagtgg tccccatatt   16020
agctgcattg ccatcttctg ggagcttgca agaaatgtac attctcagga tccactccag   16080
acctattgaa tctcaaattc tggggcttaa acaagcacat tccaagttaa gaaccaatga   16140
cctaagggaa tgtctggtta cctcctagtt atacaagcaa atctgcata gtatgtagtc   16200 tttttttattt atttattttt ttttttgag gcggagtctc gctctgtcac ccaggctgga   16260
gtgcagtggc gcgatgtcgg ctcactgcaa gctccgcctc ctgggttcac gccattctcc   16320
tgcctcagcc tccccagcag ctgggactac aggcacacat cgccacaccc ggctaatttt   16380 tagtatttt agtagagacg gggtttcacc gtgttagcca ggatggtctc tatctcctga   16440
ccttgtgatc cgccccctc cacctcccaa agtgctggga ttacaggcgt gagccaccgt   16500
gtccggccgt agtttatttt aaaatatatt tttaaaagct ttgtaaaaat tatgtcattc   16560
tcagaattgt tgtcttcaaa gcattgtcag atgtagagtg ctcagatgtg gctcttaaag   16620
actatataca tctgaatttt tcatcctata gttagtaaga tgcataaaat caatccacta   16680
ctgaaatagt ttccagtcag acatttctga gttcagacat ttctcaacat tcttttaaca   16740 acattttct gaatcctcaa tagaaaatca cattaatctt attttaaaat ttggccttt   16800 tcaacactaa cgttgagtac cggtagcttt gtgatcaaag gcatatactt ccttatgaga   16860
```

-continued

```
tttctttact aaagcaagat ttcattaaat ctctatttcc taaatatcat tctatacaaa    16920
agatattttt taaacggtaa ggattaagac aatcactgat agctttgttg tgagcaattt    16980
tgattcccat gtatcacatg aattacactt ccttaaataa attacagttt atggctgtat    17040
gatttattct ctaattctaa catagtctag ttgtcaaaag gaaatatgta atctttttat    17100
gattgttgaa tcaataaata ccaatttgtg aaacatgaat gtgtttaaac tgcagtgaat    17160
aaatgagatg tgctttaatt taacccaaaa aaaaaaaaaa aaaaaaaa                 17209
```

<210> SEQ ID NO 27
<211> LENGTH: 931
<212> TYPE: PRT
<213> ORGANISM: Homo sapiens

<400> SEQUENCE: 27

Met Lys Ile Gln Lys Lys Leu Thr Gly Cys Ser Arg Leu Met Leu Leu
1               5                   10                  15

Cys Leu Ser Leu Glu Leu Leu Glu Ala Gly Ala Gly Asn Ile His
        20                  25                  30

Tyr Ser Val Pro Glu Glu Thr Asp Lys Gly Ser Phe Val Gly Asn Ile
        35                  40                  45

Ala Lys Asp Leu Gly Leu Gln Pro Gln Glu Leu Ala Asp Gly Gly Val
    50                  55                  60

Arg Ile Val Ser Arg Gly Arg Met Pro Leu Phe Ala Leu Asn Pro Arg
65                  70                  75                  80

Ser Gly Ser Leu Ile Thr Ala Arg Arg Ile Asp Arg Glu Glu Leu Cys
                85                  90                  95

Ala Gln Ser Met Pro Cys Leu Val Ser Phe Asn Ile Leu Val Glu Asp
            100                 105                 110

Lys Met Lys Leu Phe Pro Val Glu Val Glu Ile Ile Asp Ile Asn Asp
        115                 120                 125

Asn Thr Pro Gln Phe Gln Leu Glu Glu Leu Glu Phe Lys Met Asn Glu
    130                 135                 140

Ile Thr Thr Pro Gly Thr Arg Val Ser Leu Pro Phe Gly Gln Asp Leu
145                 150                 155                 160

Asp Val Gly Met Asn Ser Leu Gln Ser Tyr Gln Leu Ser Ser Asn Pro
                165                 170                 175

His Phe Ser Leu Asp Val Gln Gln Gly Ala Asp Gly Pro Gln His Pro
            180                 185                 190

Glu Met Val Leu Gln Ser Pro Leu Asp Arg Glu Glu Ala Val His
        195                 200                 205

His Leu Ile Leu Thr Ala Ser Asp Gly Gly Glu Pro Val Arg Ser Gly
    210                 215                 220

Thr Leu Arg Ile Tyr Ile Gln Val Val Asp Ala Asn Asp Asn Pro Pro
225                 230                 235                 240

Ala Phe Thr Gln Ala Gln Tyr His Ile Asn Val Pro Glu Asn Val Pro
                245                 250                 255

Leu Gly Thr Gln Leu Leu Met Val Asn Ala Thr Asp Pro Asp Glu Gly
            260                 265                 270

Ala Asn Gly Glu Val Thr Tyr Ser Phe His Asn Val Asp His Arg Val
        275                 280                 285

Ala Gln Ile Phe Arg Leu Asp Ser Tyr Thr Gly Glu Ile Ser Asn Lys
    290                 295                 300

Glu Pro Leu Asp Phe Glu Glu Tyr Lys Met Tyr Ser Met Glu Val Gln

-continued

| | | | 305 | | | | 310 | | | | 315 | | | | 320 |

Ala Gln Asp Gly Ala Gly Leu Met Ala Lys Val Lys Val Leu Ile Lys
                    325                 330                 335

Val Leu Asp Val Asn Asp Asn Ala Pro Glu Val Thr Ile Thr Ser Val
                    340                 345                 350

Thr Thr Ala Val Pro Glu Asn Phe Pro Pro Gly Thr Ile Ile Ala Leu
                    355                 360                 365

Ile Ser Val His Asp Gln Asp Ser Gly Asp Asn Gly Tyr Thr Thr Cys
        370                 375                 380

Phe Ile Pro Gly Asn Leu Pro Phe Lys Leu Glu Lys Leu Val Asp Asn
385                 390                 395                 400

Tyr Tyr Arg Leu Val Thr Glu Arg Thr Leu Asp Arg Glu Leu Ile Ser
                405                 410                 415

Gly Tyr Asn Ile Thr Ile Thr Ala Ile Asp Gln Gly Thr Pro Ala Leu
                420                 425                 430

Ser Thr Glu Thr His Ile Ser Leu Leu Val Thr Asp Ile Asn Asp Asn
            435                 440                 445

Ser Pro Val Phe His Gln Asp Ser Tyr Ser Ala Tyr Ile Pro Glu Asn
        450                 455                 460

Asn Pro Arg Gly Ala Ser Ile Phe Ser Val Arg Ala His Asp Leu Asp
465                 470                 475                 480

Ser Asn Glu Asn Ala Gln Ile Thr Tyr Ser Leu Ile Glu Asp Thr Ile
                485                 490                 495

Gln Gly Ala Pro Leu Ser Ala Tyr Leu Ser Ile Asn Ser Asp Thr Gly
            500                 505                 510

Val Leu Tyr Ala Leu Arg Ser Phe Asp Tyr Glu Gln Phe Arg Asp Met
            515                 520                 525

Gln Leu Lys Val Met Ala Arg Asp Ser Gly Asp Pro Pro Leu Ser Ser
            530                 535                 540

Asn Val Ser Leu Ser Leu Phe Leu Leu Asp Gln Asn Asp Asn Ala Pro
545                 550                 555                 560

Glu Ile Leu Tyr Pro Ala Leu Pro Thr Asp Gly Ser Thr Gly Val Glu
                565                 570                 575

Leu Ala Pro Leu Ser Ala Glu Pro Gly Tyr Leu Val Thr Lys Val Val
                580                 585                 590

Ala Val Asp Arg Asp Ser Gly Gln Asn Ala Trp Leu Ser Tyr Arg Leu
            595                 600                 605

Leu Lys Ala Ser Glu Pro Gly Leu Phe Ser Val Gly Leu His Thr Gly
        610                 615                 620

Glu Val Arg Thr Ala Arg Ala Leu Leu Asp Arg Asp Ala Leu Lys Gln
625                 630                 635                 640

Ser Leu Val Val Ala Val Gln Asp His Gly Gln Pro Pro Leu Ser Ala
                645                 650                 655

Thr Val Thr Leu Thr Val Ala Val Ala Asp Arg Ile Ser Asp Ile Leu
                660                 665                 670

Ala Asp Leu Gly Ser Leu Glu Pro Ser Ala Lys Pro Asn Asp Ser Asp
            675                 680                 685

Leu Thr Leu Tyr Leu Val Val Ala Ala Ala Val Ser Cys Val Phe
            690                 695                 700

Leu Ala Phe Val Ile Val Leu Leu Ala His Arg Leu Arg Arg Trp His
705                 710                 715                 720

Lys Ser Arg Leu Leu Gln Ala Ser Gly Gly Gly Leu Ala Ser Met Pro
                725                 730                 735

```
Gly Ser His Phe Val Gly Val Asp Gly Val Arg Ala Phe Leu Gln Thr
            740                 745                 750

Tyr Ser His Glu Val Ser Leu Thr Ala Asp Ser Arg Lys Ser His Leu
            755                 760                 765

Ile Phe Pro Gln Pro Asn Tyr Ala Asp Thr Leu Ile Ser Gln Glu Ser
            770                 775                 780

Cys Glu Lys Lys Gly Phe Leu Ser Ala Pro Gln Ser Leu Leu Glu Asp
785                 790                 795                 800

Lys Lys Glu Pro Phe Ser Gln Gln Ala Pro Pro Asn Thr Asp Trp Arg
                805                 810                 815

Phe Ser Gln Ala Gln Arg Pro Gly Thr Ser Gly Ser Gln Asn Gly Asp
                820                 825                 830

Asp Thr Gly Thr Trp Pro Asn Asn Gln Phe Asp Thr Glu Met Leu Gln
            835                 840                 845

Ala Met Ile Leu Ala Ser Ala Ser Glu Ala Ala Asp Gly Ser Ser Thr
850                 855                 860

Leu Gly Gly Gly Ala Gly Thr Met Gly Leu Ser Ala Arg Tyr Gly Pro
865                 870                 875                 880

Gln Phe Thr Leu Gln His Val Pro Asp Tyr Arg Gln Asn Val Tyr Ile
                885                 890                 895

Pro Gly Ser Asn Ala Thr Leu Thr Asn Ala Ala Gly Lys Arg Asp Gly
                900                 905                 910

Lys Ala Pro Ala Gly Gly Asn Gly Asn Lys Lys Ser Gly Lys Lys
            915                 920                 925

Glu Lys Lys
    930

<210> SEQ ID NO 28
<211> LENGTH: 4602
<212> TYPE: DNA
<213> ORGANISM: Homo sapiens

<400> SEQUENCE: 28
atgaagattc agaaaaagct gactggctgc agcaggctga tgcttctgtg tctttctctg      60
gagctgctgt tggaagctgg ggctgggaat attcactact cagtgccgga agagacagac     120
aaaggttcct tcgtaggcaa catcgccaag gacctagggc tgcaaccccca ggagctggca     180 gatggcggag tccgcatcgt ctccagaggt aggatgccgc ttttcgctct gaatcctaga     240
agtggcagct tgatcaccgc gcgcaggata gaccgggagg agctctgcgc tcagagcatg     300
ccgtgtctcg tgagttttaa tatccttgtt gaggataaaa tgaagctttt tcctgttgaa     360
gtagaaataa ttgatattaa tgacaacact ccccaattcc agttagagga actggagttt     420
aaaatgaatg aaataacgac tccaggtacc agagtctcat tgccttttgg caagaccctt     480
gatgtgggta tgaactcact ccagagctac caactcagct ctaaccctca tttctccctg     540
gatgtgcaac agggagccga tgggcctcaa catccagaga tggtgctgca gagtcccttt     600
gacagagaag aagaagctgt ccaccacctc atcctcacag cttctgatgg gggtgaaccca     660 gtccgttcag ggaccctcag aatttacatt caggtggtgg atgcaaatga caatcctcca     720
gcatttactc aggcacaata ccatataaat gtccccgaaa acgtgccgct gggtactcag     780
ctgctcatgg taaatgccac tgaccctgat gagggagcca atgggaagt aacgtactcc     840 tttcacaatg tagaccacag agtggcccaa atatttcgtt tagattctta cacaggagaa     900
atatcaaata agaaccact agatttcgaa gaatacaaaa tgtattcaat ggaagttcaa     960
```

-continued

```
gcccaggatg gtgcggggct catggctaaa gttaaggtac tgatcaaagt tttggatgta    1020
aatgataatg ccccagaagt gaccatcacc tctgtcacca ctgcagttcc agaaaacttt    1080
cctcctggga ccataattgc tcttatcagt gtgcatgacc aggactcagg agacaatggc    1140
tacaccacat gtttcattcc tggaaattta ccctttaaat tggaaaagtt agttgataat    1200
tattaccgtt tagtgactga agaacactg acagagaac ttatctctgg gtacaacatc      1260
acaataacag caatagacca aggaactcca gctctatcta ctgaaactca catttcacta    1320
ctagtgacag atatcaatga caactcccca gtcttccatc aggactccta ctctgcctac    1380
attcccgaaa caaccccag aggagcctcc atcttctctg tgagggccca cgacttggac      1440
agcaatgaga atgcacaaat cacttactcc ctaatagagg acactatcca gggggcaccc    1500
ctatctgcct acctctccat caactccgac actggggtcc tgtatgcgct gcgatccttc    1560
gactatgagc agttccggga catgcaactg aaagtgatgg cgcgggacag tggggatccg    1620
cccctcagca gcaacgtgtc tctcagccta ttcctgctgg accagaacga caacgcgccc    1680
gagatcctgt accccgccct ccccacagat ggttctaccg gcgtggagct ggcgcccctc    1740
tccgcagagc ccggctacct ggtgaccaag gtggtggcgg tggacagaga ctcgggccag    1800
aacgcctggc tgtcctaccg cctgctcaag gccagcgagc cgggactctt ctcggtgggt    1860
ctgcacacgg gcgaggtgcg cacggcgcga gccctgctgg acagagacgc gctcaagcag    1920
agtctcgtgg tggccgtcca ggaccacggc cagcccccgc tctccgccac tgtcacgctc    1980
accgtggccg tggccgacag gatcctccgac atcctggccg acctgggcag cctcgagccc    2040
tccgccaaac ccaacgattc ggacctcact ctgtacctgg tggtggcggc ggccgcggtc    2100
tcctgcgtct tcctggcctt cgtcatcgtg ctgctggcgc acaggctgcg gcgctggcac    2160
aagtcacgtc tgctacaggc ttcgggaggc ggcttagcga gcatgcccgg ttcgcacttt    2220
gtgggcgtgg acggggttcg ggcttttcctg cagacctatt cccacgaggt ctccctcact    2280
gcggactcgc ggaagagcca cctgatttc ccccagccca actatgcgga cacactcatc      2340
agccaggaga gctgtgagaa aaagggtttt ctatcagcac cccagtcttt acttgaagac    2400
aaaaaggaac cattttctca gcaagccccg cccaacacgg actggcgttt ctctcaggcc    2460
cagagacccg gcaccagcgg ctcccaaaat ggcgatgaca ccggcacctg gccaacaac      2520 cagtttgaca cagagatgct gcaagccatg atcttggcgt ccgccagtga agctgctgat    2580
gggagctcca ccctgggagg gggtgccggc accatgggat tgagcgcccg ctacggaccc    2640
cagttcaccc tgcagcacgt gcccgactac cgccagaatg tctacatccc aggcagcaat    2700
gccacactga ccaacgcagc tggcaagcgg gatggcaagg ccccagcagg tggcaatggc    2760
aacaagaaga agtcgggcaa gaaggagaag aagtaacatg gaggccaggc caagagccac    2820
agggcggcct ctccccaacc agcccagctt ctccttacct gcacccaggc ctcagagttt    2880
cagggctaac ccccagaata ctggtagggg ccaaggccat gctccccttg ggaaacagaa    2940
acaagtgccc agtcagcacc taccccttcc cccccagggg gttgaatatg caaaagcagt    3000
tccgctggga acccccatcc aatcaactgc tgtacccatg ggggtagtgg ggttactgta    3060
gacaccaaga accatttgcc acaccccgtt tagttacagc tgaactcctc catcttccaa    3120
atcaatcagg cccatccatc ccatgcctcc ctcctcccca ccccactcca acagttcctc    3180
tttcccgagt aaggtggttg gggtgttgaa gtaccaagta acctacaagc ctcctagttc    3240
tgaaaagttg gaagggcatc atgaccctctt ggcctctcct ttgattctca atcttccccc    3300
```

```
aaagcatggt ttggtgccag ccccttcacc tccttccaga gcccaagatc aatgctcaag    3360
ttttggagga catgatcacc atccccatgg tactgatgct tgctggattt agggagggca    3420
ttttgctacc aagcctcttc ccaacgccct ggggaccagt cttctgtttt gttttcatt     3480 gtttgacgtt tccactgcat gccttgactt ccccccacctc ctcctcaaac aagagactcc   3540
actgcatgtt ccaagacagt atggggtggt aagataagga agggaagtgt gtggatgtgg    3600
atggtggggg catggacaaa gcttgacaca tcaagttatc aaggccttgg aggaggctct    3660
gtatgtcctc aggggactga caacatcctc cagattccag ccataaacca ataactaggc    3720 tggaccccttc ccactacata ataggctca gcccaggcag ccagctttgg gctgagctaa    3780
caggaccaat ggattaaact ggcatttcag tccaaggaag ctcgaagcag gtttaggacc    3840
aggtcccctt gagaggtcag aggggcctct gtgggtgctg ggtactccag aggtgccact    3900
ggtggaaggg tcagcggagc cccagcagga agggtgggcc agccaggcca ttcttagtcc    3960
ctgggttggg gaggcaggga gctagggcag ggaccaaatg aacagaaagt ctcagcccag    4020
gatgggcgtt cttcaacagg gccctgccc tcctgaagcc tcagtccttc accttgccag     4080
gtgccgtttc tcttccgtga aggccactgc ccaggtcccc agtgcgcccc ctagtggcca    4140
tagcctggtt aaagttcccc agtgcctcct tgtgcataga ccttcttctc ccaccccctt    4200
ctgcccctgg gtccccggcc atccagcggg gctgccagag aaccccagac ctgcccttac    4260
agtagtgtag cgccccctcc ctctttcggc tggtgtagaa tagccagtag tgtagtgcgg    4320
tgtgctttta cgtgatggcg ggtgggcagc gggcggcggg ctccgcgcag ccgtctgtcc    4380
ttgatctgcc cgcggcggcc cgtgttgtgt tttgtgctgt gtccacgcgc taaggcgacc    4440
ccctcccccg tactgacttc tcctataagc gcttctcttc gcatagtcac gtagctccca    4500 ccccacccctc ttcctgtgtc tcacgcaagt tttatactct aatatttata tggcttttt    4560 tcttcgacaa aaaataata aaacgtttct ctgaaaagc tg                         4602

<210> SEQ ID NO 29
<211> LENGTH: 3114
<212> TYPE: DNA
<213> ORGANISM: Homo sapiens

<400> SEQUENCE: 29
aatcccagct cgcagccctt gctccgcgtg tactcacggg aggactcgca gacgttactg      60
ccctcttgcg tgccccggcc accccgggc ggcttgtagc cggtgcgcgg ggtggctggg      120
gctacgtgca gagctgtcgc ggagccggaa cagcagcggt gaagcccctc ggctcggccg     180
agaccgccgt gcccactgct cgcctcggtt gccgccgctt tagccgcagc cgctgctgcc     240
gccgccgggg gagaggcagc ctattgtctt tctccgcggc gaaggtgagg agctgtctcg     300
gctcggcccg cggggagcc ccgggagccg cacggagatg gaggaggaca tctggacagt     360
gagcaggagg cgcttcggcc catgccgaac atcccagggg acctggagag ccggaggcc     420 atggtggcat ttttcaactc cgctggagcc aatgcccagg aggaacaaag ggtgtgctgc     480
cagcccctgg ctcacccagt ggcctcgtcc cagaaaaagc cagaggtagc ggccccagcc     540
ccagagagtg ggggtgagtc tgtgtttggg gagacccacc gggccctgca gggggccatg     600
gagaagctgc agcgacttta tggaaggaga aggtggacct gaaggagcgg gtagagaaac    660
tagagcttca attcatccac ctctcaggac agacagacac catagggaga aagtacatca    720
gccagggggc agtgtcagag acgcagcact gggagaggac gacatcgtca ggctggccca    780
ggaccaggag gagatgaagg tgaacctgca ggagctgcgg ggcaggtgtt gcagcttgtg    840
```

```
ggagaccaca aggaggggca tggcaaattc tgaccattgc ccagaaccct gctgatgagc      900
ccactctagg agcccaata gcccaggagc ttgggtgtgc tgacgagcag ggtgatcacc      960
actggattgc tgacagatag aggacgtggg accgtgacta tcaccctaa tctgcagtgg     1020
atttggctct cggcactccc aggctgggag ctggatacct gccctggcag catgactcag     1080
actgcatgac agtcacagac tcgcctctgc tcctgtggtc cagtggccgg acaccccctg     1140
ggatggctca aaggagtcag gacttggaag tggggacatc agggtagctg aaggaaatcc     1200
acacacccag agcatctcgg agttcagact ctcagacctg aagtaggcgc ccccgggact     1260
gggctaggag ttggacggaa tggaggatgg aggacagcga gaagaaagga agagaaatgc     1320
aaagtgtggg cagccgccaa gagtgaaaat agagggaagt gtcatgcaag tgctggacag     1380
aaggcggcag gtgggacgag ccccacagcc ccctcctcaa aaacgaccac ctccaggact     1440
cagtgatccc tgggggcag gctctgccag ccctcggcca cacgtggctc cggcacccat      1500
ggtcccagtg ccttggatgg agacggccag ttctggcggc cagatgtggt gctctggaat     1560
ccagtcccat ttccttcctg gccacgcctg tccagcggcc tcttcagccg cattcagccc     1620
ctacttacct ggggaccccg gctggggcac gagagcacca gggggtagg gcccaaaggg      1680
atcaggggaa gcctctggcc tggagggtat ggggcacgct tccccaaggg cggacccggc     1740
aggaggaagc ccaggagctg gtcctgccg cccaggagct gggccctgcc acccaggccg      1800
ggctagggac atggcagggc ctgggcatcc tgacgctgga cttgggcgac ctgggaggca     1860
cagggagggg agagatgggc gaccccgccc cagcgcagtg ccggccacac cccaaggcag     1920
ttgccagagc ttaagccccg ccccagcag cgagaacatc ccagctccac acccccccc      1980
ccccgcagc cagtgctcct tgtcaagctc ccccgtcac tccaggtggg agccaccccg     2040
gtgagggggt gtgccacttg cccccaggc actcctctgg gcatcccggg tgggggattt     2100
tggggccgtg gggggcagtc tttggtacct gtgttcgtca gggatgctct gacaaccagg     2160
tgtcgtccac gggcggggc atgggcatgg tgacagtggt cctgttgatg tcaccgatga      2220
tgctgagcgc ctccttcagc gcgtggtgca tgtgcagcat ctcgtcgtgc tgctgtgcct     2280
gctctgccaa ctcctccatc agtgtgttct ggttcccaca tgagtacata ttggccagca     2340
gctccgagat gatgaactcc ggggtctgag agtgggcaaa cagggaagaa ggttgggacc     2400
tggtgcctgt gccgccctgg ctgccttgct gggcccttct gggactgtgc gctggacttg     2460
gagccccttg gagtatggct tttcacacgg gcttctatac cgcttcgact ggaagatcca     2520
cctccccact gccttttctc actcagatgg ggacaccgag gtccagagga aaagacacct     2580
gtcaaatgtc acagatctgg gaggggactt aagacttatc atgccaagag gacacctgtc     2640
tactcagttt ttttttggtg gggcggggg cggtgatagg gtctcgctct gtcaccaggc      2700
tggagtacag tgatgactgc tcactgcagc ctccacctcc tgggctcaaa gtgatcctcc     2760
aacgtcagcc tctcgaggag ctaggactac aggcacatgc caccaccaag cccagctatt     2820
tttaaaattt ttgtgtggag acaaggtctc actatgtggc ccaggctggt ctcgaactcc     2880
tgggctcaag tgatcctcct gcctcggcct ccaggagtgg gagttggagt tgatgcctgg     2940
atacaggagc tctgtgggtg ggagtgagac aaaacacagg gtcctgagct ctggggacca     3000
agcaatgtcc tctggtgaaa aaaatcctgg acttgctggc agaagatttg cctcttactc     3060
gccatgtgct ctgaatacat ttacctgccc tctgggaaaa aaaaaaaaaa aaaa          3114
```

<210> SEQ ID NO 30

```
<211> LENGTH: 3357
<212> TYPE: DNA
<213> ORGANISM: Homo sapiens

<400> SEQUENCE: 30
aatcccagct cgcagccctt gctccgcgtg tactcacggg aggactcgca gacgttactg      60
ccctcttgcg tgccccggcc accccgggcc ggcttgtagc cggtgcgcgg ggtggctggg     120
gctacgtgca gagctgtcgc ggagccggaa cagcagcggt gaagcccctc ggctcggccg     180
agaccgccgt gcccactgct cgcctcggtt gccgccgctt tagccgcagc cgctgctgcc     240
gccgccgggg gagaggcagc ctattgtctt tctccgcggc gaaggtgagg agctgtctcg     300
gctcggcccg cggggagcc ccgggagccg cacggtggca tttttcaact ccgctggagc     360
caatgcccag gaggaacaaa gggtgtgctg ccagcccctg gctcacccag tggcctcgtc     420
ccagaaaaag ccagaggtag cggccccagc cccagagagt ggggtgagt ctgtgtttgg     480 ggagacccac cgggcctgc aggggccat ggagaagctg cagcgacttt atggaaggag     540
aaggtggacc tgaaggagcg ggtagagaaa ctagagcttc aattcatcca cctctcagga     600
cagacagaca ccatagggag aaagtacatc agccaggggg cagtgtcaga gacgcagcac     660
tgggagagga ggacatcgtc aggctggccc aggaccagga ggagatgaag gtgaacctgc     720
aggagctgcg gggcaggtgt tgcagcttgt gggagaccac aaggaggggc atggcaaatt     780
ctgaccattg cccagaaccc tgctgatgag cccactctag gagccccaat agcccaggag     840
cttgggtgtg ctgacgagca gggtgatcac cactggattg ctgacagata gaggacgtgg     900
gaccgtgact atcaccccta atctgcagtg gatttggctc tcggcactcc caggctggga     960
gctggatacc tgccctggca gcatgactca gactgcatga cagagaacgt ggccagtgga    1020
gacggcacac tggaaatcag agtgaatgtt cttgaaagag ggtcacgggt caacaaggcc    1080
cagccaaagg atgcagtaga accatttttcc ttagaaatct ttgggagtga agtaggcttc    1140
agccactccc atccctgccc tcgcggctac cactacccca ttagtttaga cagggtcggg    1200
cggggagggg tgtggagaag aaatgagctt gcctgtggcc cccaggctcc ctctgtccta    1260
gctcaggtct gggtgccatt ctttacactc gtgtgctcgc tcacgcacac atcacacacc    1320
ttgctggtca cacagtcaca gactcgcctc tgctcctgtg gtccagtggc cggacacccc    1380
ctgggatggc tcaaggagt caggacttgg aagtggggac atcagggtag ctgaaggaaa    1440
tccacacacc cagagcatct cggagttcag actctcagac ctgaagtagg cgcccccggg    1500
actgggctag gagttggacg gaatggagga tggaggacag cgagaagaaa ggaagagaaa    1560
tgcaaagtgt gggcagccgc caagagtgaa aatagaggga agtgtcatgc aagtgctgga    1620
cagaaggcgg caggtgggac gagccccaca gcccctcct caaaaacgac cacctccagg    1680
actcagtgat ccctgggggg caggctctgc cagccctcgg ccacacgtgg ctccggcacc    1740
catggtccca gtgccttgga tggagacggc cagttctggc ggccagatgt ggtgctctgg    1800
aatccagtcc catttccttc ctggccacgc ctgtccagcg gcctcttcag ccgcattcag    1860
cccctactta cctggggacc ccggctgggg cacgagagca ccaggggggt agggcccaaa    1920
gggatcaggg gaagcctctg gcctggaggg tatgggcac gcttccccaa gggcggaccc    1980
ggcaggagga agcccaggag ctgggtcctg ccgcccagga gctgggccct gccacccagg    2040
ccgggctagg gacatggcag ggcctgggca tcctgacgct ggacttgggc gacctgggag    2100
gcacagggag gggagagatg ggcgacccg ccccagcgca gtgccggcca cacccaaggg    2160
cagttgccag agcttaagcc ccgccccag cagcgagaac atcccagctc cacaccccc    2220
```

| | | | |
|---|---|---|---|
| ccccccccgc | agccagtgct | ccttgtcaag | ctcccccgt cactccaggt gggagccacc | 2280 |
| ccggtgaggg | ggtgtgccac | ttgccccag | ggcactcctc tgggcatccc gggtggggga | 2340 |
| ttttggggcc | gtggggggca | gtctttggta | cctgtgttcg tcaggatgc tctgacaacc | 2400 |
| aggtgtcgtc | cacgggcggg | ggcatgggca | tggtgacagt ggtcctgttg atgtcaccga | 2460 |
| tgatgctgag | cgcctccttc | agcgcgtggt | gcatgtgcag catctcgtcg tgctgctgtg | 2520 |
| cctgctctgc | caactcctcc | atcagtgtgt | tctggttccc acatgagtac atattggcca | 2580 |
| gcagctccga | gatgatgaac | tccggggtct | gagagtgggc aaacagggaa gaaggttggg | 2640 |
| acctggtgcc | tgtgccgccc | tggctgcctt | gctgggccct tctgggactg tgcgctggac | 2700 |
| ttggagcccc | ttggagtatg | cttttcaca | cgggcttcta taccgcttcg actggaagat | 2760 |
| ccacctcccc | actgccttt | ctcactcaga | tggggcacacc gaggtccaga ggaaaagaca | 2820 |
| cctgtcaaat | gtcacagatc | tgggagggga | cttaagactt atcatgccaa aggacacct | 2880 |
| gtctactcag | ttttttttg | gtgggcggg | ggcggtgat agggtctcgc tctgtcacca | 2940 |
| ggctggagta | cagtgatgac | tgctcactgc | agcctccacc tcctgggctc aaagtgatcc | 3000 |
| tccaacgtca | gcctctcgag | gagctaggac | tacaggcaca tgccaccacc aagcccagct | 3060 |
| atttttaaaa | ttttgtgtg | gagacaaggt | ctcactatgt ggcccaggct ggtctcgaac | 3120 |
| tcctgggctc | aagtgatcct | cctgcctcgg | cctccaggag tgggagttgg agttgatgcc | 3180 |
| tggatacagg | agctctgtgg | gtgggagtga | acaaaacac agggtcctga gctctgggga | 3240 |
| ccaagcaatg | tcctctggtg | aaaaaaatcc | tggacttgct ggcagaagat ttgcctctta | 3300 |
| ctcgccatgt | gctctgaata | catttacctg | ccctctggga aaaaaaaaaa aaaaaaa | 3357 |

<210> SEQ ID NO 31
<211> LENGTH: 2975
<212> TYPE: DNA
<213> ORGANISM: Homo sapiens

<400> SEQUENCE: 31

| | | | |
|---|---|---|---|
| aatcccagct | cgcagccctt | gctccgcgtg | tactcacggg aggactcgca gacgttactg | 60 |
| ccctcttgcg | tgccccggcc | accccgggc | ggcttgtagc cggtgcgcgg ggtggctggg | 120 |
| gctacgtgca | gagctgtcgc | ggagccggaa | cagcagcggt gaagcccctc ggctcggccg | 180 |
| agaccgccgt | gcccactgct | cgcctcggtt | gccgccgctt tagccgcagc cgctgctgcc | 240 |
| gccgccgggg | gagaggcagc | ctattgtctt | tctccgcggc gaaggtggca ttttcaact | 300 |
| ccgctggagc | caatgcccag | gaggaacaaa | gggtgtgctg ccagcccctg gctcacccag | 360 |
| tggcctcgtc | ccagaaaaag | ccagaggtag | cggccccagc cccagagagt gggggtgagt | 420 |
| ctgtgtttgg | ggagacccac | cggggccctgc | agggggccat ggagaagctg cagcgacttt | 480 |
| atggaaggag | aagtggacc | tgaaggagcg | ggtagagaaa ctagagcttc aattcatcca | 540 |
| cctctcagga | cagacagaca | ccataggag | aaagtacatc agccagggg cagtgtcaga | 600 |
| gacgcagcac | tgggagagga | ggacatcgtc | aggctggccc aggaccagga ggagatgaag | 660 |
| gtgaacctgc | aggagctgcg | gggcaggtgt | tgcagcttgt gggagaccac aaggaggggc | 720 |
| atggcaaatt | ctgaccattg | cccagaaccc | tgctgatgag cccactctag agccccaat | 780 |
| agcccaggag | cttgggtgtg | ctgacgagca | gggtgatcac cactggattg ctgacagata | 840 |
| gaggacgtgg | gaccgtgact | atcaccccta | atctgcagtg gatttggctc tcggcactcc | 900 |
| caggctggga | gctggatacc | tgccctggca | gcatgactca gactgcatga cagtcacaga | 960 |

```
ctcgcctctg ctcctgtggt ccagtggccg gacaccccct gggatggctc aaaggagtca    1020
ggacttggaa gtggggacat cagggtagct gaaggaaatc cacacaccca gagcatctcg    1080
gagttcagac tctcagacct gaagtaggcg ccccgggac tgggctagga gttggacgga    1140
atggaggatg gaggacagcg agaagaaagg aagagaaatg caaagtgtgg gcagccgcca    1200
agagtgaaaa tagagggaag tgtcatgcaa gtgctggaca gaaggcggca ggtgggacga    1260
gccccacagc ccctcctca aaaacgacca cctccaggac tcagtgatcc ctgggggca    1320 ggctctgcca gccctcggcc acacgtggct ccggcaccca tggtcccagt gccttggatg    1380
gagacggcca gttctggcgg ccagatgtgg tgctctggaa tccagtccca tttccttcct    1440
ggccacgcct gtccagcggc ctcttcagcc gcattcagcc cctacttacc tggggacccc    1500 ggctgggca cgagagcacc agggggtag ggcccaaagg gatcagggga agcctctggc    1560
ctggagggta tggggcacgc ttccccaagg gcggacccgg caggaggaag cccaggagct    1620
gggtcctgcc gcccaggagc tgggccctgc cacccaggcc gggctaggga catggcaggg    1680
cctgggcatc ctgacgctgg acttgggcga cctgggaggc acaggagggg agagatggg    1740 cgaccccgcc ccagcgcagt gccggccaca ccccaaggca gttgccagag cttaagcccc    1800
gcccccagca gcgagaacat cccagctcca caccccccc cccccgcag ccagtgctcc    1860 ttgtcaagct ccccccgtca ctccaggtgg gagccacccc ggtgaggggg tgtgccactt    1920
gcccccaggg cactcctctg ggcatcccgg gtggggatt ttggggccgt gggggcagt    1980 ctttggtacc tgtgttcgtc agggatgctc tgacaaccag gtgtcgtcca cgggcggggg    2040
catgggcatg gtgacagtgg tcctgttgat gtcaccgatg atgctgagcg cctccttcag    2100
cgcgtggtgc atgtgcagca tctcgtcgtg ctgctgtgcc tgctctgcca actcctccat    2160
cagtgtgttc tggttcccac atgagtacat attggccagc agctccgaga tgatgaactc    2220
cggggtctga gagtgggcaa acagggaaga aggttgggac ctggtgcctg tgccgccctg    2280
gctgccttgc tgggcccttc tgggactgtg cgctggactt ggagcccctt ggagtatggc    2340
ttttcacacg ggcttctata ccgcttcgac tggaagatcc acctccccac tgccttttct    2400
cactcagatg gggacaccga ggtccagagg aaaagacacc tgtcaaatgt cacagatctg    2460 ggagggact taagacttat catgccaaga ggacacctgt ctactcagtt ttttttggt    2520 ggggcgggg gcggtgatag ggtctcgctc tgtcaccagg ctggagtaca gtgatgactg    2580
ctcactgcag cctccacctc ctgggctcaa agtgatcctc caacgtcagc ctctcgagga    2640
gctaggacta caggcacatg ccaccaccaa gcccagctat ttttaaaatt tttgtgtgga    2700
gacaaggtct cactatgtgg cccaggctgg tctcgaactc ctgggctcaa gtgatcctcc    2760
tgcctcggcc tccaggagtg ggagttggag ttgatgcctg gatacaggag ctctgtgggt    2820
gggagtgaga caaaacacag ggtcctgagc tctggggacc aagcaatgtc ctctggtgaa    2880
aaaaatcctg gacttgctgg cagaagattt gcctcttact cgccatgtgc tctgaataca    2940
tttacctgcc ctctgggaaa aaaaaaaaa aaaaa                                2975
```

<210> SEQ ID NO 32
<211> LENGTH: 1173
<212> TYPE: DNA
<213> ORGANISM: Homo sapiens
<220> FEATURE:
<221> NAME/KEY: modified_base
<222> LOCATION: (735)..(735)
<223> OTHER INFORMATION: a, c, t, g, unknown or other

<400> SEQUENCE: 32

```
agagtacatg cggcgggggg aagtttagga gttgaggaaa gaagattaaa gagcgcgagg      60
aggaagggaa tttgaaggag aagaagaata tctggagatc cttggcatca ccagggagca     120
gtcaggcaaa tatgagtgca aagctgccaa cgaggtctcc tcggcggatg tcaaacaagt     180
caaggtcact gtgaactatc ctcccactat cacagaatcc aagagcaatg aagccaccac     240
aggacgacaa gcttcactca aatgtgaggc ctcggcagtg cctgcacctg actttgagtg     300
gtaccgggat gacactagga taaatagtgc caatggcctt gagattaaga gcacggaggg     360
ccagtcttcc ctgacggtga ccaacgtcac tgaggagcac tacggcaact acacctgtgt     420
ggctgccaac aagctggggg tcaccaatgc cagcctagtc cttttcagac ctgggtcggt     480
gagaggaata aatggatcca tcagtctggc cgtaccactg tggctgctgg cagcatctct     540
gctctgcctt ctcagcaaat gttaatagaa taaaaattta aaataattt aaaaaacaca     600 caaaaatgtg tcacacagaa tacagagaga gagagacaga gagagagaga gagagagaga     660
tgggggagac cgtttatttc acaactttgt gtgtttatac atgaagggg aataagaaa      720 gtgaagaaga aaatnacaac atttaaaaca attttacagt ccatcattaa aaatttatgt     780
atcattcagg atggagaagg ttctactggg atatgtttat atctactaag caaatgtatg     840
ctgtgtaaag actacaccac actaaggaca tctggatgct gtaaaataa gagaagaacc      900 agatggatat taagccccc aacacacact ttatccttcc ttccttcatc ttttttcatc      960
tgtggggaag aaaataaggt cttgcctttg gtgtttatat ttccataacc ttttaattct    1020 attttttcatt tgagctgact tgtagccact tcagactatc aatggaatct tatgttgagc    1080
ctttctctgg ctttccttcc tccactatct ctccaacttt agagatcatc ccctctccct    1140
ccagtgcgtt ctatctcccc cacacccacc caa                                 1173
```

<210> SEQ ID NO 33
<211> LENGTH: 1416
<212> TYPE: DNA
<213> ORGANISM: Homo sapiens
<220> FEATURE:
<221> NAME/KEY: modified_base
<222> LOCATION: (622)..(622)
<223> OTHER INFORMATION: a, c, t, g, unknown or other
<220> FEATURE:
<221> NAME/KEY: modified_base
<222> LOCATION: (698)..(698)
<223> OTHER INFORMATION: a, c, t, g, unknown or other
<220> FEATURE:
<221> NAME/KEY: modified_base
<222> LOCATION: (746)..(746)
<223> OTHER INFORMATION: a, c, t, g, unknown or other
<220> FEATURE:
<221> NAME/KEY: modified_base
<222> LOCATION: (765)..(766)
<223> OTHER INFORMATION: a, c, t, g, unknown or other

<400> SEQUENCE: 33

```
acatggggag gttgcagtgt gtgtatatac acaacatcaa gagcaggaaa atggactcat      60
tagggaggca ggcagtcatt accactcaca ctgtacttcc agggagacac cgattataag     120
aagagaaact cagcgctggg gaagaagatt aacttactct taatgatctt ccaacacttg     180
agaaggtcag tagccctcca tctgtcattc tccaagttca ccaacagctt atccacccat     240
caaaggtgct tttgtaacaa aatccatgca taatgaaacc agaaaggaa gggaatttga      300 aggagaagaa gaatatctgg agatccttgg catcaccagg gagcagtcag gcaaatatga     360
gtgcaaagct gccaacgagg tctcctcggc ggatgtcaaa caagtcaagg tcactgtgaa     420
```

| | |
|---|---|
| ctatcctccc actatcacag aatccaagag caatgaagcc accacaggac gacaagcttc | 480 |
| actcaaatgt gaggcctcgg cagtgcctgc acctgacttt gagtggtacc gggatgacac | 540 |
| taggataaat agtgccaatg gccttgagat taagagcacg gagggccagt cttccctgac | 600 |
| gtgaccaacg tcactgagag gngagcacta cggcaactac acctgtgtgg ctgccaacaa | 660 |
| gctgggggtc acaatgccag cctagtcctt ttcagacntg gkysgtgaga ggaataaatg | 720 |
| gatccatcag tctggccgta ccactngtgg ctgctggcag caatnntctc tgctctgccg | 780 |
| tctcagcaaa tgttaataga ataaaaattt aaaaataatt taaaaaacac acaaaaatgc | 840 |
| gtcacacaga atacagagag agagagacag agagagagag agagagagag atggggagaa | 900 |
| ccgtttattt cacaactttg tgtgtttata catgaagggg gaaataagaa agtgaagaag | 960 |
| aaaatacaac atttaaaaca attttacagt ccatcattaa aaatttatgt atcattcagg | 1020 |
| atggagaagg ttctactggg atatgtttat atctactaag caaatgtatg ctgtgtaaag | 1080 |
| actacaccac actaaggaca tctggatgct gtaaaaataa gagaagaacc agatggatat | 1140 |
| taagcccccc aacacacact ttatccttcc ttccttcatc tttttcatc tgtggggaag | 1200 |
| aaaataaggt cttgccttg gtgtttatat ttccataacc ttttaattct attttcatt | 1260 |
| tgagctgact tgtagccact tcagactatc aatggaatct tatgttgagc cttctctgg | 1320 |
| ctttccttcc tccactatct ctccaacttt agagatcatc ccctctccct ccagtgcgtt | 1380 |
| ctatctcccc cacacccacc caagcttggc gtaatc | 1416 |

<210> SEQ ID NO 34
<211> LENGTH: 1260
<212> TYPE: DNA
<213> ORGANISM: Homo sapiens

<400> SEQUENCE: 34

| | |
|---|---|
| caacgcagag tacatgggac acaacatcaa gagcaggaaa atggactcat tagggaggca | 60 |
| ggcagtcatt accactcaca ctgtacttcc agggagacac cgattataag aagagaaact | 120 |
| cagcgctggg gaagaaggaa gggaatttga aggagaagaa gaatatctgg agatccttgg | 180 |
| catcaccagg gagcagtcag gcaaatatga gtgcaaagct gccaacgagg tctcctcggc | 240 |
| ggatgtcaaa caagtcaagg tcactgtgaa ctatcctccc actatcacag aatccaagag | 300 |
| caatgaagcc accacaggac gacaagcttc actcaaatgt gaggcctcgg cagtgcctgc | 360 |
| acctgacttt gagtggtacc gggatgacac taggataaat agtgccaatg gccttgagat | 420 |
| taagagcacg gagggccagt cttccctgac ggtgaccaac gtcactgagg agcactacgg | 480 |
| caactacacc tgtgtggctg ccaacaagct gggggtcacc aatgccagcc tagtcctttt | 540 |
| cagacctggg tcggtgagag gaataaatgg atccatcagt ctggccgtac cactgtggct | 600 |
| gctggcagca tctctgctct gccttctcag caaatgttaa tagaataaaa atttaaaaat | 660 |
| aatttaaaaa acacacaaaa atgcgtcaca cagaatacag agagagagac agagagagag | 720 |
| agagagagag agagatgggg agaccgtttt atttcacaac tttgtgtgtt tatacatgaa | 780 |
| ggggggaaata agaaagtgaa gaagaaaata caacatttaa aacaatttta cagtccatca | 840 |
| ttaaaaattt atgtatcatt caggatggag aaggttctac tgggatatgt ttatatctac | 900 |
| taagcaaatg tatgctgtgt aaagactaca ccacactaag gacatctgga tgctgtaaaa | 960 |
| ataagagaag aaccagatgg atattaagcc ccccaacaca cactttatcc ttccttcctt | 1020 |
| catcttttt catctgtggg gaagaaaata aggtcttgcc tttggtgttt atatttccat | 1080 |
| aaccttttaa ttctattttt catttgagct gacttgtagc cacttcagac tatcaatgga | 1140 |

```
atcttatgtt gagcctttct ctggctttcc ttcctccact atctctccaa ctttagagat    1200
catcccctct ccctccagtg cgttctatct cccccacacc cacccaagct tggcgtaatc    1260

<210> SEQ ID NO 35
<211> LENGTH: 341
<212> TYPE: DNA
<213> ORGANISM: Homo sapiens

<400> SEQUENCE: 35
acatggggaa gtttaggagt tgaggaaaga agattaaaga gcgcgaggag attttataga      60
ccagtggaat acagcccttg tgcatatgaa gatcaggtga caagtttgst gcctaccagc    120
ctccacagca atatgccctt tcacgagtcc ctatcgccca ggctggagtg cagtggcgtg    180
atctctgctc actgcaacct ccgcctcccg ggttcaagtg attctcttgc ctcagcctcc    240
cgagtagctg ggattacagg aagggaattt gaaggagaag aagaatatct ggagatcctt    300
ggcatcacca gggagcagtc aggcaaaagc ttggcgtaat c                        341

<210> SEQ ID NO 36
<211> LENGTH: 214
<212> TYPE: DNA
<213> ORGANISM: Homo sapiens

<400> SEQUENCE: 36
acatggggga ggaaagaaga ttaaagagcg cgaggagatt ttatagacca gtggaataca     60
ggccttgtgc atatgaagat caggtgacaa gtttgctgcc taccagcctc cacagcaata   120 tgcccttca cggaagggaa tttgaaggag aagaagaata tctggagatc cttggcatca   180
ccagggagca gtcaggcaaa agcttggcgt aatc                               214

<210> SEQ ID NO 37
<211> LENGTH: 225
<212> TYPE: DNA
<213> ORGANISM: Homo sapiens

<400> SEQUENCE: 37
acatggggga ggaaagaaga ttaaagagcg cgaggagaca gagtccctat cgcccaggct     60
ggagtgcagt ggcgtgatct ctgctcactg caacctccgc ctcccggtt caagtgattc   120 tcttgcctca gcctcccgag tagctgggat tacaggaagg gaatttgaag gagaagaaga   180
atatctggag atccttggca tcaccaggga gcagtcaggc aaaag                   225

<210> SEQ ID NO 38
<211> LENGTH: 132
<212> TYPE: DNA
<213> ORGANISM: Homo sapiens

<400> SEQUENCE: 38
acatggggaa gtttaggagt tgaggaaaga agattaaaga gcgcgaggag gaagggaatt     60
tgaaggagaa gaagaatatc tggagatcct tggcatcacc agggagcagt caggcaaaag   120
cttggsgtaa tc                                                        132

<210> SEQ ID NO 39
<211> LENGTH: 282
<212> TYPE: DNA
<213> ORGANISM: Homo sapiens

<400> SEQUENCE: 39
```

```
acatgggggg gcgggggaa gtttaggagt tgaggaaaga agattaaaga gcgcgaggag    60
attaacttac tcttaatgat cttccaacac ttgagaaggt cagtagccct ccatctgtca   120
ttctccaagt tcaccaacag cttatccacc catcaaaggt gcttttgtaa caaaatccat   180
gcataatgaa accaagaaag gaagggaatt tgaaggagaa gaagaatatc tggagatcct   240
tggcatcacc agggagcagt caggcaaaag cttggcgtaa tc                      282
```

<210> SEQ ID NO 40
<211> LENGTH: 199
<212> TYPE: DNA
<213> ORGANISM: Homo sapiens

<400> SEQUENCE: 40

```
acatggggaa gagcaggaaa atggactcat tagggaggca ggcagtcatt accactcaca    60
ctgtacttcc agggagacac cgattataag aagagaaact cagcgctggg gaagaaggaa   120
gggaatttga aggagaagaa gaatatctgg agatccttgg catcaccagg gagcagtcag   180
gcaaaagctt ggcgtaatc                                                199
```

<210> SEQ ID NO 41
<211> LENGTH: 364
<212> TYPE: DNA
<213> ORGANISM: Homo sapiens

<400> SEQUENCE: 41

```
acatgggag tacatgggga tatacacaac atcaagagca ggaaaatgga ctcattaggg     60
aggcaggcag tcattaccac tcacactgta cttccaggga gacaccgatt ataagaagag   120
aaactcagcg ctggggaaga agattaactt actcttaatg atcttccaac acttgagaag   180
gtcagtagcc ctccatctgt cattctccaa gttcaccaac agcttatcca cccatcaaag   240
gtgcttttgt aacaaaatcc atgcataatg aaaccaagaa aggaagggaa tttgaaggag   300
aagaagaata tctggagatc cttggcatca ccagggagca gtcaggcaaa agcttggcgt   360
aatc                                                                364
```

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
gcgttctatc tcccccacac ccaccc                                         26
```

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
gcgttctatc tcccccaca                                                 19
```

<210> SEQ ID NO 44
<211> LENGTH: 26
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 44
gcatcaccag ggagcagtca ggcaaa                                            26

<210> SEQ ID NO 45
<211> LENGTH: 142
<212> TYPE: DNA
<213> ORGANISM: Homo sapiens

<400> SEQUENCE: 45
agattaactt actcttaatg atcttccaac acttgagaag gtcagtagcc ctccatctgt       60
cattctccaa gttcaccaac agcttatcca cccatcaaag gtgcttttgt aacaaaatcc     120
atgcataatg aaaccaagaa ag                                              142

<210> SEQ ID NO 46
<211> LENGTH: 888
<212> TYPE: DNA
<213> ORGANISM: Homo sapiens

<400> SEQUENCE: 46
ggaggaggat aggaagcagg aaagcgggag agctcgaggg acaaggggc tcggtgtgtt        60 tacaccaggc acgggctacg agcgtccatc ccggcccctg gcttgcgctc ccgaagagga     120
gagcaaggct gttctgggat ccggccgtcg tgcggcaaga ggcttgtctg tccgggttgc     180
cggaaccagg agaacccaga gggaaaccga gggaaaggag cggcgcgttt tactagagag     240
agcgcgagcg gaagaggcga gagcaggagc gcgcgaggga gcatcgagcg cagcggagac     300
atgaggacct actggctgca cagcgtctgg gtgctgggct ttttcctgtc cctcttctca     360
ttgcaaggac tgcctgttcg cagcgtggat tttaaccgag gcacggacaa catcaccgtg     420
aggcagggga acacagccat cctcaggtgc gttgtagaag acaagaactc aaaggtggcc     480
tggttgaacc gttctggcat cattttgct ggacatgaca gtggtctct ggacccacgg       540 gttgagctgg agaaacgcca ttctctggaa tacagcctcc gaatccagaa ggtggatgtc     600
tatgatgagg gttcctacac ttgctcagtt cagacacagc atgagcccaa gacctcccaa     660
gtttacttga tcgtacaagt cccaccaaag atctccaata tctcctcgga tgtcactgtg     720
aatgagggca gcaacgtgac tctggtctgc atggccaatg gccgtcctga acctgttatc     780
acctggagac accttacacc aactggaagg gaatttgaag gagaagaaga atatctggag     840
atccttggca tcaccaggga gcagtcaggc aaaagcttgg cgtaatcc                  888

<210> SEQ ID NO 47
<211> LENGTH: 365
<212> TYPE: DNA
<213> ORGANISM: Homo sapiens

<400> SEQUENCE: 47
ggaggaggat aggaagcagg aaagcgggag agctcgaggg acaaggggc tcggtgtgtt        60 tacaccaggc acgggctacg agcgtccatc ccggcccctg gcttgcgctc ccgaagagga     120
gagcaaggct gttctgggat ccggccgtcg tgcggcaaga ggcttgtctg tccgggttgc     180
cggaaccagg agaacccaga gggaaaccga gggaaaggag cggcgcgttt tactagagag     240
agcgcgagcg gaagaggcga gagcaggagc gcgcgaggga gcatcgagcg cagcggagac     300
atgaggacct actggctgca cagcgtctgg gtgctgggct ttttcctgtc cctcttctca     360
```

```
ttgca                                                              365

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 40
<212> TYPE: DNA
<213> ORGANISM: Homo sapiens

<400> SEQUENCE: 49
aagattaaag agcgcgagga ggaagggaat ttgaaggaga                         40

<210> SEQ ID NO 50
<211> LENGTH: 40
<212> TYPE: DNA
<213> ORGANISM: Homo sapiens

<400> SEQUENCE: 50
ttctaatttc tcgcgctcct ccttccctta aacttcctct                        40
```